(12) United States Patent
Wilson et al.

(10) Patent No.: US 12,416,017 B2
(45) Date of Patent: Sep. 16, 2025

(54) RECOMBINANT ADENO-ASSOCIATED VIRUS FOR TREATMENT OF GRN-ASSOCIATED ADULT-ONSET NEURODEGENERATION

(71) Applicant: The Trustees of the University of Pennsylvania, Philadelphia, PA (US)

(72) Inventors: James M. Wilson, Philadelphia, PA (US); Christian Hinderer, New Orleans, LA (US); Nimrod Miller, Berwyn, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1060 days.

(21) Appl. No.: 17/431,937

(22) PCT Filed: Feb. 21, 2020

(86) PCT No.: PCT/US2020/019149
§ 371 (c)(1),
(2) Date: Aug. 18, 2021

(87) PCT Pub. No.: WO2020/172490
PCT Pub. Date: Aug. 27, 2020

(65) Prior Publication Data
US 2022/0136008 A1    May 5, 2022

Related U.S. Application Data

(60) Provisional application No. 62/969,108, filed on Feb. 2, 2020, provisional application No. 62/923,812, filed on Oct. 21, 2019, provisional application No. 62/809,329, filed on Feb. 22, 2019.

(51) Int. Cl.
| | | |
|---|---|---|
| C12N 15/86 | (2006.01) | |
| A61K 9/00 | (2006.01) | |
| A61P 25/28 | (2006.01) | |
| C07K 14/47 | (2006.01) | |
| C12N 7/00 | (2006.01) | |
| A61K 38/00 | (2006.01) | |

(52) U.S. Cl.
CPC ............ *C12N 15/86* (2013.01); *A61K 9/0085* (2013.01); *A61P 25/28* (2018.01); *C07K 14/47* (2013.01); *C12N 7/00* (2013.01); *A61K 38/00* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

| | | |
|---|---|---|
| 5,139,941 A | 8/1992 | Muzyezka et al. |
| 5,741,683 A | 4/1998 | Zhou et al. |
| 6,057,152 A | 5/2000 | Samulski et al. |
| 6,204,059 B1 | 3/2001 | Samulski et al. |
| 6,268,213 B1 | 7/2001 | Samulski et al. |
| 6,491,907 B1 | 12/2002 | Rabinowitz et al. |
| 6,660,514 B1 | 12/2003 | Zolotukhin et al. |
| 6,759,237 B1 | 7/2004 | Wilson et al. |
| 6,951,753 B2 | 10/2005 | Shenk et al. |
| 7,094,604 B2 | 8/2006 | Snyder et al. |
| 7,105,345 B2 | 9/2006 | Wilson et al. |
| 7,172,893 B2 | 2/2007 | Rabinowitz et al. |
| 7,186,552 B2 | 3/2007 | Wilson et al. |
| 7,201,898 B2 | 4/2007 | Monahan et al. |
| 7,229,823 B2 | 6/2007 | Samulski et al. |

(Continued)

FOREIGN PATENT DOCUMENTS

| | | |
|---|---|---|
| EP | 1127150 B1 | 5/2007 |
| WO | WO 2000/028061 | 5/2000 |

(Continued)

OTHER PUBLICATIONS

Blast Alignment, https://blast.ncbi.nlm.nih.gov/Blast.cgi?BLAST_SPEC=blast2seq&LINK_LOC=align2seq&PAGE_TYPE=BlastSearch, alignment of SEQ ID No. 1 (subject sequence) of Chen Plotkin with instant SEQ ID No. 1 (query sequence), accessed Jan. 7, 2025 (Year: 2025).*
Powell et al. "Viral expression cassette elements to enhance transgene target specificity and expression in gene therapy." Discovery Medicine 19.102 (2015): 49. (Year: 2015).*
Ahmed, et al. Accelerated lipofuscinosis and ubiquitination in granulin knockout mice suggest a role for progranulin in successful aging. Am J Pathol. Jul. 2010;177(1):311-24.
Ahmed, et al. Progranulin in frontotemporal lobar degeneration and neuroinflammation. J Neuroinflammation. Feb. 11, 2007;4:7.

(Continued)

*Primary Examiner* — Emily A Cordas
(74) *Attorney, Agent, or Firm* — Howson & Howson LLP

(57) ABSTRACT

A recombinant AAV (rAAV) suitable for use in treating adult onset neurodegeneration caused by granulin (GRN) haploinsufficiency, such as progranulin (PGRN)-related frontotemporal dementia (FTD), is provided. The rAAV comprises (a) an adeno-associated virus 1 capsid, and (b) a vector genome packaged in the AAV capsid, said vector genome comprising AAV inverted terminal repeats, a coding sequence for human progranulin, and regulatory sequences which direct expression of the progranulin. Also provided are a method for treating a human patient with PGRN-FTD and other adult onset neurodegeneration caused by granulin (GRN) haploinsufficiencies, comprising delivering to the central nervous system (CNS) a recombinant adeno-associated virus (rAAV) having an adeno-associated virus 1 (AAV1) capsid, said rAAV further comprising a vector genome packaged in the AAV capsid, said vector genome comprising AAV inverted terminal repeats, a coding sequence for human progranulin, and regulatory sequences which direct expression of the progranulin.

18 Claims, 13 Drawing Sheets

Specification includes a Sequence Listing.

(56) References Cited

U.S. PATENT DOCUMENTS

| | | | |
|---|---|---|---|
| 7,439,065 | B2 | 10/2008 | Ferrari et al. |
| 7,588,772 | B2 | 9/2009 | Kay et al. |
| 8,637,255 | B2 | 1/2014 | Wilson et al. |
| 9,486,541 | B2 | 11/2016 | Hutton et al. |
| 9,567,607 | B2 | 2/2017 | Wilson et al. |
| 2010/0267812 | A1 | 10/2010 | Dodge et al. |
| 2010/0324127 | A1 | 12/2010 | Kay |
| 2011/0203007 | A1 | 8/2011 | Klein et al. |
| 2013/0045186 | A1 | 2/2013 | Gao et al. |
| 2013/0287736 | A1 | 10/2013 | Passini et al. |
| 2017/0043035 | A1* | 2/2017 | Wilson ............... A61P 25/00 |
| 2019/0055578 | A1* | 2/2019 | Sah .................. C07K 14/47 |
| 2019/0060359 | A1 | 2/2019 | Norviel et al. |
| 2019/0192693 | A1 | 6/2019 | High et al. |
| 2019/0282662 | A1 | 9/2019 | Kay et al. |
| 2019/0328906 | A1 | 10/2019 | Chen Plotkin et al. |
| 2019/0388507 | A1 | 12/2019 | Kay |
| 2020/0283800 | A1 | 9/2020 | Abeliovich et al. |
| 2020/0308554 | A1 | 10/2020 | Abeliovich et al. |
| 2020/0318115 | A1 | 10/2020 | Abeliovich et al. |
| 2021/0008163 | A1 | 1/2021 | Kay |

FOREIGN PATENT DOCUMENTS

| | | | |
|---|---|---|---|
| WO | WO 2003/042397 | | 5/2003 |
| WO | WO 2005/033321 | | 4/2005 |
| WO | WO 2006/110689 | | 10/2006 |
| WO | WO 2007/146046 | | 12/2007 |
| WO | WO 2010/129021 | | 11/2010 |
| WO | WO 2011/126808 | | 10/2011 |
| WO | WO 2013/049493 | A1 | 4/2013 |
| WO | WO 2017/100674 | | 6/2017 |
| WO | WO 2017/100676 | | 6/2017 |
| WO | WO 2017/100704 | | 6/2017 |
| WO | WO 2017/136500 | A1 | 8/2017 |
| WO | WO 2017/151884 | | 9/2017 |
| WO | WO 2017/160360 | | 9/2017 |
| WO | WO-2017151884 | A1 * | 9/2017 ............. A61K 48/00 |
| WO | WO 2018/013775 | A2 | 1/2018 |
| WO | WO 2018/160582 | | 9/2018 |
| WO | WO 2020/160458 | A1 | 8/2020 |
| WO | WO 2020/172490 | A1 | 8/2020 |
| WO | WO 2022/046988 | | 3/2022 |

OTHER PUBLICATIONS

Amado, et al. AAV-mediated progranulin delivery to a mouse model of progranulin deficiency causes T cell-mediated hippocampal degeneration. bioRxiv 308692, Apr. 27, 2018.

Amado, et al. AAV-mediated progranulin delivery to a mouse model of progranulin deficiency causes T cell-mediated toxicity. Feb. 6, 2019;27(2):465-478.

Arechavaleta-Velasco, et al. Progranulin and its biological effects in cancer. Med Oncol. Nov. 7, 2017;34(12):194.

Armstrong, et al. Criteria for the diagnosis of corticobasal degeneration. Neurology. Jan. 29, 2013;80(5):496-503.

Arrant et al., Restoring neuronal progranulin reverses deficits in a mouse model of frontotemporal dementia, Brain. May 1, 2017;140(5):1447-1465. Published online Mar. 2, 20179.

Arrant, et al. Progranulin gene therapy improves lysosomal dysfunction and microglial pathology associated with frontotemporal dementia and neuronal ceroid lipofuscinosis. J Neurosci. Feb. 28, 2018;38(9):2341-2358.

Arrant, et al. Progranulin haploinsufficiency causes biphasic social dominance abnormalities in the tube test. Genes Brain Behav. Jul. 2016;15(6):588-603.

Bartus, et al. Parkinson's disease gene therapy: success by design meets failure by efficacy. Mol Ther. Mar. 2014;22(3):487-497.

Beel, et al. Progranulin functions as a cathepsin D chaperone to stimulate axonal outgrowth in vivo. Hum Mol Genet. Aug. 1, 2017;26(15):2850-2863.

Bell, et al. Analysis of tumors arising in male B6C3F1 mice with and without AAV vector delivery to liver. Mol Ther. Jul. 2006;14(1):34-44.

Bell, et al. Motor neuron transduction after intracisternal delivery of AAV9 in a cynomolgus macaque. Hum Gene Ther Methods. Apr. 2015;26(2):43-4.

Bell, et al. No evidence for tumorigenesis of AAV vectors in a large-scale study in mice. Mol Ther. Aug. 2005;12(2):299-306.

Bevan et al. Systemic gene delivery in large species for targeting spinal cord, brain, and peripheral tissues for pediatric disorders. Mol Ther. Nov. 2011;19(11):1971-80.

Bolon, et al. STP position paper: Recommended practices for sampling and processing the nervous system (brain, spinal cord, nerve, and eye) during nonclinical general toxicity studies. Toxicol Pathol. 2013;41(7):1028-48.

Boxer et al. Frontotemporal degeneration, the next therapeutic frontier: molecules and animal models for frontotemporal degeneration drug development. Alzheimers Dement. Mar. 2013;9(2):176-88.

Bryant et al. Lessons learned from the clinical development and market authorization of Glybera. Hum Gene Ther Clin Dev. Jun. 2013;24(2):55-64.

Bucher, et al. Intracisternal delivery of AAV9 results in oligodendrocyte and motor neuron transduction in the whole central nervous system of cats. Gene Ther. May 2014;21(5):522-8.

Buning, et al. Recent developments in adeno-associated virus vector technology. J Gene Med. Jul. 2008;10(7):717-33.

Calcedo, et al. Worldwide epidemiology of neutralizing antibodies to adeno-associated viruses. J Infect Dis. Feb. 1, 2009;199(3):381-90.

Cash, et al. Patterns of gray matter atrophy in genetic frontotemporal dementia: results from the GENFI study. Neurobiol Aging. Feb. 2018;62:191-196.

Castle, et al. Long-distance axonal transport of AAV9 is driven by dynein and kinesin-2 and is trafficked in a highly motile Rab7-positive compartment. Mol Ther. Mar. 2014;22(3):554-566.

Caswell, et al. Genetic predictors of survival in behavioral variant frontotemporal degeneration. Neurology. Oct. 29, 2019;93(18):e1707-e1714. Epub Sep. 19, 2019.

Chandler, et al. Vector design influences hepatic genotoxicity after adeno-associated virus gene therapy. J Clin Invest. Feb. 2015;125(2):870-80.

Chen-Plotkin, et al. Genetic and clinical features of progranulin-associated frontotemporal lobar degeneration. Arch Neurol. Apr. 2011;68(4):488-97.

Ciesielska, et al. Cerebral infusion of AAV9 vector-encoding non-self proteins can elicit cell-mediated immune responses. Mol Ther. Jan. 2013;21(1):158-66.

Colle, et al. Efficient intracerebral delivery of AAV5 vector encoding human ARSA in non-human primate. Hum Mol Genet. Jan. 1, 2010;19(1):147-58.

Couto, et al. Direct exposure of mouse spermatozoa to very high concentrations of a serotype-2 adeno-associated virus gene therapy vector fails to lead to germ cell transduction. Hum Gene Ther. Mar. 2004;15(3):287-91.

Coyle-Gilchrist, et al. Prevalence, characteristics, and survival of frontotemporal lobar degeneration syndromes. Neurology. May 3, 2016;86(18):1736-43.

Dekaban, et al. Changes in brain weights during the span of human life: relation of brain weights to body heights and body weights. Ann Neurol. Oct. 1978;4(4):345-56.

Dindot, et al. Intrathecal injection of helper-dependent adenoviral vectors results in long-term transgene expression in neuroependymal cells and neurons. Hum Gene Ther. Jun. 2011;22(6):745-51.

Dirren, et al. Intracerebroventricular injection of adeno-associated virus 6 and 9 vectors for cell type-specific transgene expression in the spinal cord. Hum Gene Ther. Feb. 2014;25(2):109-20.

Donsante, et al. Observed incidence of tumorigenesis in long-term rodent studies of rAAV vectors. Gene Ther. Sep. 2001;8(17):1343-6.

Double, et al. The comparative biology of neuromelanin and lipofuscin in the human brain. Cell Mol Life Sci. Jun. 2008;65(11):1669-82.

(56) References Cited

OTHER PUBLICATIONS

Ellinwood, et al. Safe, efficient, and reproducible gene therapy of the brain in the dog models of Sanfilippo and Hurler syndromes. Mol Ther. Feb. 2011;19(2):251-9.

Federici, et al. Robust spinal motor neuron transduction following intrathecal delivery of AAV9 in pigs. Gene Ther. Aug. 2012;19(8):852-9.

Ferla, et al. Non-clinical safety and efficacy of an AAV2/8 vector administered intravenously for treatment of Mucopolysaccharidosis Type VI. Mol Ther Methods Clin Dev. Jul. 24, 2017;6:143-158.

Filiano AJ, et al. Dissociation of frontotemporal dementia-related deficits and neuroinflammation in progranulin haploinsufficient mice. J Neurosci. Mar. 20, 2013;33(12):5352-61.

Finch, et al. TMEM106B regulates progranulin levels and the penetrance of FTLD in GRN mutation carriers. Neurology. Feb. 1, 2011;76(5):467-74.

Foust, et al. Intravascular AAV9 preferentially targets neonatal neurons and adult astrocytes. Nat Biotechnol. Jan. 2009;27(1):59-65.

Fumagalli, et al. Distinct patterns of brain atrophy in Genetic Frontotemporal Dementia Initiative (GENFI) cohort revealed by visual rating scales. Alzheimers Res Ther. May 24, 2018;10(1):46.

Galimberti, et al. Progranulin plasma levels predict the presence of GRN mutations in asymptomatic subjects and do not correlate with brain atrophy: results from the GENFI study. Neurobiol Aging. Feb. 2018;62:245.e9-245.e12.

Gao, et al. Adeno-associated viruses undergo substantial evolution in primates during natural infections. Proc Natl Acad Sci U S A. May 13, 2003;100(10):6081-6.

Gao, et al. Clades of Adeno-associated viruses are widely disseminated in human tissues. J Virol. Jun. 2004;78(12):6381-8.

Gasca-Salas, et al. Characterization of movement disorder phenomenology in genetically proven, familial Frontotemporal Lobar Degeneration: A systematic review and meta-analysis. PLoS One. Apr. 21, 2016;11(4):e0153852.

Gass, et al. Mutations in progranulin are a major cause of ubiquitin-positive frontotemporal lobar degeneration. Hum Mol Genet. Oct. 15, 2006;15(20):2988-3001.

Ghoshal N, et al. Core features of frontotemporal dementia recapitulated in progranulin knockout mice. Neurobiol Dis. Jan. 2012;45(1):395-408.

Gil-Farina, et al. Recombinant AAV integration is not associated with hepatic genotoxicity in nonhuman primates and patients. Mol Ther. Jun. 2016;24(6):1100-1105.

Godel, et al. Human dorsal-root-ganglion perfusion measured in-vivo by MRI. Neuroimage. Nov. 1, 2016;141:81-87.

Gombash, et al. Systemic gene delivery transduces the enteric nervous system of guinea pigs and cynomolgus macaques. Gene Ther. Oct. 2017;24(10):640-648.

Gorno-Tempini, et al. Classification of primary progressive aphasia and its variants. Neurology. Mar. 15, 2011; 76(11): 1006-1014.

Gotzl, et al. Common pathobiochemical hallmarks of progranulin-associated frontotemporal lobar degeneration and neuronal ceroid lipofuscinosis. Acta Neuropathol. 2014;127(6):845-60.

Goyal. Lipofuscin pigment accumulation in human brain during aging. Exp Gerontol. 1982;17(6):481-7.

Graham et al. Characteristics of a human cell line transformed by DNA from human adenovirus type 5. J Gen Virol. Jul. 1977;36(1):59-74.

Gray, et al. Preclinical differences of intravascular AAV9 delivery to neurons and glia: a comparative study of adult mice and nonhuman primates. Mol Ther. Jun. 2011;19(6):1058-69.

Gray, et al. Global CNS gene delivery and evasion of anti-AAV-neutralizing antibodies by intrathecal AAV administration in non-human primates. Gene Ther. Apr. 2013;20(4):450-9.

Greig, et al. Non-clinical study examining AAV8.TBG.hLDLR vector-associated toxicity in chow-fed wild-type and LDLR(+/−) Rhesus macaques. Hum Gene Ther Clin Dev. Mar. 2017;28(1):39-50.

Grieger and Samulski. Adeno-associated virus as a gene therapy vector: vector development, production and clinical applications. Adv Biochem Eng Biotechnol. 2005;99:119-45.

Gu, et al. Absence of PTHrP nuclear localization and carboxyl terminus sequences leads to abnormal brain development and function. PLoS One. 2012;7(7):e41542.

Gurda, et al. Evaluation of AAV-mediated gene therapy for central nervous system disease in canine mucopolysaccharidosis VII. Mol Ther. Feb. 2016; 24(2): 206-216.

Haurigot, et al. Whole body correction of mucopolysaccharidosis IIIA by intracerebrospinal fluid gene therapy. J Clin Invest. Aug. 1, 2013;123(8):3254-3271.

Herndon, et al. Brain weight does not decrease with age in adult rhesus monkeys.Neurobiol Aging. May-Jun. 1998;19(3):267-72.

Hinderer et al., Adeno-associated virus serotype 1-based gene therapy for FTD caused by GRN mutations, Ann Clin Transl Neurol. Oct. 2020; 7(10): 1843-1853.

Hinderer, et al. Delivery of an adeno-associated virus vector into cerebrospinal fluid attenuates central nervous system disease in Mucopolysaccharidosis Type II mice. Hum Gene Ther. Nov. 2016;27(11):906-915.

Hinderer, et al. Neonatal systemic AAV induces tolerance to CNS gene therapy in MPS I dogs and nonhuman primates. Mol Ther. Aug. 2015;23(8):1298-1307.

Hinderer, et al. Severe Toxicity in Nonhuman Primates and Piglets Following High-Dose Intravenous Administration of an Adeno-Associated Virus Vector Expressing Human SMN. Hum Gene Ther. Mar. 2018;29(3):285-298.

Hinderer, et al. Evaluation of intrathecal routes of administration for adeno-associated viral vectors in large animals. Hum Gene Ther. Jan. 2018;29(1):15-24.

Hinderer, et al. Intrathecal gene therapy corrects CNS pathology in a feline model of mucopolysaccharidosis I. Mol Ther. Dec. 2014; 22(12): 2018-2027.

Hinderer, et al. Widespread gene transfer in the central nervous system of cynomolgus macaques following delivery of AAV9 into the cisterna magna. Mol Ther Methods. Dec. 10, 2014;1:14051.

Hoglinger, et al. Clinical diagnosis of progressive supranuclear palsy: The movement disorder society criteria. Mov Disord. Jun. 2017;32(6):853-864.

Hordeaux, et al. Toxicology study of intra-cisterna magna adeno-associated virus 9 expressing human alpha-L-iduronidase in rhesus macaques. Mol Ther Methods Clin Dev. Jul. 14, 2018;10:79-88.

Hordeaux, et al. Toxicology study of intra-cisterna magna adeno-associated virus 9 expressing iduronate-2-sulfatase in Rhesus macaques. Ther Methods Clin Dev. Jul. 14, 2018;10:68-78.

Hu, et al. Sortilin-mediated endocytosis determines levels of the frontotemporal dementia protein, progranulin. Neuron. Nov. 18, 2010;68(4):654-67.

Hudry, et al. Efficient gene transfer to the central nervous system by single-stranded Anc80L65. Mol Ther. Jul. 23, 2018;10:197-209.

Jakob, et al. No evidence for germ-line transmission following prenatal and early postnatal AAV-mediated gene delivery. J Gene Med. May 2005;7(5):630-7.

Janson, et al. Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.

Kaplitt, et al. Safety and tolerability of gene therapy with an adeno-associated virus (AAV) borne GAD gene for Parkinson's disease: an open label, phase I trial. Lancet. Jun. 2, 20073;369(9579):2097-105.

Katz, et al. Standardized method for intra-cisterna magna delivery under fluoroscopic guidance in nonhuman primates. Hum Gene Ther Methods. Oct. 2018;29(5):212-219.

Kay, et al. Evidence for gene transfer and expression of factor IX in haemophilia B patients treated with an AAV vector. Nat Genet. Mar. 2000;24(3):257-61.

Klein, et al. Loss of TMEM106B ameliorates lysosomal and frontotemporal dementia-related phenotypes in progranulin-deficient mice. Neuron. Jul. 19, 2017;95(2):281-296.e6.

(56) References Cited

OTHER PUBLICATIONS

Knopman, et al. Estimating the number of persons with frontotemporal lobar degeneration in the US population. J Mol Neurosci. Nov. 2011;45(3):330-5.

Le Ber, et al. Phenotype variability in progranulin mutation carriers: a clinical, neuropsychological, imaging and genetic study. Brain. Mar. 2008;131(Pt 3):732-46.

Li, et al. Adeno-associated virus capsid antigen presentation is dependent on endosomal escape. J Clin Invest. Mar. 2013;123(3):1390-401.

Li, et al. Assessing the potential for AAV vector genotoxicity in a murine model. Blood. Mar. 24, 2011;117(12):3311-9.

Lock, et al., Absolute determination of single-stranded and self-complementary adeno-associated viral vector genome titers by droplet digital PCR. Hum Gene Ther Methods. Apr. 2014;25(2):115-25.

Lui, et al. Progranulin deficiency promotes circuit-specific synaptic pruning by microglia via complement activation. Cell. May 5, 2016;165(4):921-35.

Matsuwaki et al. Possible involvement of the cerebellum in motor-function impairment in progranulin-deficient mice. Neuroreport. Sep. 30, 2015;26(14):877-81.

McCarty, et al. Integration of adeno-associated virus (AAV) and recombinant AAV vectors. Annu Rev Genet. 2004;38:819-45.

McKhann, et al. The diagnosis of dementia due to Alzheimer's disease: recommendations from the National Institute on Aging-Alzheimer's Association workgroups on diagnostic guidelines for Alzheimer's disease. Alzheimers Dement. May 2011;7(3):263-9.

Meeter LH, et al. Progranulin Levels in Plasma and Cerebrospinal Fluid in Granulin Mutation Carriers. Dement Geriatr Cogn Dis Extra. Jul. 22, 2016;6(2):330-340.

Melnick, et al. Association of 20-millimicron particles with adenoviruses. J Bacteriol. Jul. 1965;90(1):271-4.

Mendell, et al. Single-Dose Gene-Replacement Therapy for Spinal Muscular Atrophy. N Engl J Med. Nov. 2, 2017;377(18):1713-1722.

Miller, et al. Glybera and the future of gene therapy in the European Union. Nat Rev Drug Discov. May 2012;11(5):419.

Mittermeyer, et al. Long-term evaluation of a phase 1 study of AADC gene therapy for Parkinson's disease. Hum Gene Ther. Apr. 2012;23(4):377-81.

Nathwani, et al. Adenovirus- associated virus vector-mediated gene transfer in hemophilia B. N Engl J Med. Dec. 22, 2011; 365:2357-2365.

NCBI Reference Sequence: NM_002087.3, *Homo sapiens* granulin precursor (GRN), mRNA, Feb. 17, 2019.

NCBI Reference Sequence: NP_002078.1, progranulin precursor [*Homo sapiens*], Feb. 17, 2019.

Onyike, et al. The Epidemiology of Frontotemporal Dementia. Int Rev Psychiatry. Apr. 2013; 25(2): 130-137.

Pardo, et al. Technical guide for nervous system sampling of the cynomolgus monkey for general toxicity studies. Toxicol Pathol. Jun. 2012;40(4):624-36.

Passage Bio, Inc. Press Release—Passage Bio Receives FDA Clearance of IND Application for PBFT02 Gene Therapy Candidate for Treatment of Patients with Frontotemporal Dementia with Granulin Mutations. Passage Bio Receives FDA Clearance of IND Application for PBFT02 Gene Therapy Candidate for Treatment of Patients with Frontotemporal Dementia with Granulin Mutations. Jan. 28, 2021.

Pellot JE, De Jesus O. Suboccipital Puncture. [Updated Jul. 31, 2021]. In: StatPearls [Internet]. Treasure Island (FL): StatPearls Publishing; Jan. 2021. Available from: https://www.ncbi.nlm.nih.gov/books/NBK560630/.

Penaud-Budloo, et al. Adeno-associated virus vector genomes persist as episomal chromatin in primate muscle. J Virol. Aug. 2008;82(16):7875-85.

Rangarajan, et al. AAV5-Factor VIII Gene Transfer in Severe Hemophilia A. N Engl J Med. Dec. 28, 2017;377(26):2519-2530. Epub Dec. 9, 2017.

Rascovsky, et al. Sensitivity of revised diagnostic criteria for the behavioural variant of frontotemporal dementia. Brain. Sep. 2011; 134(9): 2456-2477.

Ribera, et al. Biochemical, histological and functional correction of mucopolysaccharidosis type IIIB by intra-cerebrospinal fluid gene therapy. Hum Mol Genet. Apr. 1, 2015;24(7):2078-95.

Richards, et al. Standards and guidelines for the interpretation of sequence variants: a joint consensus recommendation of the American College of Medical Genetics and Genomics and the Association for Molecular Pathology. Genet Med. May 2015;17(5):405-24.

Rohrer, et al. Distinct profiles of brain atrophy in frontotemporal lobar degeneration caused by progranulin and tau mutations. Neuroimage. Nov. 15, 2010;53(3):1070-6.

Rohrer, et al. The heritability and genetics of frontotemporal lobar degeneration. Neurology. Nov. 3, 2009;73(18):1451-6.

Rosas, et al. Patterns of scAAV vector insertion associated with oncogenic events in a mouse model for genotoxicity. Mol Ther. Nov. 2012;20(11):2098-110.

Samaranch, et al. AAV9-mediated expression of a non-self protein in nonhuman primate central nervous system triggers widespread neuroinflammation driven by antigen-presenting cell transduction. Mol Ther. Feb. 2014;22(2):329-337.

Samaranch, et al. Strong cortical and spinal cord transduction after AAV7 and AAV9 delivery into the cerebrospinal fluid of nonhuman primates. Hum Gene Ther. May 2013;24(5):526-32.

Sardiello, et al. A gene network regulating lysosomal biogenesis and function. Science. Jul. 24, 2009;325(5939):473-7.

Schraen-Maschke, et al. Tau as a biomarker of neurodegenerative diseases. Biomark Med. Aug. 2008;2(4):363-84.

Schuster, et al. Biodistribution of adeno-associated virus serotype 9 (AAV9) vector after intrathecal and intravenous delivery in mouse. Front Neuroanat. 2014; 8: 42. Published online Jun. 10, 2014.

Settembre, et al. TFEB links autophagy to lysosomal biogenesis. Science. Jun. 17, 2011;332(6036):1429-33.

Siintola, et al. Cathepsin D deficiency underlies congenital human neuronal ceroid- lipofuscinosis. Brain. Jun. 2006;129(Pt 6):1438-45.

Smith, et al. Strikingly different clinicopathological phenotypes determined by progranulin-mutation dosage. Am J Hum Genet. Jun. 8, 2012;90(6):1102-7.

Snyder, et al. Comparison of adeno-associated viral vector serotypes for spinal cord and motor neuron gene delivery. Hum Gene Ther. Sep. 2011;22(9):1129-35.

Sommer et al., Quantification of adeno-associated virus particles and empty capsids by optical density measurement. Mol Ther. Jan. 2003;7(1):122-8.

Spassky, et al. Adult ependymal cells are postmitotic and are derived from radial glial cells during embryogenesis. J Neurosci. Jan. 5, 2005;25(1):10-8.

Tanaka, et al. Progranulin regulates lysosomal function and biogenesis through acidification of lysosomes. Hum Mol Genet. Mar. 1, 2017;26(5):969-988.

Tardieu, et al. Intracerebral administration of adeno-associated viral vector serotype rh.10 carrying human SGSH and SUMF1 cDNAs in children with mucopolysaccharidosis type IIIA disease: results of a phase I/II trial. Hum Gene Ther. Jun. 2014;25(6):506-16.

Tsai and Boxer. Therapy and clinical trials in frontotemporal dementia: past, present, and future. J Neurochem. Aug. 2016;138 Suppl 1(Suppl 1):211-21.

Van Damme, et al. Progranulin functions as a neurotrophic factor to regulate neurite outgrowth and enhance neuronal survival. J Cell Biol. Apr. 7, 2008;181(1):37-41.

Van Kampen et al., Progranulin gene delivery protects dopaminergic neurons in a mouse model of Parkinson's disease. PLoS One. May 7, 2014;9(5):e97032.

Vite, et al. Effective gene therapy for an inherited CNS disease in a large animal model. Ann Neurol. Mar. 2005;57(3):355-64.

Ward, et al. Individuals with progranulin haploinsufficiency exhibit features of neuronal ceroid lipofuscinosis. Sci Transl Med. Apr. 12, 2017;9(385):eaah5642.

Watakabe, et al. Comparative analyses of adeno-associated viral vector serotypes 1, 2, 5, 8 and 9 in marmoset, mouse and macaque cerebral cortex. Neurosci Res. Apr. 2015;93:144-57.

(56) References Cited

OTHER PUBLICATIONS

Whitwell, et al. Brain atrophy over time in genetic and sporadic frontotemporal dementia: a study of 198 serial magnetic resonance images. Eur J Neurol. May 2015;22(5):745-52.
Whitwell, et al. Trajectories of brain and hippocampal atrophy in FTD with mutations in MAPT or GRN. Neurology. Jul. 26, 2011; 77(4): 393-398.
Wils, et al. Cellular ageing, increased mortality and FTLD-TDP-associated neuropathology in progranulin knockout mice. J Pathol. Sep. 2012;228(1):67-76.
Wobus, et al. Monoclonal antibodies against the adeno-associated virus type 2 (AAV-2) capsid: epitope mapping and identification of capsid domains involved in AAV-2-cell interaction and neutralization of AAV-2 infection. J Virol. Oct. 2000;74(19):9281-93.
Woollacott and Rohrer. The clinical spectrum of sporadic and familial forms of frontotemporal dementia. J Neurochem. Aug. 2016;138 Suppl 1:6-31.
Worgall, et al. Treatment of late infantile neuronal ceroid lipofuscinosis by CNS administration of a serotype 2 adeno-associated virus expressing CLN2 cDNA. Hum Gene Ther. May 2008;19(5):463-74.
Xiao, et al. Gene therapy vectors based on adeno-associated virus type 1. J Virol. May 1999;73(5):3994-4003.
Yamazaki, et al. Targeted gene transfer into ependymal cells through intraventricular injection of AAV1 vector and long-term enzyme replacement via the CSF. Sci Rep. Jul. 1, 2014;4:5506.
Yin F, et al. Behavioral deficits and progressive neuropathology in progranulin-deficient mice: a mouse model of frontotemporal dementia. FASEB J. Dec. 2010;24(12):4639-47.
Zanta-Boussif, et al. Validation of a mutated PRE sequence allowing high and sustained transgene expression while abrogating WHV-X protein synthesis: application to the gene therapy of WAS. Gene Ther. May 2009;16(5):605-19.
Zhang, et al. Adenovirus-adeno-associated virus hybrid for large-scale recombinant adeno-associated virus production. Hum Gene Ther. Sep. 2009;20(9):922-9.
Zhang, et al. Tau Pathology in Parkinson's Disease. Front Neurol. 2018; 9: 809. Published online Oct. 2, 2018.
Zhou, et al. C-Terminus of Progranulin Interacts with the Beta-Propeller Region of Sortilin to Regulate Progranulin Trafficking. PLoS One. 2011; 6(6): e21023.
Zhou, et al. Decreased progranulin levels in patients and rats with subarachnoid hemorrhage: a potential role in inhibiting inflammation by suppressing neutrophil recruitment. J Neuroinflammation. Nov. 2, 2015;12:200.
Zhou, et al. Impaired prosaposin lysosomal trafficking in frontotemporal lobar degeneration due to progranulin mutations. Nat Commun. May 25, 2017;8:15277.
Zhou, et al. Prosaposin facilitates sortilin-independent lysosomal trafficking of progranulin. J Cell Biol. Sep. 14, 2015;210(6):991-1002.
International Search Report and Written Opinion issued for International Patent Application No. PCT/US2020/019149, mailed Jun. 17, 2020.
De Muynck, L., & Van Damme, P., The Development of Drug Therapies for Frontotemporal Dementia Caused by Progranulin Mutations. Frontiers in Clinical Drug Research—Alzheimer Disorders, May 2015, 3(5):231-291.
Gholizadeh et al., Transduction of the central nervous system after intracerebroventricular injection of adeno-associated viral vectors in neonatal and juvenile mice. Hum Gene Ther Methods. Aug. 2013;24(4):205-13. Epub Aug. 3, 2013.
Katz et al., AAV gene transfer delays disease onset in a TPP1-deficient canine model of the late infantile form of Batten disease. Sci Transl Med. Nov. 11, 2015;7(313):313ra180.
Minami et al., Progranulin protects against amyloid β deposition and toxicity in Alzheimer's disease mouse models. Nat Med. Oct. 2014;20(10):1157-64. Epub Sep. 28, 2014.
Neverman et al., Experimental therapies in the neuronal ceroid lipofuscinoses. Biochim Biophys Acta. Oct. 2015;1852(10 Pt B):2292-300. Epub May 6, 2015.
Bond et al., Use of model organisms for the study of neuronal ceroid lipofuscinosis, Biochim Biophys Acta, vol. 1832(11):1842-65, Nov. 2013.
Anderson et al., Human Pathology in NCL, Biochim Biophys Acta, vol. 1832(11):1087-26, Nov. 2013.
Xu et al., Extracellular progranulin protects cortical neurons from toxic insults by activating survival signaling, Neurobiology of Aging, vol. 32(12):2326.e5-16, Dec. 2011.
Yu et al., The Spectrum of Mutations in Progranulin: A Collaborative Study Screening 545 Cases of Neurodegeneration, Arch Neurology, vol. 67(2):161-170, Feb. 2010.
Gotz et al., Animal models for Alzheimer's disease and frontotemporal dementia: a perspective, ASN Neuro, vol. 1(4):e00019, Oct. 2009.
Simonato et al., Progress in gene therapy for neurological disorders, Nature Reviews, Neurology, vol. 9(5):227-91, May 2013.
Neary et al., Frontotemporal Dementia, Neurology, vol. 4(11):771-80, Nov. 2005.
Weber et al., Large Animal Models for Batten Disease: A Review, Journal of Child Neurology, vol. 28(9):1123-7, Sep. 2013.
Raitano et al., Restoration of Progranulin Expression Rescues Cortical Neuron Generation in an Induced Pluripotent Stem Cell Model of Frontotemporal Dementia, Stem Cell Reports, vol. 4(1):16-24, Jan. 2015.
Hironaka K, et al. Enzyme replacement in the CSF to treat metachromatic leukodystrophy in mouse model using single intracerebroventricular injection of self-complementary AAV1 vector. Sci Rep. Aug. 18, 2015;5:13104. 12 pages.
Kurai T, Shimada T. Recombinant adeno-associated virus-mediated gene delivery to the central nervous system. J Nippon Med Sch. Jun. 2007;74(3):188-9.
Mandel, et al. Clinical trials in neurological disorders using AAV vectors: promises and challenges. Curr Opin Mol Ther. Oct. 2004;6(5):482-90.
International Search Report and Written Opinion issued for International Patent Application No. PCT/US2021/047686, mailed Jan. 4, 2022.
Gonzalez-Perez O. Neural stem cells in the adult human brain. Biol Biomed Rep. 2012;2(1):59-69.
Non-Final Office Action issued in U.S. Appl. No. 16/081,346, dated Sep. 16, 2020, and Response filed Dec. 11, 2020.
Final Office Action issued in U.S. Appl. No. 16/081,346, dated Apr. 19, 2021 and Response filed Jul. 19, 2021.
Non-Final Office Action issued in U.S. Appl. No. 16/081,346, dated Sep. 7, 2021, and Response filed Dec. 23, 2021.
Final Office Action issued in U.S. Appl. No. 16/081,346, dated Apr. 5, 2022, and Response filed Jul. 28, 2022.
Non-Final Office Action issued in corresponding U.S. Appl. No. 16/081,346, dated Dec. 6, 2022, and Response filed May 31, 2023.
Final Office Action issued in corresponding U.S. Appl. No. 16/081,346, dated Sep. 14, 2023.

\* cited by examiner

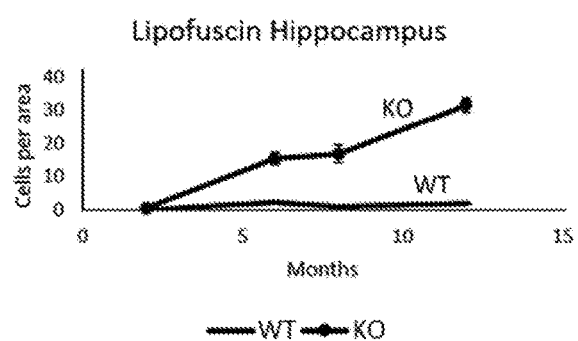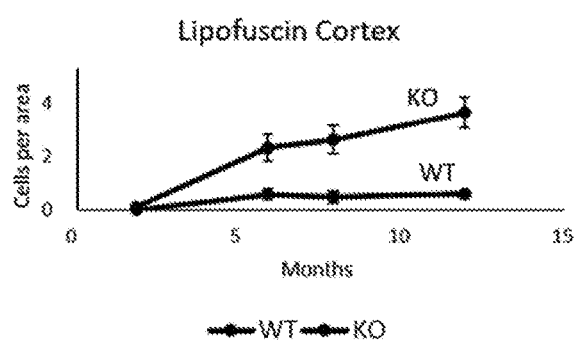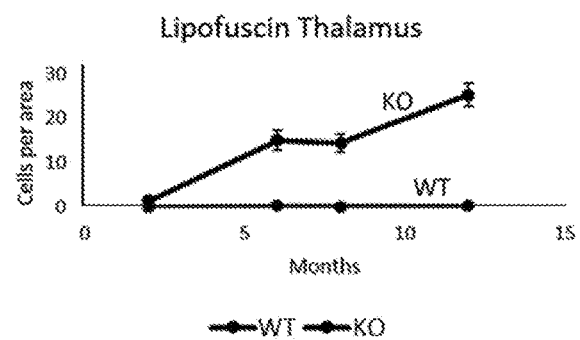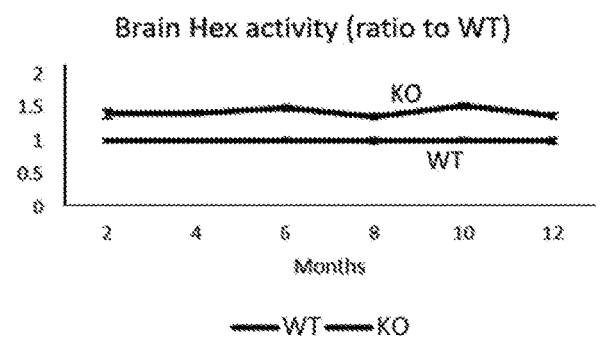

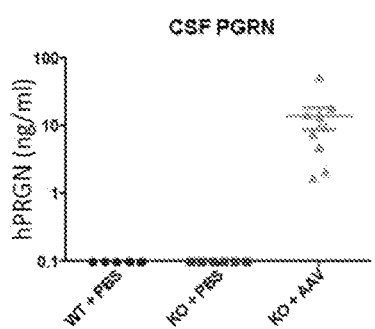
FIG. 4A
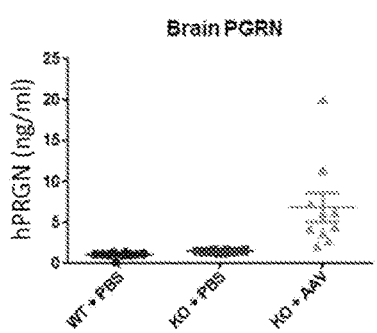
FIG. 4B
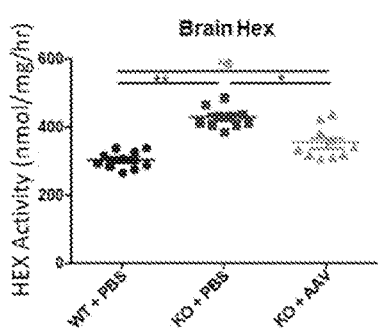
FIG. 4C
FIG. 4D
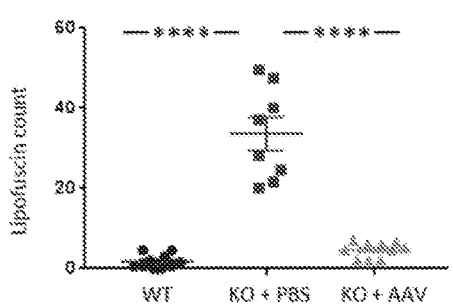
FIG. 4G
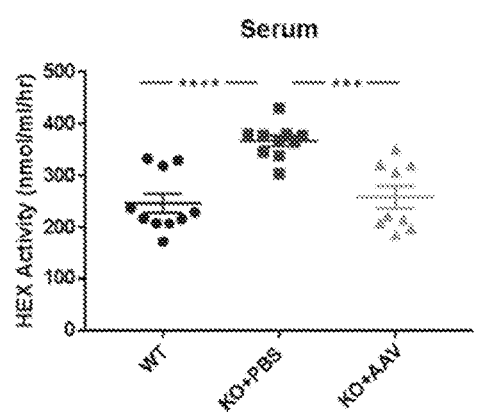
FIG. 4E
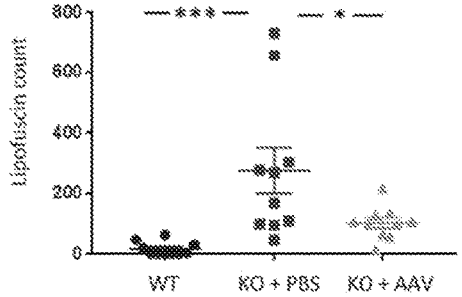
FIG. 4F
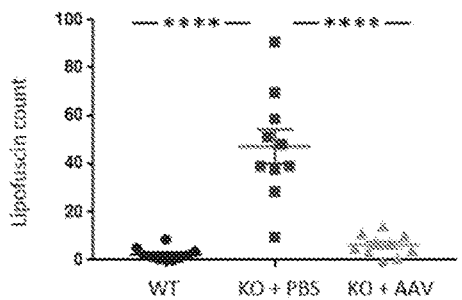

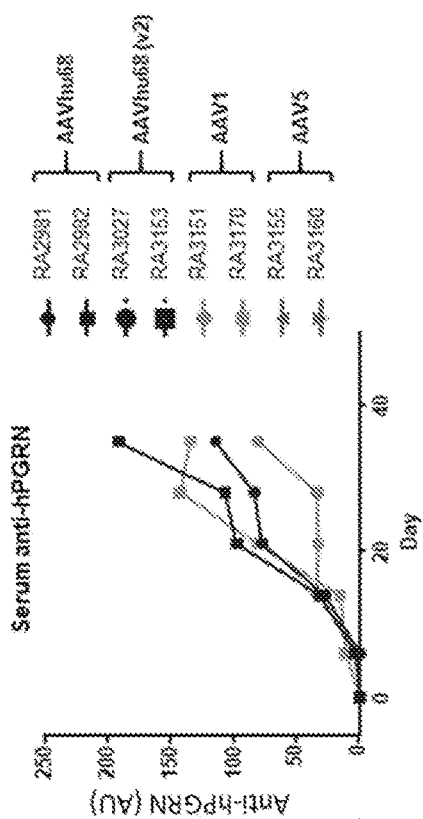
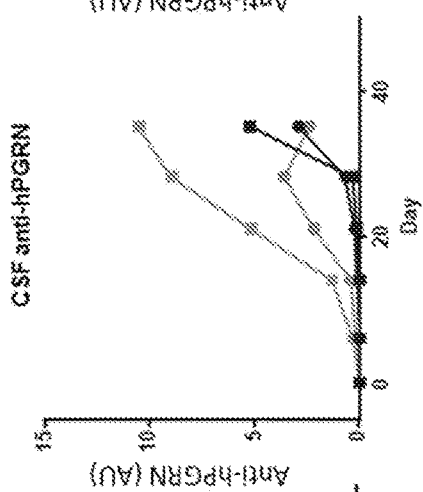
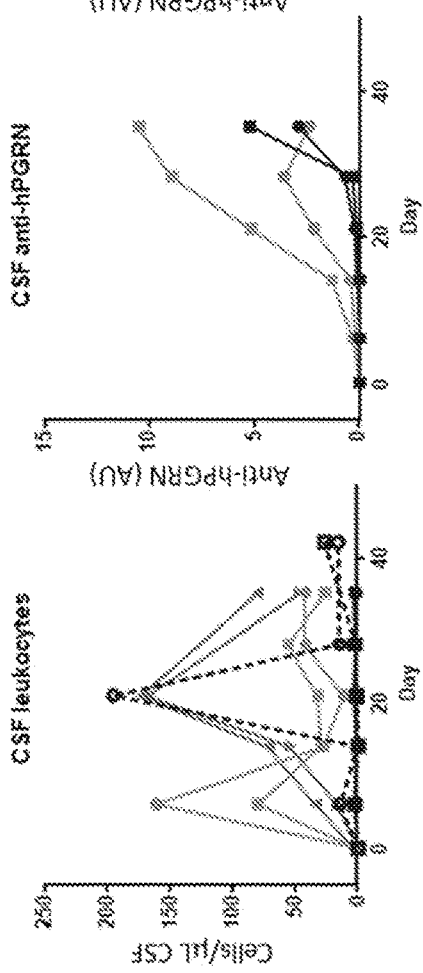

FIG. 10

| Cell marker | Animal ID | Region | | | | | Average |
|---|---|---|---|---|---|---|---|
| | | 1 | 2 | 3 | 4 | 5 | |
| NeuN | 1518 | 0.13 | N/A | 0.205 | 0.34 | 0.167 | 0.049 | 0.178 |
| | 2076 | 0.106 | 0.227 | 0.258 | 0.528 | 0.053 | N/A | 0.234 |
| | 1826 | 0.1 | 0.318 | 0.195 | 0.202 | 0.171 | N/A | 0.197 |
| | 2068 | 0.218 | N/A | 0.153 | 0.141 | 0.128 | 0.065 | 0.141 |
| GFAP | 1518 | 0.152 | N/A | 0.202 | 0.914 | 0.39 | 0.476 | 0.427 |
| | 2076 | 0.011 | 0.064 | 0.235 | 0.511 | 0.011 | N/A | 0.166 |
| | 1826 | 0.019 | 0.013 | 0.021 | 0.244 | 0.007 | N/A | 0.061 |
| | 2068 | 0.066 | N/A | 0.245 | 0.13 | 0.459 | 0.33 | 0.246 |
| Olig2 | 1518 | 0.02 | N/A | 0.03 | 0.04 | 0.009 | 0.023 | 0.024 |
| | 2076 | 0.02 | 0.023 | 0.011 | 0.013 | 0.013 | N/A | 0.016 |
| | 1826 | 0 | 0.001 | 0.008 | 0.016 | N/A | 0.001 | 0.005 |
| | 2068 | 0.002 | 0 | N/A | 0.001 | 0.002 | 0.002 | 0.001 |

```
                         SEQUENCE LISTING

<160> NUMBER OF SEQ ID NOS: 35

<210> SEQ ID NO 1
<211> LENGTH: 593
<212> TYPE: PRT
<213> ORGANISM: Homo sapiens

<400> SEQUENCE: 1

Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270
```

```
Lys Leu Pro Ala His Thr Val Gly Asp Val Lys Cys Asp Met Glu Val
            275                 280                 285

Ser Cys Pro Asp Gly Tyr Thr Cys Cys Arg Leu Gln Ser Gly Ala Trp
        290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
                340                 345                 350

Ser Leu Pro Asp Pro Gln Ala Leu Lys Arg Asp Val Pro Cys Asp Asn
            355                 360                 365

Val Ser Ser Cys Pro Ser Ser Asp Thr Cys Cys Gln Leu Thr Ser Gly
370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Ala Ser Leu Ser His Pro Arg Asp Ile Gly Cys Asp Gln His Thr
        435                 440                 445

Ser Cys Pro Val Gly Gln Thr Cys Cys Pro Ser Leu Gly Gly Ser Trp
    450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Glu Gly His Phe Cys His
        515                 520                 525

Asp Asn Gln Thr Cys Cys Arg Asp Asn Arg Gln Gly Trp Ala Cys Cys
530                 535                 540

Pro Tyr Arg Gln Gly Val Cys Cys Ala Asp Arg Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
            580                 585                 590

Leu

<210> SEQ ID NO 2
<211> LENGTH: 1782
<212> TYPE: DNA
<213> ORGANISM: Homo sapiens

<400> SEQUENCE: 2
atgtggaccc tggtgagctg ggtggcctta acagcagggc tggtggctgg aacgcggtgc      60
ccagatggtc agttctgccc tgtggcctgc tgcctggacc ccggaggagc cagctacagc     120
tgctgccgtc cccttctgga caaatggccc acaacactga gcaggcatct gggtggcccc     180
tgccaggttg atgccactg ctctgccggc cactcctgca tctttaccgt ctcagggact     240
tccagttgct gccccttccc agaggccgtg gcatgcgggg atggccatca ctgctgccca     300
```

```
cggggcttcc actgcagtgc agacgggcga tcctgcttcc aaagatcagg taacaactcc     360
gtgggtgcca tccagtgccc tgatagtcag ttcgaatgcc cggacttctc cacgtgctgt     420
gttatggtcg atggctcctg ggggtgctgc cccatgcccc aggcttcctg ctgtgaagac     480
agggtgcact gctgtccgca cggtgccttc tgcgacctgg ttcacacccg ctgcatcaca     540
cccacgggca cccacccccct ggcaaagaag ctccctgccc agaggactaa cagggcagtg    600
gccttgtcca gctcggtcat gtgtccggac gcacggtccc ggtgccctga tggttctacc     660
tgctgtgagc tgcccagtgg gaagtatggc tgctgcccaa tgcccaacgc cacctgctgc     720
tccgatcacc tgcactgctg cccccaagac actgtgtgtg acctgatcca gagtaagtgc     780
ctctccaagg agaacgctac cacggacctc ctcactaagc tgcctgcgca cacagtgggg     840
gatgtgaaat gtgacatgga ggtgagctgc ccagatgggt ataccctgctg ccgtctacag     900 tcgggggcct ggggctgctg ccctttttacc caggctgtgt gctgtgagga ccacatacac     960
tgctgtcccg cggggtttac gtgtgacacg cagaagggta cctgtgaaca ggggcccccac    1020 caggtgccct ggatggagaa ggccccagct cacctcagcc tgccagaccc acaagccttg    1080
aagagagatg tcccctgtga taatgtcagc agctgtccct cctccgatac ctgctgccaa    1140
ctcacgtctg gggagtgggg ctgctgtcca atcccagagg ctgtctgctg ctcggaccac    1200
cagcactgct gcccccaggg ctacacgtgt gtagctgagg ggcagtgtca gcaggaagc    1260 gagatcgtgg ctggactgga gaagatgcct gcccgccggg cttccttatc ccaccccaga    1320
gacatcggct gtgaccagca caccagctgc cggtggggc agacctgctg cccgagcctg    1380
ggtgggagct gggcctgctg ccagttgccc catgctgtgt gctgcgagga tcgccagcac    1440
tgctgcccgg ctggctacac ctgcaacgtg aaggctcgat cctgcgagaa ggaagtggtc    1500
tctgcccagc ctgccacctt cctggcccgt agccctcacg tgggtgtgaa ggacgtggag    1560 tgtgggggaag acacttctg ccatgataac cagacctgct gccgagacaa ccgacagggc    1620
tgggcctgct gtccctaccg ccagggcgtc tgttgtgctg atcggcgcca ctgctgtcct    1680
gctggcttcc gctgcgcagc caggggtacc aagtgtttgc gcagggaggc cccgcgctgg    1740 gacgccccctt tgagggaccc agccttgaga cagctgctgt ga                      1782
```

<210> SEQ ID NO 3
<211> LENGTH: 1785
<212> TYPE: DNA
<213> ORGANISM: Artificial sequence
<220> FEATURE:
<223> OTHER INFORMATION: Engineered human PRGN1 coding sequence

<400> SEQUENCE: 3

```
atgtggaccc tggtgtcttg ggttgcactg acagctggac tggtggccgg cacaagatgt      60
cctgacggcc agttttgccc cgtggcctgc tgtcttgatc ctggcggagc cagctacagc     120
tgctgcagac ctctgctgga taagtggccc accacactga gcagacacct cggaggacct     180
tgtcaggtgg acgcccactg ttctgccgga cacagctgca tctttaccgt gtctggcacc     240
tccagctgct gtccatttcc tgaggctgtg gcctgcggag acggccacca ctgttgtcct     300
agaggcttcc actgtagcgc cgacggcaga agctgctttc agagaagcgg caacaatagc     360
gtgggcgcca tccagtgtcc tgacagccag ttcgagtgcc ccgacttcag cacctgttgc     420
gtgatggtgg acggcagctg ggctgttgt ccaatgcctc aggctagctg ctgcgaggac     480
agagtgcact gttgccctca cggcgccttt tgcgatctgg tgcacacccg tgcatcacc     540
```

```
ccaacaggca cacatcctct ggccaagaag ctgcctgctc agcggaccaa tagagccgtg    600
gctctgagca gcagcgtgat gtgccctgac gccagatcca ggtgtccaga cggctccaca    660
tgttgcgaac tgcccagcgg caaatacggc tgctgcccca tgcctaacgc cacatgctgt    720
agcgaccatc ttcactgctg cccacaagac accgtgtgcg acctgatcca gagcaagtgc    780
ctgagcaaag agaacgccac caccgacctg ctgaccaaac tgccagctca ccgtgggga    840
gatgtgaagt gcgacatgga agtgtcttgc cccgacggct ataccctgct agactgcaa    900
tctggcgcct ggggctgctg ccctttaca caagctgtgt gttgcgagga ccacatccat    960
tgctgccctg ccggcttcac ctgtgacaca cagaaaggca cctgcgagca gggccctcat   1020
caggtgccat ggatggaaaa agcccctgct cacctgagcc tgcctgatcc tcaagctctg   1080
aagagggacg tgccctgcga caatgtgtct agctgcccta gcagcgacac ctgctgccag   1140
ctgacatctg gcgagtgggg ctgctgtcct ataccagagg ccgtgtgttg ttccgaccac   1200
cagcattgct gtccccaagg ctacacctgt gtggccgaag ccaatgtca cggggctct    1260
gaaattgtgg ccgcctgga aaagatgccc gccagaaggg cttctctgtc tcaccccgg    1320
gacatcggct cgaccagca cacatcttgt cctgtgggcc agacctgttg tcctctctt    1380
ggtggatcct gggcttgctg tcagctgcct cacgccgtgt gctgcgaaga tagacaaac   1440
tgctgtcccg ccggatacac ctgtaacgtg aaggccagat cctgcgagaa agaagtggtg   1500
tctgcccagc ctgccacctt cctggctaga agtcctcacg tgggcgtgaa ggacgtggag   1560
tgtggcgagg ccacttctg ccacgacaat cagacatgct gcagagacaa ccggcaaggc    1620
tgggcttgtt gcccatatag acagggcgtg tgctgtgccg acagaaggca ctgttgtcca   1680
gccggcttta gatgtgccgc caggggcaca aagtgtctga aagggaagc ccctaggtgg    1740
gacgcccctc tgagagatcc tgctctgaga cagctgctct gatga                  1785

<210> SEQ ID NO 4
<211> LENGTH: 1779
<212> TYPE: DNA
<213> ORGANISM: Artificial sequence
<220> FEATURE:
<223> OTHER INFORMATION: engineered hPRGN2 coding sequence
<220> FEATURE:
<221> NAME/KEY: CDS
<222> LOCATION: (1)..(1779)

<400> SEQUENCE: 4 atg tgg acc ctg gtt agc tgg gtg gcc ctg acc gcc ggc ctg gtg gcc    48
Met Trp Thr Leu Val Ser Trp Val Ala Leu Thr Ala Gly Leu Val Ala
1               5                   10                  15 ggc acc agg tgc ccc gac ggc cag ttc tgc ccc gtg gcc tgc tgc ctg    96
Gly Thr Arg Cys Pro Asp Gly Gln Phe Cys Pro Val Ala Cys Cys Leu
            20                  25                  30 gac ccc ggc ggc gcc agc tac agc tgc tgc aga ccc ctg ctg gac aag   144
Asp Pro Gly Gly Ala Ser Tyr Ser Cys Cys Arg Pro Leu Leu Asp Lys
        35                  40                  45 tgg ccc acc acc ctg agc aga cac ctg ggc ggc ccc tgc cag gtg gac   192
Trp Pro Thr Thr Leu Ser Arg His Leu Gly Gly Pro Cys Gln Val Asp
    50                  55                  60 gcc cac tgc agc gcc ggc cac agc tgc atc ttc acc gtg agc ggc acc   240
Ala His Cys Ser Ala Gly His Ser Cys Ile Phe Thr Val Ser Gly Thr
65                  70                  75                  80 agc agc tgc tgc ccc ttc ccc gag gcc gtg gcc tgc ggc gac ggc cac   288
Ser Ser Cys Cys Pro Phe Pro Glu Ala Val Ala Cys Gly Asp Gly His
                85                  90                  95
```

-continued

| | | |
|---|---|---|
| cac tgc tgc ccc aga ggc ttc cac tgc agc gcc gac ggc aga agc tgc<br>His Cys Cys Pro Arg Gly Phe His Cys Ser Ala Asp Gly Arg Ser Cys<br>100                          105                    110 | 336 |
| ttc cag aga agc ggc aac aac agc gtg ggc gcc atc cag tgc ccc gac<br>Phe Gln Arg Ser Gly Asn Asn Ser Val Gly Ala Ile Gln Cys Pro Asp<br>115                          120                    125 | 384 |
| agc cag ttc gag tgc ccc gac ttc agc acc tgc tgc gtg atg gtg gac<br>Ser Gln Phe Glu Cys Pro Asp Phe Ser Thr Cys Cys Val Met Val Asp<br>130                          135                    140 | 432 |
| ggc agc tgg ggc tgc tgc ccc atg ccc cag gcc agc tgc tgc gag gac<br>Gly Ser Trp Gly Cys Cys Pro Met Pro Gln Ala Ser Cys Cys Glu Asp<br>145                          150                    155                    160 | 480 |
| aga gtg cac tgc tgc ccc cac ggc gcc ttc tgc gac ctg gtg cac acc<br>Arg Val His Cys Cys Pro His Gly Ala Phe Cys Asp Leu Val His Thr<br>                          165                    170                    175 | 528 |
| agg tgc atc acc ccc acc ggc acc cac ccc ctg gcc aag aag ctg ccc<br>Arg Cys Ile Thr Pro Thr Gly Thr His Pro Leu Ala Lys Lys Leu Pro<br>                    180                    185                    190 | 576 |
| gcc cag aga acc aac aga gcc gtg gcc ctg agc agc agc gtg atg tgc<br>Ala Gln Arg Thr Asn Arg Ala Val Ala Leu Ser Ser Ser Val Met Cys<br>195                          200                    205 | 624 |
| ccc gac gcc aga agc agg tgc ccc gac ggc agc acc tgc tgc gag ctg<br>Pro Asp Ala Arg Ser Arg Cys Pro Asp Gly Ser Thr Cys Cys Glu Leu<br>210                          215                    220 | 672 |
| ccc agc ggc aag tac ggc tgc tgc ccc atg ccc aac gcc acc tgc tgc<br>Pro Ser Gly Lys Tyr Gly Cys Cys Pro Met Pro Asn Ala Thr Cys Cys<br>225                          230                    235                    240 | 720 |
| agc gac cac ctg cac tgc tgc ccc caa gac acc gtg tgc gac ctg atc<br>Ser Asp His Leu His Cys Cys Pro Gln Asp Thr Val Cys Asp Leu Ile<br>                          245                    250                    255 | 768 |
| cag agc aag tgc ctg agc aag gag aac gcc acc acc gac ctg ctg acc<br>Gln Ser Lys Cys Leu Ser Lys Glu Asn Ala Thr Thr Asp Leu Leu Thr<br>                    260                    265                    270 | 816 |
| aag ctg ccc gcc cac acc gtg ggc gac gtg aag tgc gac atg gag gtt<br>Lys Leu Pro Ala His Thr Val Gly Asp Val Lys Cys Asp Met Glu Val<br>275                          280                    285 | 864 |
| agc tgt ccc gac ggc tac acc tgc tgc aga ctg cag agc ggc gcc tgg<br>Ser Cys Pro Asp Gly Tyr Thr Cys Cys Arg Leu Gln Ser Gly Ala Trp<br>290                          295                    300 | 912 |
| ggc tgc tgc ccc ttc acc caa gcc gtg tgc tgc gag gac cac atc cac<br>Gly Cys Cys Pro Phe Thr Gln Ala Val Cys Cys Glu Asp His Ile His<br>305                          310                    315                    320 | 960 |
| tgc tgc ccc gcc ggc ttc acc tgc gac acc cag aag ggc acc tgc gag<br>Cys Cys Pro Ala Gly Phe Thr Cys Asp Thr Gln Lys Gly Thr Cys Glu<br>                          325                    330                    335 | 1008 |
| cag ggc ccc cac cag gtg ccc tgg atg gag aag gcc ccc gcc cac ctg<br>Gln Gly Pro His Gln Val Pro Trp Met Glu Lys Ala Pro Ala His Leu<br>                    340                    345                    350 | 1056 |
| agc ctg ccc gac ccc cag gcc ctg aag aga gac gtg ccc tgc gac aac<br>Ser Leu Pro Asp Pro Gln Ala Leu Lys Arg Asp Val Pro Cys Asp Asn<br>355                          360                    365 | 1104 |
| gtt agc agc tgc ccc agc agc gac acc tgc tgc cag ctg acc agc ggc<br>Val Ser Ser Cys Pro Ser Ser Asp Thr Cys Cys Gln Leu Thr Ser Gly<br>370                          375                    380 | 1152 |
| gag tgg ggc tgc tgc ccc atc ccc gag gcc gtg tgc tgc agc gac cac<br>Glu Trp Gly Cys Cys Pro Ile Pro Glu Ala Val Cys Cys Ser Asp His<br>385                          390                    395                    400 | 1200 |
| cag cac tgc tgc ccc caa ggc tac acc tgc gtg gcc gag ggc cag tgc<br>Gln His Cys Cys Pro Gln Gly Tyr Thr Cys Val Ala Glu Gly Gln Cys<br>                          405                    410                    415 | 1248 |

```
cag aga ggc agc gag atc gtg gcc ggc ctg gag aag atg ccc gcc aga    1296
Gln Arg Gly Ser Glu Ile Val Ala Gly Leu Glu Lys Met Pro Ala Arg
            420                 425                 430 aga gcc agc ctg agc cac ccc aga gac atc ggc tgc gac cag cac acc    1344
Arg Ala Ser Leu Ser His Pro Arg Asp Ile Gly Cys Asp Gln His Thr
        435                 440                 445 agc tgc ccc gtg ggc cag acc tgc tgc ccc agc ctg ggc ggc agc tgg    1392
Ser Cys Pro Val Gly Gln Thr Cys Cys Pro Ser Leu Gly Gly Ser Trp
    450                 455                 460 gcc tgc tgc cag ctg ccc cac gcc gtg tgc tgc gag gac aga cag cac    1440
Ala Cys Cys Gln Leu Pro His Ala Val Cys Cys Glu Asp Arg Gln His
465                 470                 475                 480 tgc tgc ccc gcc ggc tac acc tgc aac gtg aag gcc aga agc tgc gag    1488
Cys Cys Pro Ala Gly Tyr Thr Cys Asn Val Lys Ala Arg Ser Cys Glu
                485                 490                 495 aag gag gtg gtg agc gcc cag ccc gcc acc ttc ctg gcc aga agc ccc    1536
Lys Glu Val Val Ser Ala Gln Pro Ala Thr Phe Leu Ala Arg Ser Pro
            500                 505                 510 cac gtg ggc gtg aag gac gtg gag tgc ggc gag ggc cac ttc tgc cac    1584
His Val Gly Val Lys Asp Val Glu Cys Gly Glu Gly His Phe Cys His
        515                 520                 525 gac aac cag acc tgc tgc aga gac aac aga cag ggc tgg gcc tgc tgc    1632
Asp Asn Gln Thr Cys Cys Arg Asp Asn Arg Gln Gly Trp Ala Cys Cys
    530                 535                 540 ccc tac aga cag ggc gtg tgc tgc gcc gac aga aga cac tgc tgc ccc    1680
Pro Tyr Arg Gln Gly Val Cys Cys Ala Asp Arg Arg His Cys Cys Pro
545                 550                 555                 560 gcc gga ttt agg tgc gcc gcc aga ggc acc aag tgc ctg aga aga gag    1728
Ala Gly Phe Arg Cys Ala Ala Arg Gly Thr Lys Cys Leu Arg Arg Glu
                565                 570                 575 gcc ccc agg tgg gac gcc ccc ctg aga gac ccc gcc ctg aga cag ctg    1776
Ala Pro Arg Trp Asp Ala Pro Leu Arg Asp Pro Ala Leu Arg Gln Leu
            580                 585                 590 ctg                                                                  1779
Leu

<210> SEQ ID NO 5
<211> LENGTH: 593
<212> TYPE: PRT
<213> ORGANISM: Artificial sequence
<220> FEATURE:
<223> OTHER INFORMATION: Synthetic Construct

<400> SEQUENCE: 5

Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110
```

-continued

```
Phe Gln Arg Ser Gly Asn Asn Ser Val Gly Ala Ile Gln Cys Pro Asp
            115                 120                 125
Ser Gln Phe Glu Cys Pro Asp Phe Ser Thr Cys Cys Val Met Val Asp
        130                 135                 140
Gly Ser Trp Gly Cys Cys Pro Met Pro Gln Ala Ser Cys Cys Glu Asp
145                 150                 155                 160
Arg Val His Cys Cys Pro His Gly Ala Phe Cys Asp Leu Val His Thr
                165                 170                 175
Arg Cys Ile Thr Pro Thr Gly Thr His Pro Leu Ala Lys Lys Leu Pro
            180                 185                 190
Ala Gln Arg Thr Asn Arg Ala Val Ala Leu Ser Ser Val Met Cys
        195                 200                 205
Pro Asp Ala Arg Ser Arg Cys Pro Asp Gly Ser Thr Cys Cys Glu Leu
    210                 215                 220
Pro Ser Gly Lys Tyr Gly Cys Cys Pro Met Pro Asn Ala Thr Cys Cys
225                 230                 235                 240
Ser Asp His Leu His Cys Cys Pro Gln Asp Thr Val Cys Asp Leu Ile
                245                 250                 255
Gln Ser Lys Cys Leu Ser Lys Glu Asn Ala Thr Thr Asp Leu Leu Thr
            260                 265                 270
Lys Leu Pro Ala His Thr Val Gly Asp Val Lys Cys Asp Met Glu Val
        275                 280                 285
Ser Cys Pro Asp Gly Tyr Thr Cys Cys Arg Leu Gln Ser Gly Ala Trp
    290                 295                 300
Gly Cys Cys Pro Phe Thr Gln Ala Val Cys Cys Glu Asp His Ile His
305                 310                 315                 320
Cys Cys Pro Ala Gly Phe Thr Cys Asp Thr Gln Lys Gly Thr Cys Glu
                325                 330                 335
Gln Gly Pro His Gln Val Pro Trp Met Glu Lys Ala Pro Ala His Leu
            340                 345                 350
Ser Leu Pro Asp Pro Gln Ala Leu Lys Arg Asp Val Pro Cys Asp Asn
        355                 360                 365
Val Ser Ser Cys Pro Ser Ser Asp Thr Cys Cys Gln Leu Thr Ser Gly
    370                 375                 380
Glu Trp Gly Cys Cys Pro Ile Pro Glu Ala Val Cys Cys Ser Asp His
385                 390                 395                 400
Gln His Cys Cys Pro Gln Gly Tyr Thr Cys Val Ala Glu Gly Gln Cys
                405                 410                 415
Gln Arg Gly Ser Glu Ile Val Ala Gly Leu Glu Lys Met Pro Ala Arg
            420                 425                 430
Arg Ala Ser Leu Ser His Pro Arg Asp Ile Gly Cys Asp Gln His Thr
        435                 440                 445
Ser Cys Pro Val Gly Gln Thr Cys Cys Pro Ser Leu Gly Gly Ser Trp
    450                 455                 460
Ala Cys Cys Gln Leu Pro His Ala Val Cys Cys Glu Asp Arg Gln His
465                 470                 475                 480
Cys Cys Pro Ala Gly Tyr Thr Cys Asn Val Lys Ala Arg Ser Cys Glu
                485                 490                 495
Lys Glu Val Val Ser Ala Gln Pro Ala Thr Phe Leu Ala Arg Ser Pro
            500                 505                 510
His Val Gly Val Lys Asp Val Glu Cys Gly Glu Gly His Phe Cys His
        515                 520                 525
Asp Asn Gln Thr Cys Cys Arg Asp Asn Arg Gln Gly Trp Ala Cys Cys
```

```
                 530              535              540
Pro Tyr Arg Gln Gly Val Cys Cys Ala Asp Arg Arg His Cys Cys Pro
545              550              555              560

Ala Gly Phe Arg Cys Ala Ala Arg Gly Thr Lys Cys Leu Arg Arg Glu
            565              570              575

Ala Pro Arg Trp Asp Ala Pro Leu Arg Asp Pro Ala Leu Arg Gln Leu
            580              585              590

Leu

<210> SEQ ID NO 6
<211> LENGTH: 127
<212> TYPE: DNA
<213> ORGANISM: Artificial Sequence
<220> FEATURE:
<223> OTHER INFORMATION: rabbit globin polyA

<400> SEQUENCE: 6
gatctttttc cctctgccaa aaattatggg gacatcatga agccccttga gcatctgact    60
tctggctaat aaaggaaatt tattttcatt gcaatagtgt gttggaattt tttgtgtctc   120
tcactcg                                                             127

<210> SEQ ID NO 7
<211> LENGTH: 130
<212> TYPE: DNA
<213> ORGANISM: Artificial sequence
<220> FEATURE:
<223> OTHER INFORMATION: 3' AAV ITR

<400> SEQUENCE: 7
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcag                                                          130

<210> SEQ ID NO 8
<211> LENGTH: 130
<212> TYPE: DNA
<213> ORGANISM: Artificial sequence
<220> FEATURE:
<223> OTHER INFORMATION: 5' AAV ITR

<400> SEQUENCE: 8
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct                                                          130

<210> SEQ ID NO 9
<211> LENGTH: 382
<212> TYPE: DNA
<213> ORGANISM: Artificial sequence
<220> FEATURE:
<223> OTHER INFORMATION: human CMV IE promoter

<400> SEQUENCE: 9
ctagtcgaca ttgattattg actagttatt aatagtaatc aattacgggg tcattagttc    60
atagcccata tatggagttc cgcgttacat aacttacggt aaatggcccg cctggctgac   120
cgcccaacga cccccgccca ttgacgtcaa taatgacgta tgttcccata gtaacgccaa   180
tagggacttt ccattgacgt caatgggtgg actatttacg gtaaactgcc cacttggcag   240
```

| | |
|---|---|
| tacatcaagt gtatcatatg ccaagtacgc cccctattga cgtcaatgac ggtaaatggc | 300 |
| ccgcctggca ttatgcccag tacatgacct tatgggactt tcctacttgg cagtacatct | 360 |
| acgtattagt catcgctatt ac | 382 |

<210> SEQ ID NO 10
<211> LENGTH: 282
<212> TYPE: DNA
<213> ORGANISM: Artificial sequence
<220> FEATURE:
<223> OTHER INFORMATION: CB promoter

<400> SEQUENCE: 10

| | |
|---|---|
| tggtcgaggt gagccccacg ttctgcttca ctctccccat ctcccccccc tccccacccc | 60 |
| caatttgta tttatttatt ttttaattat tttgtgcagc gatggggggcg ggggggggg | 120 |
| ggggcgcgc gccaggcggg gcgggcggg gcgaggggcg gggcggggcg aggcggagag | 180 |
| gtgcggcggc agccaatcag agcggcgcgc tccgaaagtt ccttttatg gcgaggcggc | 240 |
| ggcggcggcg gccctataaa aagcgaagcg cgcggcgggc gg | 282 |

<210> SEQ ID NO 11
<211> LENGTH: 973
<212> TYPE: DNA
<213> ORGANISM: Artificial sequence
<220> FEATURE:
<223> OTHER INFORMATION: chimeric intron

<400> SEQUENCE: 11

| | |
|---|---|
| gtgagcgggc gggacggccc ttctcctccg ggctgtaatt agcgcttggt ttaatgacgg | 60 |
| cttgtttctt ttctgtggct gcgtgaaagc cttgaggggc tccgggaggg ccctttgtgc | 120 |
| gggggggagcg gctcgggggg tgcgtgcgtg tgtgtgtgcg tggggagcgc cgcgtgcggc | 180 |
| tccgcgctgc ccggcggctg tgagcgctgc gggcgcggcg cggggctttg tgcgctccgc | 240 |
| agtgtgcgcg aggggagcgc ggccggggc ggtgccccgc ggtgcggggg gggctgcgag | 300 |
| gggaacaaag gctgcgtgcg gggtgtgtgc gtggggggt gagcaggggg tgtgggcgcg | 360 |
| tcggtcgggc tgcaaccccc cctgcacccc cctccccgag ttgctgagca cggcccggct | 420 |
| tcgggtgcgg ggctccgtac ggggcgtggc gcggggctcg ccgtgccggg cgggggtgg | 480 |
| cggcaggtgg gggtgccggg cggggcgggg ccgcctcggg ccggggaggg ctcggggag | 540 |
| gggcgcggcg gcccccggag cgccggcggc tgtcgaggcg cggcgagccg cagccattgc | 600 |
| cttttatggt aatcgtgcga gagggcgcag ggacttcctt tgtcccaaat ctgtgcggag | 660 |
| ccgaaatctg ggaggcgccg ccgcaccccc tctagcgggc gcggggcgaa gcggtgcggc | 720 |
| gccggcagga aggaaatggg cggggagggc cttcgtgcgt cgccgcgccg ccgtcccctt | 780 |
| ctccctctcc agcctcgggg ctgtccgcgg gggacggct gccttcgggg gggacggggc | 840 |
| agggcggggt tcggcttctg gcgtgtgacc ggcggctcta gagcctctgc taaccatgtt | 900 |
| catgccttct tctttttcct acagctcctg ggcaacgtgc tggttattgt gctgtctcat | 960 |
| cattttggca aag | 973 |

<210> SEQ ID NO 12
<211> LENGTH: 1227
<212> TYPE: DNA
<213> ORGANISM: Artificial sequence
<220> FEATURE:
<223> OTHER INFORMATION: UbC promoter

<400> SEQUENCE: 12

```
ggcctccgcg ccgggttttg gcgcctcccg cgggcgcccc cctcctcacg gcgagcgctg    60
ccacgtcaga cgaagggcgc aggagcgtcc tgatccttcc gcccggacgc tcaggacagc   120
ggcccgctgc tcataagact cggccttaga accccagtat cagcagaagg acattttagg   180
acgggacttg ggtgactcta gggcactggt tttctttcca gagagcggaa caggcgagga   240
aaagtagtcc cttctcggcg attctgcgga gggatctccg tggggcggtg aacgccgatg   300
attatataag gacgcgccgg gtgtggcaca gctagttccg tcgcagccgg gatttgggtc   360
gcggttcttg tttgtggatc gctgtgatcg tcacttggtg agtagcgggc tgctgggctg   420
gccggggctt tcgtggccgc cgggccgctc ggtgggacgg aagcgtgtgg agagaccgcc   480
aagggctgta gtctgggtcc gcgagcaagg ttgccctgaa ctgggggttg ggggagcgc    540 agcaaaatgg cggctgttcc cgagtcttga atggaagacg cttgtgaggc gggctgtgag   600
gtcgttgaaa caaggtgggg ggcatggtgg gcggcaagaa cccaaggtct tgaggccttc   660
gctaatgcgg gaaagctctt attcgggtga gatgggctgg ggcaccatct ggggaccctg   720
acgtgaagtt tgtcactgac tggagaactc ggtttgtcgt ctgttgcggg ggcggcagtt   780
atgcggtgcc gttgggcagt gcacccgtac ctttgggagc gcgcgccctc gtcgtgtcgt   840
gacgtcaccc gttctgttgg cttataatgc agggtggggc cacctgccgg taggtgtgcg   900
gtaggctttt ctccgtcgca ggacgcaggg ttcgggccta gggtaggctc tcctgaatcg   960
acaggcgccg gacctctggt gaggggaggg ataagtgagg cgtcagtttc tttggtcggt  1020
tttatgtacc tatcttctta agtagctgaa gctccggttt tgaactatgc gctcggggtt  1080
ggcgagtgtg ttttgtgaag tttttaggc acctttgaa atgtaatcat ttgggtcaat  1140
atgtaatttt cagtgttaga ctagtaaatt gtccgctaaa ttctggccgt ttttggcttt  1200
tttgttagac gaagctttat tgcggta                                     1227

<210> SEQ ID NO 13
<211> LENGTH: 133
<212> TYPE: DNA
<213> ORGANISM: Artificial sequence
<220> FEATURE:
<223> OTHER INFORMATION: intron

<400> SEQUENCE: 13
gtaagtatca aggttacaag acaggtttaa ggagaccaat agaaactggg cttgtcgaga    60
cagagaagac tcttgcgttt ctgataggca cctattggtc ttactgacat ccactttgcc   120
tttctctcca cag                                                     133

<210> SEQ ID NO 14
<211> LENGTH: 232
<212> TYPE: DNA
<213> ORGANISM: Artificial sequence
<220> FEATURE:
<223> OTHER INFORMATION: SV40 late polyA

<400> SEQUENCE: 14
cgagcagaca tgataagata cattgatgag tttggacaaa ccacaactag aatgcagtga    60
aaaaaatgct ttatttgtga aatttgtgat gctattgctt tatttgtaac cattataagc   120
tgcaataaac aagttaacaa caacaattgc attcatttta tgtttcaggt tcaggggag   180 atgtgggagg ttttttaaag caagtaaaac ctctacaaat gtggtaaaat cg           232

<210> SEQ ID NO 15
```

<211> LENGTH: 858
<212> TYPE: DNA
<213> ORGANISM: Artificial sequence
<220> FEATURE:
<223> OTHER INFORMATION: Ampicillin resistance gene

<400> SEQUENCE: 15

```
atgagtattc aacatttccg tgtcgccctt attccctttt ttgcggcatt ttgccttcct      60
gttttttgctc acccagaaac gctggtgaaa gtaaaagatg ctgaagatca gttgggtgca    120
cgagtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga caccacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatggatgaa cgaaatagac agatcgctga taggtgcc      840
tcactgatta agcattgg                                                   858
```

<210> SEQ ID NO 16
<211> LENGTH: 589
<212> TYPE: DNA
<213> ORGANISM: Artificial sequence
<220> FEATURE:
<223> OTHER INFORMATION: COL E1 origin

<400> SEQUENCE: 16

```
ttgagatcct ttttttctgc gcgtaatctg ctgcttgcaa acaaaaaaac caccgctacc     60
agcggtggtt tgtttgccgg atcaagagct accaactctt tttccgaagg taactggctt   120
cagcagagcg cagataccaa atactgttct tctagtgtag ccgtagttag gccaccactt   180
caagaactct gtagcaccgc ctacatacct cgctctgcta atcctgttac cagtggctgc   240
tgccagtggc gataagtcgt gtcttaccgg gttggactca agacgatagt taccggataa   300
ggcgcagcgg tcgggctgaa cggggggttc gtgcacacag cccagcttgg agcgaacgac   360
ctacaccgaa ctgagatacc tacagcgtga gctatgagaa agcgccacgc ttcccgaagg   420
gagaaaggcg gacaggtatc cggtaagcgg cagggtcgga acaggagagc gcacgaggga   480
gcttccaggg ggaaacgcct ggtatcttta tagtcctgtc gggtttcgcc acctctgact   540
tgagcgtcga tttttgtgat gctcgtcagg ggggcggagc ctatggaaa             589
```

<210> SEQ ID NO 17
<211> LENGTH: 1184
<212> TYPE: DNA
<213> ORGANISM: Artificial sequence
<220> FEATURE:
<223> OTHER INFORMATION: EF-1a promoter

<400> SEQUENCE: 17

```
cgtgaggctc cggtgcccgt cagtgggcag agcgcacatc gcccacagtc cccgagaagt     60
```

```
tgggggggagg ggtcggcaat tgaaccggtg cctagagaag gtggcgcggg gtaaactggg      120
aaagtgatgt cgtgtactgg ctccgccttt ttcccgaggg tggggagaa ccgtatataa       180 gtgcagtagt cgccgtgaac gttcttttc gcaacgggtt tgccgccaga acacaggtaa       240
gtgccgtgtg tggttcccgc gggcctggcc tctttacggg ttatggccct tgcgtgcctt     300
gaattacttc cacctggctg cagtacgtga ttcttgatcc cgagcttcgg gttggaagtg     360
ggtgggagag ttcgaggcct tgcgcttaag gagccccttc gcctcgtgct tgagtttgagg   420 cctggcctgg gcgctggggc cgccgcgtgc gaatctggtg gcaccttcgc gcctgtctcg   480
ctgctttcga taagtctcta gccatttaaa attttttgatg acctgctgcg acgctttttt    540
tctggcaaga tagtcttgta aatgcgggcc aagatctgca cactggtatt tcggttttgg    600
gggccgcggg cggcgacggg gcccgtgcgt cccagcgcac atgttcggcg aggcggggcc  660
tgcgagcgcg gccaccgaga atcggacggg ggtagtctca agctggccgg cctgctctgg  720
tgcctggcct cgcgccgccg tgtatcgccc cgccctgggc ggcaaggctg gcccggtcgg   780
caccagttgc gtgagcggaa agatggccgc ttccggcc tgctgcaggg agctcaaaat       840
ggaggacgcg gcgctcggga gagcgggcgg gtgagtcacc cacacaaagg aaaagggcct    900
ttccgtcctc agccgtcgct tcatgtgact ccacggagta ccgggcgccg tccaggcacc   960
tcgattagtt ctcgagcttt tggagtacgt cgtctttagg ttgggggag gggttttatg      1020 cgatggagtt tccccacact gagtgggtgg agactgaagt taggccagct tggcacttga   1080
tgtaattctc cttggaattt gccctttttg agtttggatc ttggttcatt ctcaagcctc        1140
agacagtggt tcaaagtttt tttcttccat ttcaggtgtc gtga                          1184

<210> SEQ ID NO 18
<211> LENGTH: 456
<212> TYPE: DNA
<213> ORGANISM: Artificial sequence
<220> FEATURE:
<223> OTHER INFORMATION: F1 ori

<400> SEQUENCE: 18
acgcgccctg tagcggcgca ttaagcgcgg cgggtgtggt ggttacgcgc agcgtgaccg      60
ctacacttgc cagcgcccta gcgcccgctc ctttcgcttt cttcccttcc tttctcgcca      120
cgttcgccgg ctttccccgt caagctctaa atcgggggct ccctttaggg ttccgattta     180
gtgctttacg gcacctcgac cccaaaaaac ttgattaggg tgatggttca cgtagtgggc    240
catcgcccta tagacggtt tttcgccctt tgacgttgga gtccacgttc tttaatagtg       300
gactcttgtt ccaaactgga acaacactca accctatctc ggtctattct tttgatttat       360
aagggatttt gccgatttcg gcctattggt taaaaaatga gctgatttaa caaaaattta     420
acgcgaattt taacaaaata ttaacgctta caattt                                   456

<210> SEQ ID NO 19
<211> LENGTH: 816
<212> TYPE: DNA
<213> ORGANISM: Artificial sequence
<220> FEATURE:
<223> OTHER INFORMATION: Kanamycin resistance gene

<400> SEQUENCE: 19
ttagaaaaac tcatcgagca tcaaatgaaa ctgcaattta ttcatatcag gattatcaat     60
accatatttt tgaaaaagcc gtttctgtaa tgaaggagaa aactcaccga ggcagttcca    120
```

| | |
|---|---|
| taggatggca agatcctggt atcggtctgc gattccgact cgtccaacat caatacaacc | 180 |
| tattaatttc ccctcgtcaa aaataaggtt atcaagtgag aaatcaccat gagtgacgac | 240 |
| tgaatccggt gagaatggca aaagcttatg catttctttc cagacttgtt caacaggcca | 300 |
| gccattacgc tcgtcatcaa aatcactcgc atcaaccaaa ccgttattca ttcgtgattg | 360 |
| cgcctgagcg agacgaaata cgcgatcgct gttaaaagga caattacaaa caggaatcga | 420 |
| atgcaaccgg cgcaggaaca ctgccagcgc atcaacaata ttttcacctg aatcaggata | 480 |
| ttcttctaat acctggaatg ctgttttccc ggggatcgca gtggtgagta accatgcatc | 540 |
| atcaggagta cggataaaat gcttgatggt cggaagaggc ataaattccg tcagccagtt | 600 |
| tagtctgacc atctcatctg taacatcatt ggcaacgcta cctttgccat gtttcagaaa | 660 |
| caactctggc gcatcgggct tcccatacaa tcgatagatt gtcgcacctg attgcccgac | 720 |
| attatcgcga gcccatttat acccatataa atcagcatcc atgttggaat ttaatcgcgg | 780 |
| cctcgagcaa gacgtttccc gttgaatatg gctcat | 816 |

```
<210> SEQ ID NO 20
<211> LENGTH: 131
<212> TYPE: DNA
<213> ORGANISM: Artificial sequence
<220> FEATURE:
<223> OTHER INFORMATION: P5 promoter

<400> SEQUENCE: 20
```

| | |
|---|---|
| gtcctgtatt agaggtcacg tgagtgtttt gcgacatttt gcgacaccat gtggtcacgc | 60 |
| tgggtattta agcccgagtg agcacgcagg gtctccattt gaagcgggga ggtttgaacg | 120 |
| cgcagccgcc a | 131 |

```
<210> SEQ ID NO 21
<211> LENGTH: 295
<212> TYPE: DNA
<213> ORGANISM: Artificial seqeuence
<220> FEATURE:
<223> OTHER INFORMATION: LacZ promoter

<400> SEQUENCE: 21
```

| | |
|---|---|
| gcggccgcca ccgcggtgga gctccagctt ttgttccctt tagtgagggt taattgcgcg | 60 |
| cttggcgtaa tcatggtcat agctgtttcc tgtgtgaaat tgttatccgc tcacaattcc | 120 |
| acacaacata cgagccggaa gcataaagtg taaagcctgg ggtgcctaat gagtgagcta | 180 |
| actcacatta attgcgttgc gctcactgcc cgctttccag tcgggaaacc tgtcgtgcca | 240 |
| gctgcattaa tgaatcggcc aacgcgcggg gagaggcggt ttgcgtattg ggcgc | 295 |

```
<210> SEQ ID NO 22
<211> LENGTH: 3852
<212> TYPE: DNA
<213> ORGANISM: Artificial sequence
<220> FEATURE:
<223> OTHER INFORMATION: EF1a.huPGRN.SV40
<220> FEATURE:
<221> NAME/KEY: repeat_region
<222> LOCATION: (1)..(130)

<400> SEQUENCE: 22
```

| | |
|---|---|
| ctgcgcgctc gctcgctcac tgaggccgcc cgggcaaagc ccgggcgtcg gcgacctttt | 60 |
| ggtcgcccgg cctcagtgag cgagcagcg cgcagagagg gagtggccaa ctccatcact | 120 |
| aggggttcct tgtagttaat gattaacccg ccatgctact tatctacgta gccatgctct | 180 |

| | |
|---|---|
| aggaagatcc gatgtacggg ccagatatac gcgttgacat tgattattga ctaggctttt | 240 |
| gcaaaaagct ttgcaaagat ggataaagtt ttaaacagag aggaatcttt gcagctaatg | 300 |
| gaccttctag gtcttgaaag gagtgcctcg tgaggctccg gtgcccgtca gtgggcagag | 360 |
| cgcacatcgc ccacagtccc cgagaagttg ggggagggg tcggcaattg aaccggtgcc | 420 |
| tagagaaggt ggcgcggggt aaactgggaa agtgatgtcg tgtactggct ccgcctttt | 480 |
| cccgagggtg ggggagaacc gtatataagt gcagtagtcg ccgtgaacgt tcttttcgc | 540 |
| aacgggtttg ccgccagaac acaggtaagt gccgtgtgtg gttcccgcgg gcctggcctc | 600 |
| tttacgggtt atggcccttg cgtgccttga attacttcca cctggctgca gtacgtgatt | 660 |
| cttgatcccg agcttcgggt tggaagtggg tgggagagtt cgaggccttg cgcttaagga | 720 |
| gccccttcgc ctcgtgcttg agttgaggcc tggcctgggc gctggggccg ccgcgtgcga | 780 |
| atctggtggc accttcgcgc ctgtctcgct gctttcgata agtctctagc catttaaaat | 840 |
| ttttgatgac ctgctgcgac gcttttttc tggcaagata gtcttgtaaa tgcgggccaa | 900 |
| gatctgcaca ctggtatttc ggttttggg gccgcgggcg gcgacgggc ccgtgcgtcc | 960 |
| cagcgcacat gttcggcgag gcggggcctg cgagcgcggc caccgagaat cggacggggg | 1020 |
| tagtctcaag ctggccggcc tgctctggtg cctggcctcg cgccgccgtg tatcgccccg | 1080 |
| ccctgggcgg caaggctggc ccggtcggca ccagttgcgt gagcggaaag atggccgctt | 1140 |
| cccggccctg ctgcagggag ctcaaaatgg aggacgcggc gctcgggaga gcgggcgggt | 1200 |
| gagtcaccca cacaaaggaa aagggccttt ccgtcctcag ccgtcgcttc atgtgactcc | 1260 |
| acggagtacc gggcgccgtc caggcacctc gattagttct cgagcttttg gagtacgtcg | 1320 |
| tcttttaggtt ggggggaggg gttttatgcg atggagtttc cccacactga gtgggtggag | 1380 |
| actgaagtta ggccagcttg gcacttgatg taattctcct tggaatttgc ccttttgag | 1440 |
| tttggatctt ggttcattct caagcctcag acagtggttc aaagttttt tcttccattt | 1500 |
| caggtgtcgt gaggaattag cttggtacta atacgactca ctatagggag acccaagctg | 1560 |
| gctaggtaag cttggtaccg agctcggatc aattcgccac catgtggacc ctggtgtctt | 1620 |
| gggttgcact gacagctgga ctggtggccg gcacaagatg tcctgacggc cagttttgcc | 1680 |
| ccgtggcctg ctgtcttgat cctggcggag ccagctacag ctgctgcaga cctctgctgg | 1740 |
| ataagtggcc caccacactg agcagacacc tcggaggacc ttgtcaggtg gacgcccact | 1800 |
| gttctgccgg acacagctgc atctttaccg tgtctggcac ctccagctgc tgtccatttc | 1860 |
| ctgaggctgt ggcctgcgga gacgccacc actgttgtcc tagaggcttc cactgtagcg | 1920 |
| ccgacggcag aagctgcttt cagagaagcg gcaacaatag cgtgggcgcc atccagtgtc | 1980 |
| ctgacagcca gttcgagtgc cccgacttca gcacctgttg cgtgatggtg gacggcagct | 2040 |
| ggggctgttg tccaatgcct caggctagct gctgcgagga cagagtgcac tgttgccctc | 2100 |
| acggcgcctt ttgcgatctg gtgcacaccc ggtgcatcac cccaacaggc acacatcctc | 2160 |
| tggccaagaa gctgcctgct cagcggacca atagagccgt ggctctgagc agcagcgtga | 2220 |
| tgtgccctga cgccagatcc aggtgtccag acggctccac atgttgcgaa ctgcccagcg | 2280 |
| gcaaatacgg ctgctgcccc atgcctaacg ccacatgctg tagcgaccat cttcactgct | 2340 |
| gcccacaaga caccgtgtgc gacctgatcc agagcaagtg cctgagcaaa gagaacgcca | 2400 |
| ccaccgacct gctgaccaaa ctgccagctc acaccgtggg agatgtgaag tgcgacatgg | 2460 |
| aagtgtcttg ccccgacggc tatacctgct gtagactgca atctggcgcc tggggctgct | 2520 |
| gcccttttac acaagctgtg tgttgcgagg accacatcca ttgctgccct gccggcttca | 2580 |

-continued

| | |
|---|---|
| cctgtgacac acagaaaggc acctgcgagc agggccctca tcaggtgcca tggatggaaa | 2640 |
| aagcccctgc tcacctgagc ctgcctgatc ctcaagctct gaagagggac gtgccctgcg | 2700 |
| acaatgtgtc tagctgccct agcagcgaca cctgctgcca gctgacatct ggcgagtggg | 2760 |
| gctgctgtcc tataccagag gccgtgtgtt gttccgacca ccagcattgc tgtccccaag | 2820 |
| gctacacctg tgtggccgaa ggccaatgtc aacgggctc tgaaattgtg gccggcctgg | 2880 |
| aaaagatgcc cgccagaagg gcttctctgt ctcaccccg ggacatcggc tgcgaccagc | 2940 |
| acacatcttg tcctgtgggc cagacctgtt gtccctctct tggtggatcc tgggcttgct | 3000 |
| gtcagctgcc tcacgccgtg tgctgcgaag atagacaaca ctgctgtccc gccggataca | 3060 |
| cctgtaacgt gaaggccaga tcctgcgaga agaagtggt gtctgcccag cctgccacct | 3120 |
| tcctggctag aagtcctcac gtgggcgtga aggacgtgga gtgtggcgag gccacttct | 3180 |
| gccacgacaa tcagacatgc tgcagagaca accggcaagg ctgggcttgt tgcccatata | 3240 |
| gacagggcgt gtgctgtgcc gacagaaggc actgttgtcc agccggcttt agatgtgccg | 3300 |
| ccagggcac aaagtgtctg agaagggaag cccctaggtg ggacgcccct ctgagagatc | 3360 |
| ctgctctgag acagctgctc tgatgaggta cctctagagt cgacccgggc ggcctcgagg | 3420 |
| ccgcttcgag cagacatgat aagatacatt gatgagtttg gacaaaccac aactagaatg | 3480 |
| cagtgaaaaa aatgctttat ttgtgaaatt tgtgatgcta ttgctttatt tgtaaccatt | 3540 |
| ataagctgca ataaacaagt taacaacaac aattgcattc attttatgtt tcaggttcag | 3600 |
| ggggagatgt gggaggtttt ttaaagcaag taaaacctct acaaatgtgg taaaatcgat | 3660 |
| aaggatcttc ctagagcatg gctacgtaga taagtagcat ggcgggttaa tcattaacta | 3720 |
| caaggaaccc ctagtgatgg agttggccac tccctctctg cgcgctcgct cgctcactga | 3780 |
| ggccgggcga ccaaaggtcg cccgacgccc gggctttgcc cgggcggcct cagtgagcga | 3840 |
| gcgagcgcgc ag | 3852 |

<210> SEQ ID NO 23
<211> LENGTH: 3972
<212> TYPE: DNA
<213> ORGANISM: Artificial sequence
<220> FEATURE:
<223> OTHER INFORMATION: Ubc.PI.huPGRN.SV40

<400> SEQUENCE: 23

| | |
|---|---|
| ctgcgcgctc gctcgctcac tgaggccgcc cgggcaaagc ccgggcgtcg ggcgacctttt | 60 |
| ggtcgcccgg cctcagtgag cgagcgagcg cgcagagagg gagtggccaa ctccatcact | 120 |
| aggggttcct tgtagttaat gattaacccg ccatgctact tatctacgta gccatgctct | 180 |
| aggaagatct ggcctccgcg ccgggttttg gcgcctcccg cgggcgcccc cctcctcacg | 240 |
| gcgagcgctg ccacgtcaga cgaagggcgc aggagcgtcc tgatccttcc gcccggacgc | 300 |
| tcaggacagc ggcccgctgc tcataagact cggccttaga accccagtat cagcagaagg | 360 |
| acatttagg acgggacttg ggtgactcta gggcactggt tttctttcca gagagcggaa | 420 |
| caggcgagga aaagtagtcc cttctcggcg attctgcgga gggatctccg tggggcggtg | 480 |
| aacgccgatg attatataag gacgcgccgg gtgtggcaca gctagttccg tcgcagccgg | 540 |
| gatttgggtc gcggttcttg tttgtggatc gctgtgatcg tcacttggtg agtagcgggc | 600 |
| tgctgggctg gccggggctt tcgtggccgc cgggccgctc ggtgggacgg aagcgtgtgg | 660 |
| agagaccgcc aagggctgta gtctgggtcc gcgagcaagg ttgccctgaa ctgggggttg | 720 |

```
gggggagcgc agcaaaatgg cggctgttcc cgagtcttga atggaagacg cttgtgaggc    780
gggctgtgag gtcgttgaaa caaggtgggg ggcatggtgg gcggcaagaa cccaaggtct    840
tgaggccttc gctaatgcgg gaaagctctt attcgggtga gatgggctgg ggcaccatct    900
ggggaccctg acgtgaagtt tgtcactgac tggagaactc ggtttgtcgt ctgttgcggg    960
ggcggcagtt atgcggtgcc gttgggcagt gcacccgtac ctttgggagc gcgcgccctc   1020
gtcgtgtcgt gacgtcaccc gttctgttgg cttataatgc agggtggggc cacctgccgg   1080
taggtgtgcg gtaggctttt ctccgtcgca ggacgcaggg ttcgggccta gggtaggctc   1140
tcctgaatcg acaggcgccg gacctctggt gaggggaggg ataagtgagg cgtcagtttc   1200
tttggtcggt tttatgtacc tatcttctta agtagctgaa gctccggttt tgaactatgc   1260
gctcggggtt ggcgagtgtg ttttgtgaag ttttttaggc accttttgaa atgtaatcat   1320
ttgggtcaat atgtaatttt cagtgttaga ctagtaaatt gtccgctaaa ttctggccgt   1380
ttttggcttt tttgttagac gaagctttat tgcggtagtt tatcacagtt aaattgctaa   1440
cgcagtcagt gcttctgaca caacagtctc gaacttaagc tgcagaagtt ggtcgtgagg   1500
cactgggcag gtaagtatca aggttacaag acaggtttaa ggagaccaat agaaactggg   1560
cttgtcgaga cagagaagac tcttgcgttt ctgataggca cctattggtc ttactgacat   1620
ccactttgcc tttctctcca caggtgtcca ctcccagttc aattacagct cttaaggcta   1680
gagtacttaa tacgactcac tataggctag aattcgccac catgtggacc ctggtgtctt   1740
gggttgcact gacagctgga ctggtggccg gcacaagatg tcctgacggc cagttttgcc   1800
ccgtggcctg ctgtcttgat cctggcgag ccagctacag ctgctgcaga cctctgctgg   1860
ataagtggcc caccacactg agcagacacc tcggaggacc ttgtcaggtg gacgcccact   1920
gttctgccgg acacagctgc atctttaccg tgtctggcac ctccagctgc tgtccatttc   1980
ctgaggctgt ggcctgcgga gacggccacc actgttgtcc tagaggcttc cactgtagcg   2040
ccgacggcag aagctgcttt cagagaagcg gcaacaatag cgtgggcgcc atccagtgtc   2100
ctgacagcca gttcgagtgc cccgacttca gcacctgttg cgtgatggtg gacggcagct   2160
ggggctgttg tccaatgcct caggctagct gctgcgagga cagagtgcac tgttgccctc   2220
acggcgcctt ttgcgatctg gtgcacaccc ggtgcatcac cccaacaggc acacatcctc   2280
tggccaagaa gctgcctgct cagcggacca atagagccgt ggctctgagc agcagcgtga   2340
tgtgccctga cgccagatcc aggtgtccag acggctccac atgttgcgaa ctgcccagcg   2400
gcaaatacgg ctgctgcccc atgcctaacg ccacatgctg tagcgaccat cttcactgct   2460
gcccacaaga caccgtgtgc gacctgatcc agagcaagtg cctgagcaaa gagaacgcca   2520
ccaccgacct gctgaccaaa ctgccagctc acaccgtggg agatgtgaag tgcgacatgg   2580
aagtgtcttg ccccgacggc tatacctgct gtagactgca atctggcgcc tggggctgct   2640
gccccttttac acaagctgtg tgttgcgagg accacatcca ttgctgccct gccgcttca   2700
cctgtgacac acagaaaggc acctgcgagc agggccctca tcaggtgcca tggatggaaa   2760
aagcccctgc tcacctgagc ctgcctgatc ctcaagctct gaagagggac gtgccctgcg   2820
acaatgtgtc tagctgccct agcagcgaca cctgctgcca gctgacatct ggcgagtggg   2880
gctgctgtcc tataccagag gccgtgtgtt gttccgacca ccagcattgc tgtccccaag   2940
gctacacctg tgtggccgaa ggccaatgtc aacgggctc tgaaattgtg gccggctgg   3000
aaaagatgcc cgccagaagg gcttctctgt ctcaccccg ggacatcggc tgcgaccagc   3060
acacatcttg tcctgtgggc cagacctgtt gtccctctct tggtggatcc tgggcttgct   3120
```

```
gtcagctgcc tcacgccgtg tgctgcgaag atagacaaca ctgctgtccc gccggataca    3180
cctgtaacgt gaaggccaga tcctgcgaga aagaagtggt gtctgcccag cctgccacct    3240
tcctggctag aagtcctcac gtgggcgtga aggacgtgga gtgtggcgag ggccacttct    3300
gccacgacaa tcagacatgc tgcagagaca accggcaagg ctgggcttgt tgcccatata    3360
gacagggcgt gtgctgtgcc gacagaaggc actgttgtcc agccggcttt agatgtgccg    3420
ccaggggcac aaagtgtctg agaagggaag cccctaggtg ggacgcccct ctgagagatc    3480
ctgctctgag acagctgctc tgatgaggta cctctagagt cgacccgggc ggcctcgagg    3540
ccgcttcgag cagacatgat aagatacatt gatgagtttg gacaaaccac aactagaatg    3600
cagtgaaaaa aatgctttat ttgtgaaatt tgtgatgcta ttgctttatt tgtaaccatt    3660
ataagctgca ataaacaagt taacaacaac aattgcattc attttatgtt tcaggttcag    3720
ggggagatgt gggaggtttt ttaaagcaag taaaacctct acaaatgtgg taaaatcgat    3780
aaggatcttc ctagagcatg gctacgtaga taagtagcat ggcgggttaa tcattaacta    3840
caaggaaccc ctagtgatgg agttggccac tccctctctg cgcgctcgct cgctcactga    3900
ggccgggcga ccaaaggtcg cccgacgccc gggctttgcc cgggcggcct cagtgagcga    3960
gcgagcgcgc ag                                                        3972

<210> SEQ ID NO 24
<211> LENGTH: 4131
<212> TYPE: DNA
<213> ORGANISM: Artificial sequence
<220> FEATURE:
<223> OTHER INFORMATION: CB7.CI.hPGRN1.rBG
<220> FEATURE:
<221> NAME/KEY: misc_feature
<222> LOCATION: (1)..(130)
<223> OTHER INFORMATION: 5' ITR
<220> FEATURE:
<221> NAME/KEY: misc_feature
<222> LOCATION: (198)..(579)
<223> OTHER INFORMATION: CMV IE enhancer
<220> FEATURE:
<221> NAME/KEY: misc_feature
<222> LOCATION: (582)..(863)
<223> OTHER INFORMATION: chicken beta-actin promoter
<220> FEATURE:
<221> NAME/KEY: misc_feature
<222> LOCATION: (958)..(1930)
<223> OTHER INFORMATION: chimeric intron
<220> FEATURE:
<221> NAME/KEY: misc_feature
<222> LOCATION: (1942)..(3726)
<223> OTHER INFORMATION: hPGRN
<220> FEATURE:
<221> NAME/KEY: misc_feature
<222> LOCATION: (3787)..(3913)
<223> OTHER INFORMATION: rabbit beta globin poly A
<220> FEATURE:
<221> NAME/KEY: misc_feature
<222> LOCATION: (4002)..(4131)
<223> OTHER INFORMATION: 3' ITR

<400> SEQUENCE: 24
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctaccag ggtaatgggg     180
atcctctaga actatagcta gtcgacattg attattgact agttattaat agtaatcaat     240
tacggggtca ttagttcata gcccatatat ggagttccgc gttacataac ttacggtaaa     300
```

```
tggcccgcct ggctgaccgc ccaacgaccc ccgcccattg acgtcaataa tgacgtatgt    360
tcccatagta acgccaatag ggactttcca ttgacgtcaa tgggtggact atttacggta    420
aactgcccac ttggcagtac atcaagtgta tcatatgcca agtacgcccc ctattgacgt    480
caatgacggt aaatggcccg cctggcatta tgcccagtac atgaccttat gggactttcc    540
tacttggcag tacatctacg tattagtcat cgctattacc atggtcgagg tgagccccac    600
gttctgcttc actctcccca tctcccccc ctccccaccc caattttgt atttatttat    660 tttttaatta ttttgtgcag cgatgggggc ggggggggg ggggggcgcg cgccaggcgg    720
ggcggggcgg ggcgagggc ggggcgggc gaggcggaga ggtgcggcgg cagccaatca    780
gagcggcgcg ctccgaaagt ttccttttat ggcgaggcgg cggcggcggc ggccctataa    840
aaagcgaagc gcgcggcggg cggggagtcg ctgcgacgct gccttcgccc cgtgccccgc    900
tccgccgccg cctcgcgccg cccgcccgg ctctgactga ccgcgttact cccacaggtg    960
agcgggcggg acggcccttc tcctccgggc tgtaattagc gcttggttta atgacggctt   1020
gtttcttttc tgtggctgcg tgaaagcctt gaggggctcc ggggagggccc tttgtgcggg   1080 gggagcggct cggggggtgc gtgcgtgtgt gtgtgcgtgg ggagcgccgc gtgcggctcc   1140
gcgctgcccg gcggctgtga gcgctgcggg gcgggcgcgg ggctttgtgc gctccgcagt   1200
gtgcgcgagg ggagcgcggc cgggggcggt gccccgcggt gcgggggggg ctgcgagggg   1260
aacaaaggct gcgtgcgggg tgtgtgcgtg ggggggtgag caggggggtgt gggcgcgtcg   1320 gtcgggctgc aacccccct gcaccccct ccccgagttg ctgagcacgg cccggcttcg   1380
ggtgcggggc tccgtacggg gcgtggcgcg ggctcgccg tgccgggcgg ggggtggcgg   1440
caggtggggg tgccgggcgg ggcggggccg cctcgggccg gggagggctc gggggagggg   1500
cgcggcggcc cccggagcgc cggcggctgt cgaggcgcgg cgagccgcag ccattgcctt   1560
ttatggtaat cgtgcgagag ggcgcaggga cttcctttgt cccaaatctg tgcggagccg   1620
aaatctggga ggcgccgccg caccccctct agcgggcgcg gggcgaagcg gtgcggcgcc   1680
ggcaggaagg aaatgggcgg ggagggcctt cgtgcgtcgc cgcgccgccg tccccttctc   1740
cctctccagc ctcggggctg tccgcggggg gacggctgcc ttcgggggg acggggcagg   1800 gcggggttcg gcttctggcg tgtgaccggc ggctctagag cctctgctaa ccatgttcat   1860
gccttcttct ttttcctaca gctcctgggc aacgtgctgg ttattgtgct gtctcatcat   1920
tttggcaaag aattcgccac catgtggacc ctggtgtctt gggttgcact gacagctgga   1980
ctggtggccg gcacaagatg tcctgacggc cagttttgcc ccgtggcctg ctgtcttgat   2040
cctggcggag ccagctacag ctgctgcaga cctctgctgg ataagtggcc caccacactg   2100
agcagacacc tcgaggacc ttgtcaggtg acgcccact gttctgccgg acacagctgc   2160
atctttaccg tgtctggcac ctccagctgc tgtccatttc ctgaggctgt ggcctgcgga   2220 gacgccacc actgttgtcc tagaggcttc cactgtagcg ccgacggcag aagctgcttt   2280
cagagaagcg gcaacaatag cgtgggcgcc atccagtgtc ctgacagcca gttcgagtgc   2340
cccgacttca gcacctgttg cgtgatggtg gacggcagct ggggctgttg tccaatgcct   2400
caggctagct gctgcgagga cagagtgcac tgttgccctc acggcgcctt ttgcgatctg   2460
gtgcacaccc ggtgcatcac cccaacaggc acacatcctc tggccaagaa gctgcctgct   2520
cagcggacca atagagccgt ggctctgagc agcagcgtga tgtgccctga cgccagatcc   2580
aggtgtccag acgctccac atgttgcgaa ctgcccagcg gcaaatacgg ctgctgcccc   2640
atgcctaacg ccacatgctg tagcgaccat cttcactgct gcccacaaga caccgtgtgc   2700
```

-continued

```
gacctgatcc agagcaagtg cctgagcaaa gagaacgcca ccaccgacct gctgaccaaa    2760
ctgccagctc acaccgtggg agatgtgaag tgcgacatgg aagtgtcttg ccccgacggc    2820
tatacctgct gtagactgca atctggcgcc tggggctgct gcccttttac acaagctgtg    2880
tgttgcgagg accacatcca ttgctgccct gccggcttca cctgtgacac acagaaaggc    2940
acctgcgagc agggccctca tcaggtgcca tggatggaaa agcccctgc tcacctgagc     3000
ctgcctgatc ctcaagctct gaagagggac gtgccctgcg acaatgtgtc tagctgccct    3060
agcagcgaca cctgctgcca gctgacatct ggcgagtggg gctgctgtcc tataccagag    3120
gccgtgtgtt gttccgacca ccagcattgc tgtcccaag gctacacctg tgtggccgaa     3180
ggccaatgtc aacggggctc tgaaattgtg gccggcctgg aaaagatgcc cgccagaagg    3240
gcttctctgt ctcaccccg ggacatcggc tgcgaccagc acacatcttg tcctgtgggc     3300
cagacctgtt gtccctctct tggtggatcc tgggcttgct gtcagctgcc tcacgccgtg    3360
tgctgcgaag atagacaaca ctgctgtccc gccggataca cctgtaacgt gaaggccaga    3420
tcctgcgaga agaagtggt gtctgcccag cctgccacct tcctggctag aagtcctcac     3480
gtgggcgtga aggacgtgga gtgtggcgag gccacttct gccacgacaa tcagacatgc      3540
tgcagagaca accggcaagg ctgggcttgt tgcccatata gacagggcgt gtgctgtgcc    3600
gacagaaggc actgttgtcc agccggcttt agatgtgccg ccaggggcac aaagtgtctg    3660
agaagggaag ccctaggtg gacgcccct ctgagagatc ctgctctgag acagctgctc      3720
tgatgaggta cctctagagt cgacccgggc ggcctcgagg acggggtgaa ctacgcctga    3780
ggatccgatc tttttccctc tgccaaaaat tatggggaca tcatgaagcc ccttgagcat    3840
ctgacttctg ctaataaag gaaatttatt tcattgcaa tagtgtgttg gaattttttg      3900
tgtctctcac tcggaagcaa ttcgttgatc tgaatttcga ccacccataa tacccattac    3960
cctggtagat aagtagcatg gcgggttaat cattaactac aaggaacccc tagtgatgga    4020
gttggccact ccctctctgc gcgctcgctc gctcactgag gccgggcgac caaaggtcgc    4080
ccgacgcccg ggctttgccc gggcggcctc agtgagcgag cgagcgcgca g             4131
```

<210> SEQ ID NO 25
<211> LENGTH: 2208
<212> TYPE: DNA
<213> ORGANISM: Artificial sequence
<220> FEATURE:
<223> OTHER INFORMATION: AAV1 VP1 gene
<220> FEATURE:
<221> NAME/KEY: CDS
<222> LOCATION: (1)..(2208)

<400> SEQUENCE: 25

```
atg gct gcc gat ggt tat ctt cca gat tgg ctc gag gac aac ctc tct      48
Met Ala Ala Asp Gly Tyr Leu Pro Asp Trp Leu Glu Asp Asn Leu Ser
1               5                   10                  15 gag ggc att cgc gag tgg tgg gac ttg aaa cct gga gcc ccg aag ccc      96
Glu Gly Ile Arg Glu Trp Trp Asp Leu Lys Pro Gly Ala Pro Lys Pro
            20                  25                  30 aaa gcc aac cag caa aag cag gac gac ggc cgg ggt ctg gtg ctt cct     144
Lys Ala Asn Gln Gln Lys Gln Asp Asp Gly Arg Gly Leu Val Leu Pro
        35                  40                  45 ggc tac aag tac ctc gga ccc ttc aac gga ctc gac aag ggg gag ccc     192
Gly Tyr Lys Tyr Leu Gly Pro Phe Asn Gly Leu Asp Lys Gly Glu Pro
    50                  55                  60 gtc aac gcg gcg gac gca gcg gcc ctc gag cac gac aag gcc tac gac     240
```

|  |  |  |  |  |  |  |  |  |  |  |  |  |  |  |  |
|---|---|---|---|---|---|---|---|---|---|---|---|---|---|---|---|
|  | Val | Asn | Ala | Ala | Asp | Ala | Ala | Leu | Glu | His | Asp | Lys | Ala | Tyr | Asp |
|  | 65 |  |  |  | 70 |  |  |  |  | 75 |  |  |  |  | 80 |

```
cag cag ctc aaa gcg ggt gac aat ccg tac ctg cgg tat aac cac gcc      288
Gln Gln Leu Lys Ala Gly Asp Asn Pro Tyr Leu Arg Tyr Asn His Ala
            85                  90                  95 gac gcc gag ttt cag gag cgt ctg caa gaa gat acg tct ttt ggg ggc      336
Asp Ala Glu Phe Gln Glu Arg Leu Gln Glu Asp Thr Ser Phe Gly Gly
        100                 105                 110 aac ctc ggg cga gca gtc ttc cag gcc aag aag cgg gtt ctc gaa cct      384
Asn Leu Gly Arg Ala Val Phe Gln Ala Lys Lys Arg Val Leu Glu Pro
            115                 120                 125 ctc ggt ctg gtt gag gaa ggc gct aag acg gct cct gga aag aaa cgt      432
Leu Gly Leu Val Glu Glu Gly Ala Lys Thr Ala Pro Gly Lys Lys Arg
    130                 135                 140 ccg gta gag cag tcg cca caa gag cca gac tcc tcc tcg ggc atc ggc      480
Pro Val Glu Gln Ser Pro Gln Glu Pro Asp Ser Ser Ser Gly Ile Gly
145                 150                 155                 160 aag aca ggc cag cag ccc gct aaa aag aga ctc aat ttt ggt cag act      528
Lys Thr Gly Gln Gln Pro Ala Lys Lys Arg Leu Asn Phe Gly Gln Thr
                165                 170                 175 ggc gac tca gag tca gtc ccc gat cca caa cct ctc gga gaa cct cca      576
Gly Asp Ser Glu Ser Val Pro Asp Pro Gln Pro Leu Gly Glu Pro Pro
            180                 185                 190 gca acc ccc gct gct gtg gga cct act aca atg gct tca ggc ggt ggc      624
Ala Thr Pro Ala Ala Val Gly Pro Thr Thr Met Ala Ser Gly Gly Gly
        195                 200                 205 gca cca atg gca gac aat aac gaa ggc gcc gac gga gtg ggt aat gcc      672
Ala Pro Met Ala Asp Asn Asn Glu Gly Ala Asp Gly Val Gly Asn Ala
    210                 215                 220 tca gga aat tgg cat tgc gat tcc aca tgg ctg ggc gac aga gtc atc      720
Ser Gly Asn Trp His Cys Asp Ser Thr Trp Leu Gly Asp Arg Val Ile
225                 230                 235                 240 acc acc agc acc cgc acc tgg gcc ttg ccc acc tac aat aac cac ctc      768
Thr Thr Ser Thr Arg Thr Trp Ala Leu Pro Thr Tyr Asn Asn His Leu
                245                 250                 255 tac aag caa atc tcc agt gct tca acg ggg gcc agc aac gac aac cac      816
Tyr Lys Gln Ile Ser Ser Ala Ser Thr Gly Ala Ser Asn Asp Asn His
            260                 265                 270 tac ttc ggc tac agc acc ccc tgg ggg tat ttt gat ttc aac aga ttc      864
Tyr Phe Gly Tyr Ser Thr Pro Trp Gly Tyr Phe Asp Phe Asn Arg Phe
        275                 280                 285 cac tgc cac ttt tca cca cgt gac tgg cag cga ctc atc aac aac aat      912
His Cys His Phe Ser Pro Arg Asp Trp Gln Arg Leu Ile Asn Asn Asn
    290                 295                 300 tgg gga ttc cgg ccc aag aga ctc aac ttc aaa ctc ttc aac atc caa      960
Trp Gly Phe Arg Pro Lys Arg Leu Asn Phe Lys Leu Phe Asn Ile Gln
305                 310                 315                 320 gtc aag gag gtc acg acg aat gat ggc gtc aca acc atc gct aat aac     1008
Val Lys Glu Val Thr Thr Asn Asp Gly Val Thr Thr Ile Ala Asn Asn
                325                 330                 335 ctt acc agc acg gtt caa gtc ttc tcg gac tcg gag tac cag ctt ccg     1056
Leu Thr Ser Thr Val Gln Val Phe Ser Asp Ser Glu Tyr Gln Leu Pro
            340                 345                 350 tac gtc ctc ggc tct gcg cac cag ggc tgc ctc cct ccg ttc ccg gcg     1104
Tyr Val Leu Gly Ser Ala His Gln Gly Cys Leu Pro Pro Phe Pro Ala
        355                 360                 365 gac gtg ttc atg att ccg caa tac ggc tac ctg acg ctc aac aat ggc     1152
Asp Val Phe Met Ile Pro Gln Tyr Gly Tyr Leu Thr Leu Asn Asn Gly
    370                 375                 380
```

```
                                                   -continued agc caa gcc gtg gga cgt tca tcc ttt tac tgc ctg gaa tat ttc cct      1200
Ser Gln Ala Val Gly Arg Ser Ser Phe Tyr Cys Leu Glu Tyr Phe Pro
385             390                 395                 400 tct cag atg ctg aga acg ggc aac aac ttt acc ttc agc tac acc ttt      1248
Ser Gln Met Leu Arg Thr Gly Asn Asn Phe Thr Phe Ser Tyr Thr Phe
        405                 410                 415 gag gaa gtg cct ttc cac agc agc tac gcg cac agc cag agc ctg gac      1296
Glu Glu Val Pro Phe His Ser Ser Tyr Ala His Ser Gln Ser Leu Asp
                420                 425                 430 cgg ctg atg aat cct ctc atc gac caa tac ctg tat tac ctg aac aga      1344
Arg Leu Met Asn Pro Leu Ile Asp Gln Tyr Leu Tyr Tyr Leu Asn Arg
            435                 440                 445 act caa aat cag tcc gga agt gcc caa aac aag gac ttg ctg ttt agc      1392
Thr Gln Asn Gln Ser Gly Ser Ala Gln Asn Lys Asp Leu Leu Phe Ser
450                 455                 460 cgt ggg tct cca gct ggc atg tct gtt cag ccc aaa aac tgg cta cct      1440
Arg Gly Ser Pro Ala Gly Met Ser Val Gln Pro Lys Asn Trp Leu Pro
465             470                 475                 480 gga ccc tgt tat cgg cag cag cgc gtt tct aaa aca aaa aca gac aac      1488
Gly Pro Cys Tyr Arg Gln Gln Arg Val Ser Lys Thr Lys Thr Asp Asn
        485                 490                 495 aac aac agc aat ttt acc tgg act ggt gct tca aaa tat aac ctc aat      1536
Asn Asn Ser Asn Phe Thr Trp Thr Gly Ala Ser Lys Tyr Asn Leu Asn
                500                 505                 510 ggg cgt gaa tcc atc atc aac cct ggc act gct atg gcc tca cac aaa      1584
Gly Arg Glu Ser Ile Ile Asn Pro Gly Thr Ala Met Ala Ser His Lys
            515                 520                 525 gac gac gaa gac aag ttc ttt ccc atg agc ggt gtc atg att ttt gga      1632
Asp Asp Glu Asp Lys Phe Phe Pro Met Ser Gly Val Met Ile Phe Gly
530                 535                 540 aaa gag agc gcc gga gct tca aac act gca ttg gac aat gtc atg att      1680
Lys Glu Ser Ala Gly Ala Ser Asn Thr Ala Leu Asp Asn Val Met Ile
545             550                 555                 560 aca gac gaa gag gaa att aaa gcc act aac cct gtg gcc acc gaa aga      1728
Thr Asp Glu Glu Glu Ile Lys Ala Thr Asn Pro Val Ala Thr Glu Arg
        565                 570                 575 ttt ggg acc gtg gca gtc aat ttc cag agc agc agc aca gac cct gcg      1776
Phe Gly Thr Val Ala Val Asn Phe Gln Ser Ser Ser Thr Asp Pro Ala
                580                 585                 590 acc gga gat gtg cat gct atg gga gca tta cct ggc atg gtg tgg caa      1824
Thr Gly Asp Val His Ala Met Gly Ala Leu Pro Gly Met Val Trp Gln
            595                 600                 605 gat aga gac gtg tac ctg cag ggt ccc att tgg gcc aaa att cct cac      1872
Asp Arg Asp Val Tyr Leu Gln Gly Pro Ile Trp Ala Lys Ile Pro His
610                 615                 620 aca gat gga cac ttt cac ccg tct cct ctt atg ggc ggc ttt gga ctc      1920
Thr Asp Gly His Phe His Pro Ser Pro Leu Met Gly Gly Phe Gly Leu
625             630                 635                 640 aag aac ccg cct cct cag atc ctc atc aaa aac acg cct gtt cct gcg      1968
Lys Asn Pro Pro Pro Gln Ile Leu Ile Lys Asn Thr Pro Val Pro Ala
        645                 650                 655 aat cct ccg gcg gag ttt tca gct aca aag ttt gct tca ttc atc acc      2016
Asn Pro Pro Ala Glu Phe Ser Ala Thr Lys Phe Ala Ser Phe Ile Thr
                660                 665                 670 caa tac tcc aca gga caa gtg agt gtg gaa att gaa tgg gag ctg cag      2064
Gln Tyr Ser Thr Gly Gln Val Ser Val Glu Ile Glu Trp Glu Leu Gln
            675                 680                 685 aaa gaa aac agc aag cgc tgg aat ccc gaa gtg cag tac aca tcc aat      2112
Lys Glu Asn Ser Lys Arg Trp Asn Pro Glu Val Gln Tyr Thr Ser Asn
690                 695                 700
```

```
tat gca aaa tct gcc aac gtt gat ttt act gtg gac aac aat gga ctt    2160
Tyr Ala Lys Ser Ala Asn Val Asp Phe Thr Val Asp Asn Asn Gly Leu
705                 710                 715                 720 tat act gag cct cgc ccc att ggc acc cgt tac ctt acc cgt ccc ctg    2208
Tyr Thr Glu Pro Arg Pro Ile Gly Thr Arg Tyr Leu Thr Arg Pro Leu
            725                 730                 735

<210> SEQ ID NO 26
<211> LENGTH: 736
<212> TYPE: PRT
<213> ORGANISM: Artificial sequence
<220> FEATURE:
<223> OTHER INFORMATION: Synthetic Construct

<400> SEQUENCE: 26

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320
```

```
Val Lys Glu Val Thr Thr Asn Asp Gly Val Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

<210> SEQ ID NO 27
<211> LENGTH: 1863
<212> TYPE: DNA
<213> ORGANISM: Artificial sequence
<220> FEATURE:
<223> OTHER INFORMATION: AAV2 rep

<400> SEQUENCE: 27

```
atgccggggt tttacgagat tgtgattaag gtccccagcg accttgacga gcatctgccc      60
ggcatttctg acagctttgt gaactgggtg gccgagaagg aatgggagtt gccgccagat     120
tctgacatgg atctgaatct gattgagcag gcacccctga ccgtggccga gaagctgcag     180
cgcgactttc tgacggaatg gcgccgtgtg agtaaggccc cggaggctct tttctttgtg     240
caatttgaga agggagagag ctacttccac atgcacgtgc tcgtggaaac caccggggtg     300
aaatccatgg ttttgggacg tttcctgagt cagattcgcg aaaaactgat tcagagaatt     360
taccgcggga tcgagccgac tttgccaaac tggttcgcgg tcacaaagac cagaaatggc     420
gccgaggcg ggaacaaggt ggtggatgag tgctacatcc ccaattactt gctccccaaa      480
acccagcctg agctccagtg ggcgtggact aatatggaac agtatttaag cgcctgtttg     540
aatctcacgg agcgtaaacg gttggtggcg cagcatctga cgcacgtgtc gcagacgcag     600
gagcagaaca agagaatca gaatcccaat tctgatgcgc cggtgatcag atcaaaaact      660
tcagccaggt acatggagct ggtcgggtgg ctcgtggaca aggggattac ctcggagaag     720
cagtggatcc aggaggacca ggcctcatac atctccttca tgcggcctc caactcgcgg      780
tcccaaatca aggctgcctt ggacaatgcg ggaaagatta tgagcctgac taaaaccgcc     840
cccgactacc tggtgggcca gcagcccgtg gaggacattt ccagcaatcg gatttataaa     900
attttggaac taacgggta cgatccccaa tatgcggctt ccgtctttct gggatgggcc      960
acgaaaaagt tcggcaagag gaacaccatc tggctgtttg ggcctgcaac taccgggaag    1020
accaacatcg cggaggccat agcccacact gtgcccttct acgggtgcgt aaactggacc    1080
aatgagaact ttcccttcaa cgactgtgtc gacaagatgg tgatctggtg ggaggagggg    1140
aagatgaccg ccaaggtcgt ggagtcggcc aaagccattc tcggaggaag caaggtgcgc    1200
gtggaccaga aatgcaagtc ctcggcccag atagacccga ctcccgtgat cgtcacctcc    1260
aacaccaaca tgtgcgccgt gattgacggg aactcaacga ccttcgaaca ccagcagccg    1320
ttgcaagacc ggatgttcaa atttgaactc acccgccgtc tggatcatga ctttgggaag    1380
gtcaccaagc aggaagtcaa agactttttc cggtgggcaa aggatcacgt ggttgaggtg    1440
gagcatgaat tctacgtcaa aaagggtgga gccaagaaaa gacccgcccc cagtgacgca    1500
gatataagtg agcccaaacg ggtgcgcgag tcagttgcgc agccatcgac gtcagacgcg    1560
gaagcttcga tcaactacgc agacaggtac caaaacaaat gttctcgtca cgtgggcatg    1620
aatctgatgc tgtttccctg cagacaatgc gagagaatga tcagaattc aaatatctgc    1680
ttcactcacg gacagaaaga ctgtttagag tgctttcccg tgtcagaatc tcaacccgtt    1740
tctgtcgtca aaaaggcgta tcagaaactg tgctacattc atcatatcat gggaaaggtg    1800
ccagacgctt gcactgcctg cgatctggtc aatgtggatt tggatgactg catctttgaa    1860
caa                                                                   1863
```

<210> SEQ ID NO 28
<211> LENGTH: 2172
<212> TYPE: DNA
<213> ORGANISM: Artificial sequence
<220> FEATURE:

<223> OTHER INFORMATION: AAV5 capsid VP1 gene
<220> FEATURE:
<221> NAME/KEY: CDS
<222> LOCATION: (1)..(2172)

<400> SEQUENCE: 28

| | | | | | | | | | | | | | | | | |
|---|---|---|---|---|---|---|---|---|---|---|---|---|---|---|---|---|
| atg | tct | ttt | gtt | gat | cac | cct | cca | gat | tgg | ttg | gaa | gaa | gtt | ggt | gaa | 48 |
| Met | Ser | Phe | Val | Asp | His | Pro | Pro | Asp | Trp | Leu | Glu | Glu | Val | Gly | Glu | |
| 1 | | | | 5 | | | | | 10 | | | | | 15 | | |
| ggt | ctt | cgc | gag | ttt | ttg | ggc | ctt | gaa | gcg | ggc | cca | ccg | aaa | cca | aaa | 96 |
| Gly | Leu | Arg | Glu | Phe | Leu | Gly | Leu | Glu | Ala | Gly | Pro | Pro | Lys | Pro | Lys | |
| | | | 20 | | | | | 25 | | | | | 30 | | | |
| ccc | aat | cag | cag | cat | caa | gat | caa | gcc | cgt | ggt | ctt | gtg | ctg | cct | ggt | 144 |
| Pro | Asn | Gln | Gln | His | Gln | Asp | Gln | Ala | Arg | Gly | Leu | Val | Leu | Pro | Gly | |
| | 35 | | | | | 40 | | | | | 45 | | | | | |
| tat | aac | tat | ctc | gga | ccc | gga | aac | ggt | ctc | gat | cga | gga | gag | cct | gtc | 192 |
| Tyr | Asn | Tyr | Leu | Gly | Pro | Gly | Asn | Gly | Leu | Asp | Arg | Gly | Glu | Pro | Val | |
| 50 | | | | | 55 | | | | | 60 | | | | | | |
| aac | agg | gca | gac | gag | gtc | gcg | cga | gag | cac | gac | atc | tcg | tac | aac | gag | 240 |
| Asn | Arg | Ala | Asp | Glu | Val | Ala | Arg | Glu | His | Asp | Ile | Ser | Tyr | Asn | Glu | |
| 65 | | | | | 70 | | | | | 75 | | | | | 80 | |
| cag | ctt | gag | gcg | gga | gac | aac | ccc | tac | ctc | aag | tac | aac | cac | gcg | gac | 288 |
| Gln | Leu | Glu | Ala | Gly | Asp | Asn | Pro | Tyr | Leu | Lys | Tyr | Asn | His | Ala | Asp | |
| | | | | 85 | | | | | 90 | | | | | 95 | | |
| gcc | gag | ttt | cag | gag | aag | ctc | gcc | gac | gac | aca | tcc | ttc | ggg | gga | aac | 336 |
| Ala | Glu | Phe | Gln | Glu | Lys | Leu | Ala | Asp | Asp | Thr | Ser | Phe | Gly | Gly | Asn | |
| | | | 100 | | | | | 105 | | | | | 110 | | | |
| ctc | gga | aag | gca | gtc | ttt | cag | gcc | aag | aaa | agg | gtt | ctc | gaa | cct | ttt | 384 |
| Leu | Gly | Lys | Ala | Val | Phe | Gln | Ala | Lys | Lys | Arg | Val | Leu | Glu | Pro | Phe | |
| | | 115 | | | | | 120 | | | | | 125 | | | | |
| ggc | ctg | gtt | gaa | gag | ggt | gct | aag | acg | gcc | cct | acc | gga | aag | cgg | ata | 432 |
| Gly | Leu | Val | Glu | Glu | Gly | Ala | Lys | Thr | Ala | Pro | Thr | Gly | Lys | Arg | Ile | |
| 130 | | | | | 135 | | | | | 140 | | | | | | |
| gac | gac | cac | ttt | cca | aaa | aga | aag | aag | gcc | cgg | acc | gaa | gag | gac | tcc | 480 |
| Asp | Asp | His | Phe | Pro | Lys | Arg | Lys | Lys | Ala | Arg | Thr | Glu | Glu | Asp | Ser | |
| 145 | | | | 150 | | | | | 155 | | | | | 160 | | |
| aag | cct | tcc | acc | tcg | tca | gac | gcc | gaa | gct | gga | ccc | agc | gga | tcc | cag | 528 |
| Lys | Pro | Ser | Thr | Ser | Ser | Asp | Ala | Glu | Ala | Gly | Pro | Ser | Gly | Ser | Gln | |
| | | | | 165 | | | | | 170 | | | | | 175 | | |
| cag | ctg | caa | atc | cca | gcc | caa | cca | gcc | tca | agt | ttg | gga | gct | gat | aca | 576 |
| Gln | Leu | Gln | Ile | Pro | Ala | Gln | Pro | Ala | Ser | Ser | Leu | Gly | Ala | Asp | Thr | |
| | | | 180 | | | | | 185 | | | | | 190 | | | |
| atg | tct | gcg | gga | ggt | ggc | ggc | cca | ttg | ggc | gac | aat | aac | caa | ggt | gcc | 624 |
| Met | Ser | Ala | Gly | Gly | Gly | Gly | Pro | Leu | Gly | Asp | Asn | Asn | Gln | Gly | Ala | |
| | | 195 | | | | | 200 | | | | | 205 | | | | |
| gat | gga | gtg | ggc | aat | gcc | tcg | gga | gat | tgg | cat | tgc | gat | tcc | acg | tgg | 672 |
| Asp | Gly | Val | Gly | Asn | Ala | Ser | Gly | Asp | Trp | His | Cys | Asp | Ser | Thr | Trp | |
| 210 | | | | | 215 | | | | | 220 | | | | | | |
| atg | ggg | gac | aga | gtc | gtc | acc | aag | tcc | acc | cga | acc | tgg | gtg | ctg | ccc | 720 |
| Met | Gly | Asp | Arg | Val | Val | Thr | Lys | Ser | Thr | Arg | Thr | Trp | Val | Leu | Pro | |
| 225 | | | | 230 | | | | | 235 | | | | | 240 | | |
| agc | tac | aac | aac | cac | cag | tac | cga | gag | atc | aaa | agc | ggc | tcc | gtc | gac | 768 |
| Ser | Tyr | Asn | Asn | His | Gln | Tyr | Arg | Glu | Ile | Lys | Ser | Gly | Ser | Val | Asp | |
| | | | | 245 | | | | | 250 | | | | | 255 | | |
| gga | agc | aac | gcc | aac | gcc | tac | ttt | gga | tac | agc | acc | ccc | tgg | ggg | tac | 816 |
| Gly | Ser | Asn | Ala | Asn | Ala | Tyr | Phe | Gly | Tyr | Ser | Thr | Pro | Trp | Gly | Tyr | |
| | | | 260 | | | | | 265 | | | | | 270 | | | |
| ttt | gac | ttt | aac | cgc | ttc | cac | agc | cac | tgg | agc | ccc | cga | gac | tgg | caa | 864 |
| Phe | Asp | Phe | Asn | Arg | Phe | His | Ser | His | Trp | Ser | Pro | Arg | Asp | Trp | Gln | |
| | | 275 | | | | | 280 | | | | | 285 | | | | |

-continued

| | | |
|---|---|---|
| aga ctc atc aac aac tac tgg ggc ttc aga ccc cgg tcc ctc aga gtc<br>Arg Leu Ile Asn Asn Tyr Trp Gly Phe Arg Pro Arg Ser Leu Arg Val<br>290                      295                      300 | 912 |
| aaa atc ttc aac att caa gtc aaa gag gtc acg gtg cag gac tcc acc<br>Lys Ile Phe Asn Ile Gln Val Lys Glu Val Thr Val Gln Asp Ser Thr<br>305                      310                      315                      320 | 960 |
| acc acc atc gcc aac aac ctc acc tcc acc gtc caa gtg ttt acg gac<br>Thr Thr Ile Ala Asn Asn Leu Thr Ser Thr Val Gln Val Phe Thr Asp<br>                      325                      330                      335 | 1008 |
| gac gac tac cag ctg ccc tac gtc gtc ggc aac ggg acc gag gga tgc<br>Asp Asp Tyr Gln Leu Pro Tyr Val Val Gly Asn Gly Thr Glu Gly Cys<br>                340                      345                      350 | 1056 |
| ctg ccg gcc ttc cct ccg cag gtc ttt acg ctg ccg cag tac ggt tac<br>Leu Pro Ala Phe Pro Pro Gln Val Phe Thr Leu Pro Gln Tyr Gly Tyr<br>            355                      360                      365 | 1104 |
| gcg acg ctg aac cgc gac aac aca gaa aat ccc acc gag agg agc agc<br>Ala Thr Leu Asn Arg Asp Asn Thr Glu Asn Pro Thr Glu Arg Ser Ser<br>370                      375                      380 | 1152 |
| ttc ttc tgc cta gag tac ttt ccc agc aag atg ctg aga acg ggc aac<br>Phe Phe Cys Leu Glu Tyr Phe Pro Ser Lys Met Leu Arg Thr Gly Asn<br>385                      390                      395                      400 | 1200 |
| aac ttt gag ttt acc tac aac ttt gag gag gtg ccc ttc cac tcc agc<br>Asn Phe Glu Phe Thr Tyr Asn Phe Glu Glu Val Pro Phe His Ser Ser<br>                      405                      410                      415 | 1248 |
| ttc gct ccc agt cag aac ctc ttc aag ctg gcc aac ccg ctg gtg gac<br>Phe Ala Pro Ser Gln Asn Leu Phe Lys Leu Ala Asn Pro Leu Val Asp<br>            420                      425                      430 | 1296 |
| cag tac ttg tac cgc ttc gtg agc aca aat aac act ggc gga gtc cag<br>Gln Tyr Leu Tyr Arg Phe Val Ser Thr Asn Asn Thr Gly Gly Val Gln<br>        435                      440                      445 | 1344 |
| ttc aac aag aac ctg gcc ggg aga tac gcc aac acc tac aaa aac tgg<br>Phe Asn Lys Asn Leu Ala Gly Arg Tyr Ala Asn Thr Tyr Lys Asn Trp<br>450                      455                      460 | 1392 |
| ttc ccg ggg ccc atg ggc cga acc cag ggc tgg aac ctg ggc tcc ggg<br>Phe Pro Gly Pro Met Gly Arg Thr Gln Gly Trp Asn Leu Gly Ser Gly<br>465                      470                      475                      480 | 1440 |
| gtc aac cgc gcc agt gtc agc gcc ttc gcc acg acc aat agg atg gag<br>Val Asn Arg Ala Ser Val Ser Ala Phe Ala Thr Thr Asn Arg Met Glu<br>                      485                      490                      495 | 1488 |
| ctc gag ggc gcg agt tac cag gtg ccc ccg cag ccg aac ggc atg acc<br>Leu Glu Gly Ala Ser Tyr Gln Val Pro Pro Gln Pro Asn Gly Met Thr<br>            500                      505                      510 | 1536 |
| aac aac ctc cag ggc agc aac acc tat gcc ctg gag aac act atg atc<br>Asn Asn Leu Gln Gly Ser Asn Thr Tyr Ala Leu Glu Asn Thr Met Ile<br>        515                      520                      525 | 1584 |
| ttc aac agc cag ccg gcg aac ccg ggc acc acc gcc acg tac ctc gag<br>Phe Asn Ser Gln Pro Ala Asn Pro Gly Thr Thr Ala Thr Tyr Leu Glu<br>530                      535                      540 | 1632 |
| ggc aac atg ctc atc acc agc gag agc gag acg cag ccg gtg aac cgc<br>Gly Asn Met Leu Ile Thr Ser Glu Ser Glu Thr Gln Pro Val Asn Arg<br>545                      550                      555                      560 | 1680 |
| gtg gcg tac aac gtc ggc ggg cag atg gcc acc aac aac cag agc tcc<br>Val Ala Tyr Asn Val Gly Gly Gln Met Ala Thr Asn Asn Gln Ser Ser<br>                      565                      570                      575 | 1728 |
| acc act gcc ccc gcg acc ggc acg tac aac ctc cag gaa atc gtg ccc<br>Thr Thr Ala Pro Ala Thr Gly Thr Tyr Asn Leu Gln Glu Ile Val Pro<br>            580                      585                      590 | 1776 |
| ggc agc gtg tgg atg gag agg gac gtg tac ctc caa gga ccc atc tgg<br>Gly Ser Val Trp Met Glu Arg Asp Val Tyr Leu Gln Gly Pro Ile Trp<br>595                      600                      605 | 1824 |

```
gcc aag atc cca gag acg ggg gcg cac ttt cac ccc tct ccg gcc atg    1872
Ala Lys Ile Pro Glu Thr Gly Ala His Phe His Pro Ser Pro Ala Met
    610             615                 620 ggc gga ttc gga ctc aaa cac cca ccg ccc atg atg ctc atc aag aac    1920
Gly Gly Phe Gly Leu Lys His Pro Pro Pro Met Met Leu Ile Lys Asn
625                 630                 635                 640 acg cct gtg ccc gga aat atc acc agc ttc tcg gac gtg ccc gtc agc    1968
Thr Pro Val Pro Gly Asn Ile Thr Ser Phe Ser Asp Val Pro Val Ser
                645                 650                 655 agc ttc atc acc cag tac agc acc ggg cag gtc acc gtg gag atg gag    2016
Ser Phe Ile Thr Gln Tyr Ser Thr Gly Gln Val Thr Val Glu Met Glu
            660                 665                 670 tgg gag ctc aag aag gaa aac tcc aag agg tgg aac cca gag atc cag    2064
Trp Glu Leu Lys Lys Glu Asn Ser Lys Arg Trp Asn Pro Glu Ile Gln
        675                 680                 685 tac aca aac aac tac aac gac ccc cag ttt gtg gac ttt gcc ccg gac    2112
Tyr Thr Asn Asn Tyr Asn Asp Pro Gln Phe Val Asp Phe Ala Pro Asp
    690                 695                 700 agc acc ggg gaa tac aga acc acc aga cct atc gga acc cga tac ctt    2160
Ser Thr Gly Glu Tyr Arg Thr Thr Arg Pro Ile Gly Thr Arg Tyr Leu
705                 710                 715                 720 acc cga ccc ctt                                                    2172
Thr Arg Pro Leu <210> SEQ ID NO 29
<211> LENGTH: 724
<212> TYPE: PRT
<213> ORGANISM: Artificial sequence
<220> FEATURE:
<223> OTHER INFORMATION: Synthetic Construct

<400> SEQUENCE: 29

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
```

```
            195                 200                 205
Asp Gly Val Gly Asn Ala Ser Gly Asp Trp His Cys Asp Ser Thr Trp
210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
                260                 265                 270

Phe Asp Phe Asn Arg Phe His Ser His Trp Ser Pro Arg Asp Trp Gln
            275                 280                 285

Arg Leu Ile Asn Asn Tyr Trp Gly Phe Arg Pro Arg Ser Leu Arg Val
            290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
                340                 345                 350

Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
            370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
                420                 425                 430

Gln Tyr Leu Tyr Arg Phe Val Ser Thr Asn Asn Thr Gly Gly Val Gln
            435                 440                 445

Phe Asn Lys Asn Leu Ala Gly Arg Tyr Ala Asn Thr Tyr Lys Asn Trp
            450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
                500                 505                 510

Asn Asn Leu Gln Gly Ser Asn Thr Tyr Ala Leu Glu Asn Thr Met Ile
            515                 520                 525

Phe Asn Ser Gln Pro Ala Asn Pro Gly Thr Thr Ala Thr Tyr Leu Glu
            530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
                580                 585                 590

Gly Ser Val Trp Met Glu Arg Asp Val Tyr Leu Gln Gly Pro Ile Trp
            595                 600                 605

Ala Lys Ile Pro Glu Thr Gly Ala His Phe His Pro Ser Pro Ala Met
            610                 615                 620
```

```
Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
                660                 665                 670

Trp Glu Leu Lys Lys Glu Asn Ser Lys Arg Trp Asn Pro Glu Ile Gln
                675                 680                 685

Tyr Thr Asn Asn Tyr Asn Asp Pro Gln Phe Val Asp Phe Ala Pro Asp
                690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 30
<211> LENGTH: 2211
<212> TYPE: DNA
<213> ORGANISM: Artificial sequence
<220> FEATURE:
<223> OTHER INFORMATION: AAVhu68 VP1 capsid
<220> FEATURE:
<221> NAME/KEY: CDS
<222> LOCATION: (1)..(2211)

<400> SEQUENCE: 30 atg gct gcc gat ggt tat ctt cca gat tgg ctc gag gac aac ctc agt     48
Met Ala Ala Asp Gly Tyr Leu Pro Asp Trp Leu Glu Asp Asn Leu Ser
1               5                   10                  15 gaa ggc att cgc gag tgg tgg gct ttg aaa cct gga gcc cct caa ccc     96
Glu Gly Ile Arg Glu Trp Trp Ala Leu Lys Pro Gly Ala Pro Gln Pro
                20                  25                  30 aag gca aat caa caa cat caa gac aac gct cgg ggt ctt gtg ctt ccg    144
Lys Ala Asn Gln Gln His Gln Asp Asn Ala Arg Gly Leu Val Leu Pro
            35                  40                  45 ggt tac aaa tac ctt gga ccc ggc aac gga ctc gac aag ggg gag ccg    192
Gly Tyr Lys Tyr Leu Gly Pro Gly Asn Gly Leu Asp Lys Gly Glu Pro
        50                  55                  60 gtc aac gaa gca gac gcg gcg gcc ctc gag cac gac aag gcc tac gac    240
Val Asn Glu Ala Asp Ala Ala Ala Leu Glu His Asp Lys Ala Tyr Asp
65                  70                  75                  80 cag cag ctc aag gcc gga gac aac ccg tac ctc aag tac aac cac gcc    288
Gln Gln Leu Lys Ala Gly Asp Asn Pro Tyr Leu Lys Tyr Asn His Ala
                85                  90                  95 gac gcc gag ttc cag gag cgg ctc aaa gaa gat acg tct ttt ggg ggc    336
Asp Ala Glu Phe Gln Glu Arg Leu Lys Glu Asp Thr Ser Phe Gly Gly
                100                 105                 110 aac ctc ggg cga gca gtc ttc cag gcc aaa aag agg ctt ctt gaa cct    384
Asn Leu Gly Arg Ala Val Phe Gln Ala Lys Lys Arg Leu Leu Glu Pro
            115                 120                 125 ctt ggt ctg gtt gag gaa gcg gct aag acg gct cct gga aag aag agg    432
Leu Gly Leu Val Glu Glu Ala Ala Lys Thr Ala Pro Gly Lys Lys Arg
        130                 135                 140 cct gta gag cag tct cct cag gaa ccg gac tcc tcc gtg ggt att ggc    480
Pro Val Glu Gln Ser Pro Gln Glu Pro Asp Ser Ser Val Gly Ile Gly
145                 150                 155                 160 aaa tcg ggt gca cag ccc gct aaa aag aga ctc aat ttc ggt cag act    528
Lys Ser Gly Ala Gln Pro Ala Lys Lys Arg Leu Asn Phe Gly Gln Thr
                165                 170                 175 ggc gac aca gag tca gtc ccc gac cct caa cca atc gga gaa cct ccc    576
```

```
                Gly Asp Thr Glu Ser Val Pro Asp Pro Gln Pro Ile Gly Glu Pro Pro
                                180                 185                 190 gca gcc ccc tca ggt gtg gga tct ctt aca atg gct tca ggt ggt ggc              624
Ala Ala Pro Ser Gly Val Gly Ser Leu Thr Met Ala Ser Gly Gly Gly
        195                 200                 205 gca cca gtg gca gac aat aac gaa ggt gcc gat gga gtg ggt agt tcc              672
Ala Pro Val Ala Asp Asn Asn Glu Gly Ala Asp Gly Val Gly Ser Ser
210                 215                 220 tcg gga aat tgg cat tgc gat tcc caa tgg ctg ggg gac aga gtc atc              720
Ser Gly Asn Trp His Cys Asp Ser Gln Trp Leu Gly Asp Arg Val Ile
225                 230                 235                 240 acc acc agc acc cga acc tgg gcc ctg ccc acc tac aac aat cac ctc              768
Thr Thr Ser Thr Arg Thr Trp Ala Leu Pro Thr Tyr Asn Asn His Leu
                245                 250                 255 tac aag caa atc tcc aac agc aca tct gga gga tct tca aat gac aac              816
Tyr Lys Gln Ile Ser Asn Ser Thr Ser Gly Gly Ser Ser Asn Asp Asn
        260                 265                 270 gcc tac ttc ggc tac agc acc ccc tgg ggg tat ttt gac ttc aac aga              864
Ala Tyr Phe Gly Tyr Ser Thr Pro Trp Gly Tyr Phe Asp Phe Asn Arg
    275                 280                 285 ttc cac tgc cac ttc tca cca cgt gac tgg caa aga ctc atc aac aac              912
Phe His Cys His Phe Ser Pro Arg Asp Trp Gln Arg Leu Ile Asn Asn
290                 295                 300 aac tgg gga ttc cgg cct aag cga ctc aac ttc aag ctc ttc aac att              960
Asn Trp Gly Phe Arg Pro Lys Arg Leu Asn Phe Lys Leu Phe Asn Ile
305                 310                 315                 320 cag gtc aaa gag gtt acg gac aac aat gga gtc aag acc atc gct aat             1008
Gln Val Lys Glu Val Thr Asp Asn Asn Gly Val Lys Thr Ile Ala Asn
                325                 330                 335 aac ctt acc agc acg gtc cag gtc ttc acg gac tca gac tat cag ctc             1056
Asn Leu Thr Ser Thr Val Gln Val Phe Thr Asp Ser Asp Tyr Gln Leu
        340                 345                 350 ccg tac gtg ctc ggg tcg gct cac gag ggc tgc ctc ccg ccg ttc cca             1104
Pro Tyr Val Leu Gly Ser Ala His Glu Gly Cys Leu Pro Pro Phe Pro
    355                 360                 365 gcg gac gtt ttc atg att cct cag tac ggg tat cta acg ctt aat gat             1152
Ala Asp Val Phe Met Ile Pro Gln Tyr Gly Tyr Leu Thr Leu Asn Asp
370                 375                 380 gga agc caa gcc gtg ggt cgt tcc tcc ttt tac tgc ctg gaa tat ttc             1200
Gly Ser Gln Ala Val Gly Arg Ser Ser Phe Tyr Cys Leu Glu Tyr Phe
385                 390                 395                 400 ccg tcg caa atg cta aga acg ggt aac aac ttc cag ttc agc tac gag             1248
Pro Ser Gln Met Leu Arg Thr Gly Asn Asn Phe Gln Phe Ser Tyr Glu
                405                 410                 415 ttt gag aac gta cct ttc cat agc agc tat gct cac agc caa agc ctg             1296
Phe Glu Asn Val Pro Phe His Ser Ser Tyr Ala His Ser Gln Ser Leu
        420                 425                 430 gac cga ctc atg aat cca ctc atc gac caa tac ttg tac tat ctc tca             1344
Asp Arg Leu Met Asn Pro Leu Ile Asp Gln Tyr Leu Tyr Tyr Leu Ser
    435                 440                 445 aag act att aac ggt tct gga cag aat caa caa acg cta aaa ttc agt             1392
Lys Thr Ile Asn Gly Ser Gly Gln Asn Gln Gln Thr Leu Lys Phe Ser
450                 455                 460 gtg gcc gga ccc agc aac atg gct gtc cag gga aga aac tac ata cct             1440
Val Ala Gly Pro Ser Asn Met Ala Val Gln Gly Arg Asn Tyr Ile Pro
465                 470                 475                 480 gga ccc agc tac cga caa caa cgt gtc tca acc act gtg act caa aac             1488
Gly Pro Ser Tyr Arg Gln Gln Arg Val Ser Thr Thr Val Thr Gln Asn
                485                 490                 495
```

| | | |
|---|---|---|
| aac aac agc gaa ttt gct tgg cct gga gct tct tct tgg gct ctc aat<br>Asn Asn Ser Glu Phe Ala Trp Pro Gly Ala Ser Ser Trp Ala Leu Asn<br>500 505 510 | | 1536 |
| gga cgt aat agc ttg atg aat cct gga cct gct atg gcc agc cac aaa<br>Gly Arg Asn Ser Leu Met Asn Pro Gly Pro Ala Met Ala Ser His Lys<br>515 520 525 | | 1584 |
| gaa gga gag gac cgt ttc ttt cct ttg tct gga tct tta att ttt ggc<br>Glu Gly Glu Asp Arg Phe Phe Pro Leu Ser Gly Ser Leu Ile Phe Gly<br>530 535 540 | | 1632 |
| aaa caa gga act gga aga gac aac gtg gat gcg gac aaa gtc atg ata<br>Lys Gln Gly Thr Gly Arg Asp Asn Val Asp Ala Asp Lys Val Met Ile<br>545 550 555 560 | | 1680 |
| acc aac gaa gaa gaa att aaa act acc aac cca gta gca acg gag tcc<br>Thr Asn Glu Glu Glu Ile Lys Thr Thr Asn Pro Val Ala Thr Glu Ser<br>565 570 575 | | 1728 |
| tat gga caa gtg gcc aca aac cac cag agt gcc caa gca cag gcg cag<br>Tyr Gly Gln Val Ala Thr Asn His Gln Ser Ala Gln Ala Gln Ala Gln<br>580 585 590 | | 1776 |
| acc ggc tgg gtt caa aac caa gga ata ctt ccg ggt atg gtt tgg cag<br>Thr Gly Trp Val Gln Asn Gln Gly Ile Leu Pro Gly Met Val Trp Gln<br>595 600 605 | | 1824 |
| gac aga gat gtg tac ctg caa gga ccc att tgg gcc aaa att cct cac<br>Asp Arg Asp Val Tyr Leu Gln Gly Pro Ile Trp Ala Lys Ile Pro His<br>610 615 620 | | 1872 |
| acg gac ggc aac ttt cac cct tct ccg ctg atg gga ggg ttt gga atg<br>Thr Asp Gly Asn Phe His Pro Ser Pro Leu Met Gly Gly Phe Gly Met<br>625 630 635 640 | | 1920 |
| aag cac ccg cct cct cag atc ctc atc aaa aac aca cct gta cct gcg<br>Lys His Pro Pro Pro Gln Ile Leu Ile Lys Asn Thr Pro Val Pro Ala<br>645 650 655 | | 1968 |
| gat cct cca acg gct ttc aac aag gac aag ctg aac tct ttc atc acc<br>Asp Pro Pro Thr Ala Phe Asn Lys Asp Lys Leu Asn Ser Phe Ile Thr<br>660 665 670 | | 2016 |
| cag tat tct act ggc caa gtc agc gtg gag att gag tgg gag ctg cag<br>Gln Tyr Ser Thr Gly Gln Val Ser Val Glu Ile Glu Trp Glu Leu Gln<br>675 680 685 | | 2064 |
| aag gaa aac agc aag cgc tgg aac ccg gag atc cag tac act tcc aac<br>Lys Glu Asn Ser Lys Arg Trp Asn Pro Glu Ile Gln Tyr Thr Ser Asn<br>690 695 700 | | 2112 |
| tat tac aag tct aat aat gtt gaa ttt gct gtt aat act gaa ggt gtt<br>Tyr Tyr Lys Ser Asn Asn Val Glu Phe Ala Val Asn Thr Glu Gly Val<br>705 710 715 720 | | 2160 |
| tat tct gaa ccc cgc ccc att ggc acc aga tac ctg act cgt aat ctg<br>Tyr Ser Glu Pro Arg Pro Ile Gly Thr Arg Tyr Leu Thr Arg Asn Leu<br>725 730 735 | | 2208 |
| taa | | 2211 |

<210> SEQ ID NO 31
<211> LENGTH: 736
<212> TYPE: PRT
<213> ORGANISM: Artificial sequence
<220> FEATURE:
<223> OTHER INFORMATION: Synthetic Construct

<400> SEQUENCE: 31

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro

-continued

```
                35                  40                  45
Gly Tyr Lys Tyr Leu Gly Pro Gly Asn Gly Leu Asp Lys Gly Glu Pro
 50                  55                  60

Val Asn Glu Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Val Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460
```

```
Val Ala Gly Pro Ser Asn Met Ala Val Gln Gly Arg Asn Tyr Ile Pro
465                 470                 475                 480

Gly Pro Ser Tyr Arg Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735
```

<210> SEQ ID NO 32
<211> LENGTH: 22
<212> TYPE: DNA
<213> ORGANISM: Artificial Sequence
<220> FEATURE:
<223> OTHER INFORMATION: miRNA target sequence

<400> SEQUENCE: 32
agtgaattct accagtgcca ta                                          22

<210> SEQ ID NO 33
<211> LENGTH: 23
<212> TYPE: DNA
<213> ORGANISM: Artificial Sequence
<220> FEATURE:
<223> OTHER INFORMATION: miRNA target sequence

<400> SEQUENCE: 33
agcaaaaatg tgctagtgcc aaa                                         23

<210> SEQ ID NO 34
<211> LENGTH: 24

```
<212> TYPE: DNA
<213> ORGANISM: Artificial Sequence
<220> FEATURE:
<223> OTHER INFORMATION: miRNA target sequence

<400> SEQUENCE: 34
agtgtgagtt ctaccattgc caaa                                              24

<210> SEQ ID NO 35
<211> LENGTH: 23
<212> TYPE: DNA
<213> ORGANISM: Artificial Sequence
<220> FEATURE:
<223> OTHER INFORMATION: miRNA target sequence

<400> SEQUENCE: 35
agggattcct gggaaaactg gac                                               23
```

RECOMBINANT ADENO-ASSOCIATED VIRUS FOR TREATMENT OF GRN-ASSOCIATED ADULT-ONSET NEURODEGENERATION

CROSS-REFERENCE TO RELATED APPLICATIONS

This application is a National Stage Entry under 35 U.S.C. 371 of International Patent Application No. PCT/US2020/019149, filed Feb. 21, 2020, which claims priority to U.S. Provisional Patent Application No. 62/969,108, filed Feb. 2, 2020, U.S. Provisional Patent Application No. 62/923,812, filed Oct. 21, 2019, and U.S. Provisional Patent Application No. 62/809,329, filed Feb. 22, 2019, which are incorporated herein by reference.

BACKGROUND OF THE INVENTION

Frontotemporal dementia (FTD) is a fatal neurodegenerative disease that typically presents in the sixth or seventh decade of life with deficits in executive function, behavior, speech, or language comprehension. These symptoms are associated with a characteristic pattern of brain atrophy affecting the frontal and temporal cortices. Patients universally exhibit a progressive course, with an average survival of 8 years from symptom onset (Coyle-Gilchrist I T, et al. Neurology. 2016; 86(18):1736-43).

FTD is highly heritable, with approximately 40% of patients having a positive family history (Rohrer J D, et al. Neurology. 2009; 73(18):1451-6.). In 5-10% of FTD patients, pathogenic loss-of-function mutations can be identified in the granulin (GRN) gene encoding progranulin (PGRN), a ubiquitous lysosomal protein (Rohrer J D, et al. Neurology. 2009; 73(18):1451-6). GRN mutation carriers exhibit rapid and widespread brain atrophy and may present with clinical features of other neurodegenerative diseases, such as progressive supranuclear palsy, corticobasal syndrome, Parkinson's disease, dementia with Lewy bodies, or Alzheimer's disease (Le Ber I, et al. Brain: a journal of neurology. 2008; 131(3):732-46.). GRN mutations are inherited in an autosomal dominant fashion with greater than 90% penetrance by age 70 (Gass J, et al. Human molecular genetics. 2006; 15(20):2988-3001). While inheritance of a single GRN mutation causes FTD and other late-onset neurodegenerative diseases, patients with homozygous loss-of-function mutations present much earlier in life with neuronal ceroid lipofuscinosis (NCL, Batten disease), characterized by accumulation of autofluorescent material (lipofuscin) in the lysosomes of neurons, rapid cognitive decline and retinal degeneration (Smith Katherine R, et al. American Journal of Human Genetics. 2012; 90(6):1102-7). Though patients heterozygous for GRN mutations have much later symptom onset, they ultimately develop lysosomal storage lesions in the brain and retina identical to those of NCL patients, and likewise experience progressive neurodegeneration (Ward M E, et al. Science Translational Medicine. 2017; 9(385); Gotzl J K, et al. Acta neuropathologica. 2014; 127(6):845-60). Progranulin was recently found to play a critical role in lysosomal function by promoting lysosome acidification and serving as a chaperone for lysosomal proteases including cathepsin D (CTSD) (Beel S, et al. Human molecular genetics. 2017 Aug. 1; 26(15):2850-2863; Tanaka Y, et al. Human molecular genetics. 2017; 26(5):969-88). Mutations in the gene encoding CTSD also result in an NCL phenotype, supporting common pathophysiology related to deficient lysosomal protease activity (Siintola E, et al. Brain: a journal of neurology. 2006; 129(Pt 6):1438-45).

There are currently no disease modifying therapies for adult-onset neurodegeneration caused by GRN haploinsufficiency. Disease management includes supportive care and off-label treatments aimed at reducing disease-associated behavioral, cognitive, and/or movement symptoms (Tsai and Boxer, 2016, J Neurochem. 138 Suppl 1:211-21). Further, more patients may be reached at an earlier stage with screening individuals with a family history of dementia, which is currently not indicated in view of the lack of treatment. Thus, this disease spectrum represents an area of high unmet medical need.

What are needed are treatments for adult-onset neurodegenerative disorders associated with GRN haploinsufficiencies, and for the symptoms associated therewith.

SUMMARY OF THE INVENTION

A recombinant AAV (rAAV) suitable for use in treating neurodegeneration caused by progranulin (PGRN)-related frontotemporal dementia (FTD) and other adult-onset neurodegenerative disorders associated with GRN haploinsufficiencies are provided. The rAAV comprises an adeno-associated virus 1 capsid and a vector genome packaged in the AAV capsid, said vector genome comprising AAV inverted terminal repeats (ITRs), a coding sequence encoding a human progranulin, and regulatory sequences which direct expression of the progranulin. In certain embodiments, the vector genome comprises an AAV 5' inverted terminal repeat (ITR), a human PGRN coding sequence and regulatory elements which direct its expression, and an AAV 5' ITR.

A pharmaceutical composition comprising an aqueous liquid and a recombinant AAV (rAAV) is also provided. In certain embodiments, the aqueous liquid comprises an artificial cerebrospinal fluid with a surfactant, which are suitable for intrathecal administration.

A method of treating a human patient with progranulin-related frontotemporal dementia (FTD) neurodegeneration or another adult onset neurodegeneration disease caused by GRN haploinsufficiency is provided. The method comprises delivering a rAAV including a human progranulin coding sequence to the central nervous system (CNS). The recombinant adeno-associated virus (rAAV) having an adeno-associated virus 1 (AAV1) capsid, said rAAV further comprising a vector genome packaged in the AAV capsid, said vector genome comprising AAV inverted terminal repeats, a coding sequence for human progranulin, and regulatory sequences which direct expression of the progranulin.

A rAAV1.hPGRN for use in a method for treating a human patient with PGRN-FTD or another adult onset neurodegeneration disease caused by GRN haploinsufficiency is provided. The method comprises administering to the CNS a rAAV having an adeno-associated virus 1 capsid encoding human progranulin which targets ependymal cells. The rAAV1 further comprises a vector genome packaged in the AAV capsid, said vector genome comprising AAV inverted terminal repeats, a coding sequence for human progranulin, and regulatory sequences which direct expression of the progranulin in the ependymal cells. In one embodiment, a secretable human progranulin is expressed following delivery of the rAAV1 gene therapy.

A method for treating a human patient with brain lesions associated with progranulin-related frontotemporal dementia (FTD) neurodegeneration or another adult onset neurodegeneration disease caused by GRN haploinsufficiency is provided. The method comprises administering to the central nervous system (CNS) a recombinant adeno-associated virus (rAAV) having an adeno-associated virus 1 (AAV1) capsid, said rAAV further comprising a vector genome packaged in the AAV capsid, said vector genome comprising AAV inverted terminal repeats, a coding sequence for human progranulin, and regulatory sequences which direct expression of the progranulin.

In certain embodiments, the methods provided herein may further comprises (a) non-invasively assessing the patient for reduction in retinal storage lesions as a predictor of reduction of brain lesions, (b) performing magnetic resonance imaging to assess brain volume, and/or (c) measuring concentration of progranulin concentration in the CSF.

These and other aspects of the invention will be apparent from the following detailed description of the invention.

BRIEF DESCRIPTION OF THE DRAWINGS

FIG. 3A-FIG. 3D provide a natural history of lipofuscin accumulation and hexosaminidase activity in brains of $GRN^{-/-}$ mice. $GRN^{-/-}$ mice (KO) or $GRN^{+/+}$ (WT) controls were sacrificed at the ages indicated (n=10 per time point). Unstained brain sections were imaged for autofluorescent material (lipofuscin) in hippocampus, thalamus and frontal cortex, and lipofuscin deposits were quantified by three blinded reviewers and averaged (FIG. 3A-FIG. 3C). Lipofuscin counts are expressed relative to the total area of the region of interest. Hexosaminidase activity was measured in brain samples and normalized to total protein concentration (FIG. 3D). Values are expressed as a ratio to wild-type controls.

FIG. 4A-FIG. 4G show correction of lysosomal pathology in brains of young adult $GRN^{-/-}$ mice by AAV-mediated PGRN expression. $GRN^{-/-}$ mice (KO) or $GRN^{+/+}$ (WT) controls were treated with a single ICV injection of vehicle (PBS) or an AAVhu68 vector expressing human PGRN ($10^{11}$ GC) at 2 months of age (n=10 per group). Animals were sacrificed 60 days after injection, and human PGRN was measured in CSF (FIG. 4A) and frontal lobes of the brain (FIG. 4B) by ELISA. Hexosaminidase activity was measured in brain samples (FIG. 4C). Brain PGRN concentration and Hex activity were normalized to total protein. Unstained brain sections were imaged for autofluorescent material (lipofuscin) in hippocampus, thalamus and frontal cortex. Lipofuscin deposits in hippocampus, thalamus and frontal cortex were quantified by a blinded reviewer (FIG. 4D-FIG. 4G). Lipofuscin counts are expressed per high power field. N=10 per group except KO+PBS hippocampus n=8. *$p<0.05$, $p<0.005$, *$p<0.001$, ****$p<0.0001$, one-way ANOVA followed by Tukey's multiple comparisons test. Hexosaminidase activity was measured in serum (FIG. 4G).

In FIG. 7A and FIG. 7B, the dotted lines refer to limit of quantification for hPGRN in CSF at 1:5 dilution.

FIG. 8A-FIG. 8C show the immune response to human PGRN in vector treated nonhuman primates. Following ICM administered of AAV1, AAV5 or AAVhu68 vectors ($3\times10^{13}$ GC) expressing human PGRN from a chicken beta actin promoter or a ubiquitin C promoter (AAVhu68 V2) CSF was collected weekly for analysis of chemistry and cytology. Increased leukocyte counts (predominantly small lymphocytes) were evident in most animals (FIG. 8A). Antibody responses to human PGRN were measured by ELISA in CSF (FIG. 8B) and serum (FIG. 8C) of animals treated with AAVhu68 or AAV1. Antibodies against human PGRN were not evaluated in serum or CSF samples from animals treated with AAV5.

FIG. 10 provides a table showing percent neuron, astrocyte and oligodendrocyte transduction following ICM administration of AAV1 (animal ID 1826 and 2068) and AAVhu68 (animal ID 1518 and 2076) vectors to nonhuman primates. Adult rhesus macaques were administered $3 \times 10^{13}$ GC AAVhu68 (n=2) or AAV1 (n=2) vectors expressing GFP from a chicken beta actin promoter by ICM injection on study day 0 Animals were necropsied 28 days after vector administration, and sections of five regions of the right hemisphere of the brain were analyzed by GFP immunofluorescence with costaining for specific cell types (NeuN, GFAP and Olig2). Total cells of each cell type and the number of GFP expressing cells of each type were quantified using HALO software. The percentage of each cell type transduced is shown for each region. For some animals two sections were analyzed from region 5.

DETAILED DESCRIPTION OF THE INVENTION

Figure 1:
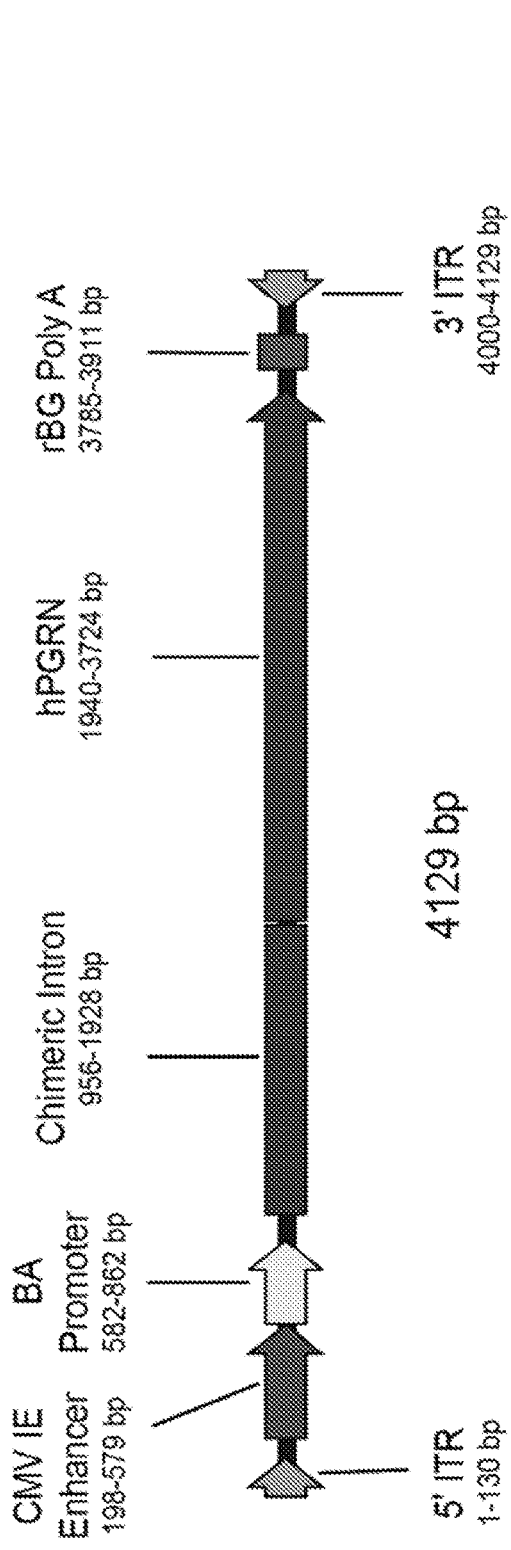
FIG. 1 is a linear map of an AAV1.hPGRN vector genome. The AAV1.CB7.CI.hPGRN.rBG vector genome comprises a coding sequence for human PGRN under the control of the ubiquitous CB7 promoter, which is composed of a hybrid between a CMV IE enhancer and a chicken β-actin promoter. Abbreviations: BA, β-actin; bp, base pairs; CMV IE, cytomegalovirus immediate-early; ITR, inverted terminal repeats; PolyA, polyadenylation; rBG, rabbit β-globin.

A recombinant AAV (rAAV) suitable for use in treating neurodegenerative conditions associated with GRN-haploinsufficiencies, such as progranulin (PGRN)-related frontal temporal dementia (FTD), and compositions containing the same are provided. In certain preferred embodiments, the rAAV comprises an adeno-associated virus 1 capsid and a vector genome packaged in the AAV capsid, the vector genome comprising AAV inverted terminal repeats, a coding sequence for human progranulin, and regulatory sequences which direct expression of the progranulin. In certain embodiments, the vector genome comprises an AAV 5' inverted terminal repeat (ITR), a human PGRN coding sequence and regulatory elements which direct its expression, and an AAV 3' ITR. A pharmaceutical composition comprising an aqueous liquid and a recombinant AAV (rAAV) is also provided. In certain embodiments, the aqueous liquid comprises an artificial cerebrospinal fluid with a surfactant, which are suitable for intrathecal administration. Also provided are methods for treating a human patient with PGRN-FTD and/or treating a patient with brain lesions associated with PGRN-FTD. In certain embodiments, provided are methods for treating or reducing microgliosis in a patient. The method comprises delivering a rAAV.PGRN to the central nervous system (CNS). In certain embodiments, the methods provided herein may further comprise monitoring treatment by (a) non-invasively assessing the patient for reduction in retinal storage lesions as a predictor of reduction of brain lesions, (b) performing magnetic resonance imaging to assess brain volume, and/or (c) measuring concentration of PGRN concentration in the CSF. Optionally, concentration of PGRN in plasma may be measured.

As used herein, the terms "AAV.hPGRN" or "rAAV.hPGRN" are used to refer to a recombinant adeno-associated virus which has an AAV capsid having therewithin a vector genome comprising a human progranulin coding sequence under the control of regulatory sequences. Specific capsid types may be specified, such as, e.g., AAV1.hPGRN, which refers to a recombinant AAV having an AAV1 capsid; AAVhu68.hPGRN, which refers to recombinant AAV having an AAVhu68 capsid; AAV5.hPGRN refers to a recombinant AAV having an AAV5 capsid.

A "recombinant AAV" or "rAAV" is a DNAse-resistant viral particle containing two elements, an AAV capsid and a vector genome containing at least non-AAV coding sequences packaged within the AAV capsid. Unless otherwise specified, this term may be used interchangeably with the phrase "rAAV vector". The rAAV is a "replication-defective virus" or "viral vector", as it lacks any functional AAV rep gene or functional AAV cap gene and cannot generate progeny. In certain embodiments, the only AAV sequences are the AAV inverted terminal repeat sequences (ITRs), typically located at the extreme 5' and 3' ends of the vector genome in order to allow the gene and regulatory sequences located between the ITRs to be packaged within the AAV capsid.

As used herein, a "vector genome" refers to the nucleic acid sequence packaged inside the rAAV capsid which forms a viral particle. Such a nucleic acid sequence contains AAV inverted terminal repeat sequences (ITRs). In the examples herein, a vector genome contains, at a minimum, from 5' to 3', an AAV 5' ITR, coding sequence(s), and an AAV 3' ITR. ITRs from AAV2, a different source AAV than the capsid, or other than full-length ITRs may be selected. In certain embodiments, the ITRs are from the same AAV source as the AAV which provides the rep function during production or a transcomplementing AAV. Further, other ITRs may be used. Further, the vector genome contains regulatory sequences which direct expression of the gene product. Suitable components of a vector genome are discussed in more detail herein.

Therapeutic Protein and Coding Sequence:

The rAAV includes a coding sequence for human progranulin (hPGRN) protein or a variant thereof which performs one or more of the biological functions of hPGRN.

The coding sequence of this protein is engineered into the vector genome for expression in the central nervous system (CNS).

HuPGRN1 is most commonly characterized by the 593 amino acid sequence of GenBank NP_002078, which is reproduced in SEQ ID NO: 1. This sequence contains a signal peptide at positions 1 to 17, with the secreted progranulin protein or secreted granulin(s) comprising amino acids 18 to about 593. This protein may be cleaved into 8 chains; granulin 1 (aka granulin G: about aa 58 about amino acid 113), granulin 2 (about amino acids 123 to about 179), granulin 3 (about amino acid 206 to about amino acid 261), granulin 4 (about amino acid 281 to about amino acid 336), granulin 5 (about amino acid 364 to about amino acid 417), granulin 6 (about amino acid 442 to about amino acid 496), and granulin 7 (about amino acid 518 to about amino acid 573), with reference to the numbering of SEQ ID NO: 1. In certain embodiments, a heterologous signal peptide may be substituted for the native signal peptide. However, other embodiments, may encompass progranulin with an exogenous signal peptide (e.g., a human IL2 leader). See, also, e.g., www.signalpeptide.de/index.php?m=listspdb_mammalia. Thus, fusion proteins containing progranulin and/or fragments thereof are contemplated. Such fusion proteins may encompass one or more of active GRN (e.g., GRN 1, 2, 3, 4, 4, 6, or 7) in various combinations with each other, or one or more of these peptides may be combined with the full-length PGRN or another protein or peptide (e.g., another active protein or peptide and/or a signal peptide exogenous to human PGRN).

The vector genome is engineered to carry the coding sequence for this protein and to express the protein in human cells, and particularly, in the central nervous system. In certain embodiments, the coding sequence may be the native sequence, found in GenBank: NM_002087.3, which is reproduced in SEQ ID NO: 2.

In certain embodiments, the coding sequence is provided in SEQ ID NO: 3. Certain other embodiments will encompass a coding sequence which is within 95% to 99.9% or 100% identity to SEQ ID NO: 3, including values therebetween. In some embodiments, the coding sequence is codon optimized for better therapeutic outcome, e.g., enhanced expression in mammalian cells. Identity may be assessed over the coding sequence for the full-length progranulin with the signal (leader) sequence, over the progranulin without the signal (leader) sequence, or over the length of the coding sequence for a fusion protein as defined herein. In certain embodiments, the coding sequence is provided in SEQ ID NO: 3. Certain other embodiments will encompass a coding sequence which is within 95% to less than 100% identity to SEQ ID NO: 4. Identity may be assessed over the coding sequence for the full-length progranulin with the signal (leader) sequence, over the progranulin without the signal (leader) sequence, or over the length of the coding sequence for a fusion protein as defined herein.

Suitably, these coding sequences encode the full-length progranulin. However, other embodiments, may encompass the active granulin chain with a heterologous signal peptide (e.g., a human IL2 leader). See, also, e.g., www.signalpeptide.de/index.php?m=listspdb_mammalia.

In certain embodiments, fragments of the coding sequences for human PGRN (e.g., SEQ ID NO: 3 or SEQ ID NO: 4), or a sequence about 95% to 99.9% or 100% identical thereto, may be utilized. Such fragments may encode the active human GRN (aa 18-593), or a fusion peptide comprising a heterologous signal peptide with the active human GRN. In certain embodiments, one or more of the coding sequences for one or more of active GRN (e.g., GRN 1, 2, 3, 4, 4, 6, or 7) may be included in the vector genome in various combinations with each other, or one or more of these peptides may be combined with the full-length PGRN or another coding sequence.

Without wishing to be bound by theory, it is believed that AAV-mediated PGRN expression in a subset of cells in the CNS (e.g., ependymal cells) provides a depot of secreted protein. The secreted PGRN protein (and/or one or more GRN(s)) is taken up by other cells via sortilin or mannose-6-phosphate receptors where it is subsequently trafficked to the lysosome. In certain embodiments, the secreted protein is progranulin. In certain embodiments, the secreted protein is a granulin. In certain embodiments, the secreted protein includes a mixture of progranulin and granulin(s).

In certain embodiments, in addition to the progranulin coding sequence, another non-AAV coding sequence may be included, e.g., a peptide, polypeptide, protein, functional RNA molecule (e.g., miRNA, miRNA inhibitor) or other gene product, of interest. Useful gene products may include miRNAs, miRNAs and other small interfering nucleic acids regulate gene expression via target RNA transcript cleavage/degradation or translational repression of the target messenger RNA (mRNA), miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

In certain embodiments, the expression cassette further comprises one or more miRNA target sequences that repress expression of hPGRN in dorsal root ganglion (drg). In certain embodiments, the expression cassette comprises at least two tandem repeats of drg-specific miRNA target sequences, wherein the at least two tandem repeats comprise at least a first miRNA target sequence and at least a second miRNA target sequence which may be the same or different. In certain embodiments, the tandem miRNA target sequences are continuous or are separated by a spacer of 1 to 10 nucleic acids, wherein said spacer is not an miRNA target sequence. In certain embodiments, there are at least two drg-specific miRNA target sequences located at 3' to the hPGRN coding sequence. In certain embodiments, the start of the first of the at least two drg-specific miRNA tandem repeats is within 20 nucleotides from the 3' end of the hPGRN-coding sequence. In certain embodiments, the start of the first of the at least two drg-specific miRNA tandem repeats is at least 100 nucleotides from the 3' end of the hPGRN coding sequence. In certain embodiments, the miRNA tandem repeats comprise 200 to 1200 nucleotides in length. In certain embodiments, there are at least two drg-specific miRNA target sequences located at 5' to the hPGRN coding sequence. In certain embodiments, at least two drg-specific miRNA target sequences are located in both 5' and 3' to the hPGRN coding sequence. In certain embodiments, the miRNA target sequence for the at least first and/or at least second miRNA target sequence for the expression cassette mRNA or DNA positive strand is selected from (i) AGTGAATTCTACCAGTGCCATA (miR183, SEQ ID NO: 32); (ii) AGCAAAAATGTGCTAGTGCCAAA (SEQ ID NO: 33), (iii) AGTGTGAGTTCTACCATTGCCAAA (SEQ ID NO: 34); and (iv) AGGGATTCCTGG- GAAAACTGGAC (SEQ ID NO: 35). In certain embodiments, two or more consecutive miRNA target sequences are continuous and not separated by a spacer. In certain embodiments, two or more of the miRNA target sequences are separated by a spacer and each spacer is independently selected from one or more of (A) GGAT; (B) CACGTG; or (C) GCATGC. In certain embodiments, the spacer located between the miRNA target sequences may be located 3' to the first miRNA target sequence and/or 5' to the last miRNA target sequence. In certain embodiments, the spacers between the miRNA target sequences are the same. See, U.S. Provisional Patent Application No. 62/783,956, filed Dec. 21, 2018 and International Patent Application No. PCT/US19/67872, filed Feb. 12, 2020, which are hereby incorporated by reference.

AAV1

AAVhu68 which is from Clade F can be used to produce vectors which target and express hPGRN in the CNS. However, it was unexpectedly observed that AAV1-mediated PGRN delivery provided superior PGRN expression in the CNS than AAVhu68, even though comparable plasma concentrations were observed. The inventors have discovered that intrathecal delivery of rAAV1.PGRN is an attractive route of delivery for the therapies described herein. Thus, in particularly desirable embodiments, an AAV1 capsid is selected.

In certain embodiments, a composition is provided which comprises an aqueous liquid suitable for intrathecal injection and a stock of rAAV having a AAV capsid which preferentially targets ependymal cells, wherein the rAAV further comprises a vector genome having a PGRN coding sequence for delivery to the central nervous system (CNS). In certain embodiments, the composition is formulated for sub-occipital injection into the cisterna magna (intra-cisterna magna).

An AAV1 capsid refers to a capsid having AAV vp1 proteins, AAV vp2 proteins and AAV vp3 proteins. In particular embodiments, the AAV1 capsid comprises a predetermined ratio of AAV vp1 proteins, AAV vp2 proteins and AAV vp3 proteins of about 1:1:10 assembled into a T1 icosahedron capsid of 60 total vp proteins. An AAV1 capsid is capable of packaging genomic sequences to form an AAV particle (e.g., a recombinant AAV where the genome is a vector genome). Typically, the capsid nucleic acid sequences encoding the longest of the vp proteins, i.e., VP1, is expressed in trans during production of an rAAV having an AAV1 capsid are described in, e.g., U.S. Pat. Nos. 6,759,237, 7,105,345, 7,186,552, 8,637,255, and 9,567,607, which are incorporated herein by reference.

The capsid coding sequences are not present in the final assembled rAAV1.hPGRN. However, such sequences are utilized in production of a recombinant AAV. In certain embodiments, the AAV1 capsid coding sequence is any nucleic sequence which encodes the full-length AAV1 VP1 protein of SEQ ID NO: 26, or the VP2 or VP3 regions thereof. See, e.g., U.S. Pat. Nos. 6,759,237, 7,105,345, 7,186,552, 8,637,255, and 9,567,607, which are incorporated herein by reference. In certain embodiments, the AAV1 capsid coding sequence is SEQ ID NO: 25. In some embodiments, the AAV1 capsid is a protein produced from the coding sequence of SEQ ID NO: 25 with or without post-translational modification. However, variants of this coding sequence may be engineered and/or other coding sequences may be backtranslated for a desired expression system using the AAV1 VP1, AAV1 VP2, and/or AAV VP3 amino acid sequence.

In certain embodiments, compositions comprising recombinant AAV1 have capsids in which AAV1 contain five amino acids which are highly deamidated (N57, N383, N512, and N718), based on the numbering of the primary sequence of the AAV1 VP1 reproduced in SEQ ID NO: 26.

AAV1 Modification

| Enzyme | | Trypsin | Trypsin | Trypsin | Trypsin | Trypsin | Trypsin | Trypsin |
|---|---|---|---|---|---|---|---|---|
| % Coverage | N + 1 | 97.6 | 84.2 | 92.4 | 87.4 | 90.4 | 85.2 | 88.9 |
| N35 + Deamidation | Q | 9.5 | | | | | | |
| ~N57 + Deamidation | G | 100.0 | 100.0 | 100.0 | 92.0 | 89.3 | 86.1 | 85.5 |
| ~N94 + Deamidation | H | | | | 2.3 | 3.7 | 4.9 | 2.2 |
| N113 + Deamidation | L | | 5.6 | | | | | |
| ~N214 + Deamidation | N | | | | 0.9 | 0.4 | 1.0 | 0.7 |
| ~N223 + Deamidation | A | 21.4 | | 25.9 | | | | |
| N227 + Deamidation | W | 4.9 | | 3.1 | | | | |
| ~N253 + Deamidation | H | | 29.7 | | | | | |
| Q259 + Deamidation | I | 24.6 | | 14.2 | | | | |
| ~N269 + Deamidation | D | | | 21.6 | | | 5.2 | |
| ~N271 + Deamidation | H | 27.7 | | | | | | |
| N286 + Deamidation | R | 5.4 | | 5.2 | | | | |
| ~N302 + Deamidation | NNN | 43.7 | 48.6 | 18.8 | 12.4 | 28.7 | 16.3 | 11.9 |
| ~N303 + Deamidation | NNN | | 50.8 | 19.3 | | | | |
| ~N383 + Deamidation | G | 88.5 | 86.9 | 82.5 | 82.1 | 84.6 | 83.4 | 92.3 |
| ~N408 + Deamidation | N | 58.2 | 43.2 | 40.5 | 30.1 | 25.7 | 28.3 | 22.8 |
| ~N451 + Deamidation | Q | 20.5 | | | | | | |
| ~Q452 + Deamidation | S | 1.7 | | | | | | |
| N477 + Deamidation | W | 4.4 | 3.1 | 39.7 | 1.2 | 1.3 | 1.1 | 1.8 |
| ~N496 + Deamidation | NNN | 1.1 | | 69.9 | | | | |
| N512 + Deamidation | G | 93.7 | 100.0 | 100.0 | 100.0 | 100.0 | 100.0 | 97.3 |
| N651 + Deamidation | T | 2.0 | 2.1 | 1.6 | 0.6 | | | |
| N691 + Deamidation | S | | | 57.1 | | | | |
| ~N704 + Deamidation | Y | | 9.4 | | | | | |
| N718 + Deamidation | G | 98.7 | 98.1 | 98.2 | 89.5 | 91.9 | 92.3 | 87.4 |

In certain embodiments, the rAAV is administered via a computed tomography- (CT-) guided rAAV injection. In certain embodiments, the patient is administered a single dose of the composition.

In certain embodiments, AAV1 is characterized by a capsid composition of a heterogenous population of VP isoforms which are deamidated as defined in the following table, based on the total amount of VP proteins in the capsid, as determined using mass spectrometry. In certain embodiments, the AAV capsid is modified at one or more of the following positions, in the ranges provided below, as determined using mass spectrometry. Residue numbers are based on the published AAV1 sequence, reproduced in SEQ ID NO: 26.

TABLE A

| AAV1 Capsid Position Based on VP1 numbering | % |
|---|---|
| N35 + Deamidation | 1-15, 5-10 |
| ~N57 + Deamidation | 65-90, 70-95, 80-95, 75-100, 80-100, or 90-100 |
| N113 + Deamidation | 0-8 |
| ~N223 + Deamidation | 0-30, 0, 20-28 |
| N227 + Deamidation | 0, 1-5 |
| ~N253 + Deamidation | 0, 1-35 |
| Q259 + Deamidation | 0, 10-25 |
| ~N269 + Deamidation | 0-25 |
| ~N271 + Deamidation | 0-25 |
| N286 + Deamidation | 2-10 |
| ~N302 + Deamidation | 10-50 |
| ~N303 + Deamidation | 0-55 |
| ~N383 + Deamidation | 65-90, 70-95, 80-95, 75-100, 80-100, or 90-100 |
| ~N408 + Deamidation | 30-65 |
| ~N451 + Deamidation | 0-25 |
| ~Q452 + Deamidation | 0-5 |
| N477 + Deamidation | 0-45 |
| ~N496 + Deamidation | 0-75 |
| N512 + Deamidation | 75-100, 80-100, 90-100 |
| N651 + Deamidation | 0-3 |
| N691 + Deamidation | 0, 1-60 |
| ~N704 + Deamidation | 0-10 |
| N718 + Deamidation | 75-100, 80-100, 90-100 |

Suitable modifications include those described in the paragraph above labelled modulation of deamidation, which is incorporated herein. In certain embodiments, one or more of the following positions, or the glycine following the N is modified as described herein. In certain embodiments, an AAV1 mutant is constructed in which the glycine following the N at position 57, 383, 512 and/or 718 are preserved (i.e., remain unmodified). In certain embodiments, the NG at the four positions identified in the preceding sentence are preserved with the native sequence. Residue numbers are based on the published AAV1 VP1, reproduced in SEQ ID NO: 26. In certain embodiments, an artificial NG is introduced into a different position than one of the positions identified in the table above.

rAAV Vectors

As indicated above, recombinant AAV having an AAV1 capsid are the preferred vectors described herein for treatment of FTD. In certain embodiments, e.g., in the examples below (e.g., AAVhu68 or AAV5), other AAV capsids may be used to generate an rAAV. In certain embodiments, an AAV1 capsid may be selected and one or more of the elements of the vector genome comprising a hPGRN coding sequence may be substituted.

As used herein, an AAVhu68 capsid refers to a capsid as defined in WO 2018/160582, incorporated herein by reference. As described herein, a rAAVhu68 has a rAAVhu68 capsid produced in a production system expressing capsids from an AAVhu68 nucleic acid (e.g., SEQ ID NO: 30) which encodes the vp1 amino acid sequence of SEQ ID NO: 31, and optionally additional nucleic acid sequences, e.g., encoding a vp 3 protein free of the vp1 and/or vp2-unique regions. The rAAVhu68 resulting from production using a single nucleic acid sequence vp1 produces the heterogenous populations of vp1 proteins, vp2 proteins and vp3 proteins. More particularly, the AAVhu68 capsid contains subpopulations within the vp1 proteins, within the vp2 proteins and within the vp3 proteins which have modifications from the predicted amino acid residues in SEQ ID NO: 31. These subpopulations include, at a minimum, deamidated asparagine (N or Asn) residues. For example, asparagines in asparagine-glycine pairs are highly deamidated. In one embodiment, the AAVhu68 vp1 nucleic acid sequence has the sequence of SEQ ID NO: 30, or a strand complementary thereto, e.g., the corresponding mRNA or tRNA. In certain embodiments, the vp2 and/or vp3 proteins may be expressed additionally or alternatively from different nucleic acid sequences than the vp1, e.g., to alter the ratio of the vp proteins in a selected expression system. In certain embodiments, also provided is a nucleic acid sequence which encodes the AAVhu68 vp3 amino acid sequence of SEQ ID NO: 31 (about aa 203 to 736) without the vp1-unique region (about aa 1 to about aa 137) and/or vp2-unique regions (about aa 1 to about aa 202), or a strand complementary thereto, the corresponding mRNA or tRNA (about nt 607 to about nt 2211 of SEQ ID NO: 30). In certain embodiments, also provided is a nucleic acid sequence which encodes the AAVhu68 vp2 amino acid sequence of SEQ ID NO: 31 (about aa 138 to 736) without the vp1-unique region (about aa 1 to about 137), or a strand complementary thereto, the corresponding mRNA or tRNA (nt 411 to 2211 of SEQ ID NO: 30).

As used herein, an AAV5 capsid has a predicted amino acid sequence of SEQ ID NO: 29. In certain embodiments, the AAV5 capsid is expressed from a nucleic acid sequence of SEQ ID NO: 28.

Genomic sequences which are packaged into an AAV capsid and delivered to a host cell are typically composed of, at a minimum, a transgene and its regulatory sequences, and AAV inverted terminal repeats (ITRs). Both single-stranded AAV and self-complementary (sc) AAV are encompassed with the rAAV. The transgene is a nucleic acid coding sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J. Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. In one embodiment, the ITRs are from an AAV different than that supplying a capsid. In one embodiment, the ITR sequences from AAV2. A shortened version of the 5' ITR, termed ΔITR, has been described in which the D-sequence and terminal resolution site (trs) are deleted. In other embodiments, the full-length AAV 5' and 3' ITRs are used. However, ITRs from other AAV sources may be selected. Where the source of the ITRs is from AAV2 and the AAV capsid is from another AAV source, the resulting vector may be termed pseudotyped. However, other configurations of these elements may be suitable.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

The regulatory control elements typically contain a promoter sequence as part of the expression control sequences, e.g., located between the selected 5' ITR sequence and the coding sequence. Constitutive promoters, regulatable promoters [see, e.g., WO 2011/126808 and WO 2013/04943], tissue specific promoters, or a promoter responsive to physiologic cues may be used may be utilized in the vectors described herein. The promoter(s) can be selected from different sources, e.g., human cytomegalovirus (CMV) immediate-early enhancer/promoter, the SV40 early enhancer/promoter, the JC polymovirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter. In addition to a promoter a vector may contain one or more other appropriate transcription initiation, termination, enhancer sequences, efficient RNA processing signals such as splicing and polyadenylation (polyA) signals; sequences that stabilize cytoplasmic mRNA for example WPRE; sequences that enhance translation efficiency (i.e., Kozak consensus sequence); sequences that enhance protein stability; and when desired, sequences that enhance secretion of the encoded product. An example of a suitable enhancer is the CMV enhancer. Other suitable enhancers include those that are appropriate for desired target tissue indications. In one embodiment, the expression cassette comprises one or more expression enhancers. In one embodiment, the expression cassette contains two or more expression enhancers. These enhancers may be the same or may differ from one another. For example, an enhancer may include a CMV immediate early enhancer. This enhancer may be present in two copies which are located adjacent to one another. Alternatively, the dual copies of the enhancer may be separated by one or more sequences. In still another embodiment, the expression cassette further contains an intron, e.g, the chicken beta-actin intron. Other suitable introns include those known in the art, e.g., such as are described in WO 2011/126808. Examples of suitable polyA sequences include, e.g., SV40, SV50, bovine growth hormone (bGH), human growth hormone, and synthetic polyAs. Optionally, one or more sequences may be selected to stabilize mRNA. An example of such a sequence is a modified WPRE sequence, which may be engineered upstream of the polyA sequence and downstream of the coding sequence [see, e.g., M A Zanta-Boussif, et al, Gene Therapy (2009) 16: 605-619.

In one embodiment, the vector genome comprises: an AAV 5' ITR, a promoter, an optional enhancer, an optional intron, a coding sequence for human PGRN(s) or a fusion protein comprising same, a poly A, and an AAV 3' ITR. In certain embodiments, the vector genome comprises: a AAV 5' ITR, a promoter, an optional enhancer, an optional intron, a coding sequence for human PGRN or a fusion protein comprising same, a poly A, and an AAV 3' ITR. In certain embodiments, the vector genome comprises: a AAV 5' ITR, a promoter, an optional enhancer, an optional intron, a huPGRN coding sequence, a poly A, and an AAV 3' ITR. In certain embodiments, the vector genome comprises: an AAV2 5' ITR, an EF1a promoter, an optional enhancer, an optional promoter, huPGRN, an SV40 poly A, and an AAV2 3' ITR. In certain embodiments, the vector genome is AAV2 5' ITR, UbC promoter, optional enhancer, optional intron, huPGRN, an SV40 poly A, and an AAV2 3' ITR. In certain embodiments, the vector genome is AAV2 5' ITR, CB7 promoter, an intron, huPGRN, an SV40 poly A, and an AAV2 3' ITR. In certain embodiment, the vector genome is an AAV2 5' ITR, CB7 promoter, intron, huPGRN, a rabbit beta globin poly A, and an AAV2 3' ITR. See, e.g., SEQ ID NO: 22 (EF1a.huPGRN.SV40), SEQ ID NO: 23 (UbC.PI.huPGRN.SV40), or SEQ ID NO: 24 (CB7.CI.hPGRN1.rGB). The huPGRN coding sequences are selected from those defined in the present specification. See, e.g., SEQ ID NO: 3 or a sequence 95% to 99.9% identical thereto, or SEQ ID NO: 4 or a sequence 95% to 99.9% identical thereto, or a fragment thereof as defined herein. Illustrative sequences of vector elements used in the examples below are provided, e.g., in SEQ ID NO: 6 (rabbit globin polyA), AAV ITRs (SEQ ID NO: 7 and 8), human CMV IE promoter (SEQ ID NO: 9), CB promoter (SEQ ID NO: 10), a chimeric intron (SEQ ID NO: 11), UbC promoter (SEQ ID NO: 12), an EF-1a promoter (SEQ ID NO: 17), an intron (SEQ ID NO: 13), and an SV40 late poly A (SEQ ID NO: 14). Other elements of the vector genome or variations on these sequences may be selected for the vector genomes for certain embodiments of this invention.

Vector Production

For use in producing an AAV viral vector (e.g., a recombinant (r) AAV), the expression cassettes can be carried on any suitable vector, e.g., a plasmid, which is delivered to a packaging host cell. The plasmids useful in this invention may be engineered such that they are suitable for replication and packaging in vitro in prokaryotic cells, insect cells, mammalian cells, among others. Suitable transfection techniques and packaging host cells are known and/or can be readily designed by one of skill in the art.

Methods for generating and isolating AAVs suitable for use as vectors are known in the art. See generally, e.g., Grieger & Samulski, 2005, "Adeno-associated virus as a gene therapy vector: Vector development, production and clinical applications," *Adv. Biochem. Engin/Biotechnol.* 99: 119-145; Buning et al., 2008, "Recent developments in adeno-associated virus vector technology," *J. Gene Med.* 10:717-733; and the references cited below, each of which is incorporated herein by reference in its entirety. For packaging a transgene into virions, the ITRs are the only AAV components required in cis in the same construct as the nucleic acid molecule containing the expression cassettes. The cap and rep genes can be supplied in trans.

In one embodiment, the expression cassettes described herein are engineered into a genetic element (e.g., a shuttle plasmid) which transfers the immunoglobulin construct sequences carried thereon into a packaging host cell for production a viral vector. In one embodiment, the selected genetic element may be delivered to an AAV packaging cell by any suitable method, including transfection, electroporation, liposome delivery, membrane fusion techniques, high velocity DNA-coated pellets, viral infection and protoplast fusion. Stable AAV packaging cells can also be made. Alternatively, the expression cassettes may be used to generate a viral vector other than AAV, or for production of mixtures of antibodies in vitro. The methods used to make such constructs are known to those with skill in nucleic acid manipulation and include genetic engineering, recombinant engineering, and synthetic techniques. See, e.g., Molecular Cloning: A Laboratory Manual, ed. Green and Sambrook, Cold Spring Harbor Press, Cold Spring Harbor, NY (2012).

The term "AAV intermediate" or "AAV vector intermediate" refers to an assembled rAAV capsid which lacks the desired genomic sequences packaged therein. These may also be termed an "empty" capsid. Such a capsid may contain no detectable genomic sequences of an expression cassette, or only partially packaged genomic sequences which are insufficient to achieve expression of the gene product. These empty capsids are non-functional to transfer the gene of interest to a host cell.

The recombinant adeno-associated virus (AAV) described herein may be generated using techniques which are known. See, e.g., WO 2003/042397; WO 2005/033321, WO 2006/110689; U.S. Pat. No. 7,588,772 B2. Such a method involves culturing a host cell which contains a nucleic acid sequence encoding an AAV capsid protein; a functional rep gene; an expression cassette composed of, at a minimum, AAV inverted terminal repeats (ITRs) and a transgene; and sufficient helper functions to permit packaging of the expression cassette into the AAV capsid protein. Methods of generating the capsid, coding sequences therefor, and methods for production of rAAV viral vectors have been described. See, e.g., Gao, et al, Proc. Natl. Acad. Sci. U.S.A. 100 (10), 6081-6086 (2003) and US 2013/0045186A1.

In one embodiment, a production cell culture useful for producing a recombinant AAV is provided. Such a cell culture contains a nucleic acid which expresses the AAV capsid protein in the host cell; a nucleic acid molecule suitable for packaging into the AAV capsid, e.g., a vector genome which contains AAV ITRs and a non-AAV nucleic acid sequence encoding a gene product operably linked to sequences which direct expression of the product in a host cell; and sufficient AAV rep functions and adenovirus helper functions to permit packaging of the nucleic acid molecule into the recombinant AAV capsid. In one embodiment, the cell culture is composed of mammalian cells (e.g., human embryonic kidney 293 cells, among others) or insect cells (e.g., baculovirus).

Typically, the rep functions are from the same AAV source as the AAV providing the ITRs flanking the vector genome. In the examples herein, the AAV2 ITRs are selected and the AAV2 rep is used. The coding sequence is reproduced in SEQ ID NO: 27. Optionally, other rep sequences or another rep source (and optionally another ITR source) may be selected. For example, the rep may be, but is not limited to, AAV1 rep protein, AAV2 rep protein; or rep 78, rep 68, rep 52, rep 40, rep68/78 and rep40/52; or a fragment thereof; or another source. Optionally, the rep and cap sequences are on the same genetic element in the cell culture. There may be a spacer between the rep sequence and cap gene. Any of these AAV or mutant AAV capsid sequences may be under the control of exogenous regulatory control sequences which direct expression thereof in a host cell.

In one embodiment, cells are manufactured in a suitable cell culture (e.g., HEK 293) cells. Methods for manufacturing the gene therapy vectors described herein include methods well known in the art such as generation of plasmid DNA used for production of the gene therapy vectors, generation of the vectors, and purification of the vectors. In some embodiments, the gene therapy vector is an AAV vector and the plasmids generated are an AAV cis-plasmid encoding the AAV genome and the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media.

In certain embodiments, the manufacturing process for rAAV.hPGRN involves transient transfection of HEK293 cells with plasmid DNA. A single batch or multiple batches are produced by PEI-mediated triple transfection of HEK293 cells in PALL iCELLis bioreactors. Harvested AAV material are purified sequentially by clarification, TFF, affinity chromatography, and anion exchange chromatography in disposable, closed bioprocessing systems where possible.

The harvested vector-containing cells and culture media are referred to herein as crude cell harvest. In yet another system, the gene therapy vectors are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065, which are incorporated herein by reference.

The crude cell harvest may thereafter be subject to additional method steps such as concentration of the vector harvest, diafiltration of the vector harvest, microfluidization of the vector harvest, nuclease digestion of the vector harvest, filtration of microfluidized intermediate, crude purification by chromatography, crude purification by ultracentrifugation, buffer exchange by tangential flow filtration, and/or formulation and filtration to prepare bulk vector.

A two-step affinity chromatography purification at high salt concentration followed anion exchange resin chromatography are used to purify the vector drug product and to remove empty capsids. These methods are described in more detail in International Patent Application No. PCT/US2016/065970, filed Dec. 9, 2016, which is incorporated by reference herein. Purification methods for AAV8, International Patent Application No. PCT/US2016/065976, filed Dec. 9, 2016, and rh10, International Patent Application No. PCT/US16/66013, filed Dec. 9, 2016, entitled "Scalable Purification Method for AAVrh10", also filed Dec. 11, 2015, and for AAV1, International Patent Application No. PCT/US2016/065974, filed Dec. 9, 2016, for "Scalable Purification Method for AAV1", filed Dec. 11, 2015, are all incorporated by reference herein.

To calculate empty and full particle content, VP3 band volumes for a selected sample (e.g., in examples herein an iodixanol gradient-purified preparation where # of GC=# of particles) are plotted against GC particles loaded. The resulting linear equation ($y=mx+c$) is used to calculate the number of particles in the band volumes of the test article peaks. The number of particles (pt) per 20 μL loaded is then multiplied by 50 to give particles (pt)/mL. Pt/mL divided by GC/mL gives the ratio of particles to genome copies (pt/GC). Pt/mL-GC/mL gives empty pt/mL. Empty pt/mL divided by pt/mL and x 100 gives the percentage of empty particles.

Generally, methods for assaying for empty capsids and AAV vector particles with packaged genomes have been known in the art. See, e.g., Grimm et al., Gene Therapy (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., J. Virol. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress™ (Invitrogen, CA) according to the manufacturer's instructions or other suitable staining method, i.e. SYPRO™ ruby or coomassie stains. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan® fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is used which utilizes a broad-spectrum serine protease, e.g., proteinase K (such as is commercially available from Qiagen®). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2-fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000-fold) and subjected to TaqMan® analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

In brief, the method for separating rAAV particles having packaged genomic sequences from genome-deficient AAV intermediates involves subjecting a suspension comprising recombinant AAV viral particles and AAV capsid intermediates to fast performance liquid chromatography, wherein the AAV viral particles and AAV intermediates are bound to a strong anion exchange resin equilibrated at a high pH, and subjected to a salt gradient while monitoring eluate for ultraviolet absorbance at about 260 and about 280. The pH may be adjusted depending upon the AAV selected. See, e.g., WO2017/160360 (AAV9), WO2017/100704 (AAVrh10), WO 2017/100676 (e.g., AAV8), and WO 2017/100674 (AAV1), which are incorporated by reference herein. In this method, the AAV full capsids are collected from a fraction which is eluted when the ratio of A260/A280 reaches an inflection point. In one example, for the Affinity Chromatography step, the diafiltered product may be applied to a Capture Select™ Poros-AAV2/9 affinity resin (Life Technologies) that efficiently captures the AAV2 serotype. Under these ionic conditions, a significant percentage of residual cellular DNA and proteins flow through the column, while AAV particles are efficiently captured.

Compositions

Provided herein are compositions containing at least one rAAV.hPGRN stock an rAAV stock) and an optional carrier, excipient and/or preservative. An rAAV stock refers to a plurality of rAAV vectors which are the same, e.g., such as in the amounts described below in the discussion of concentrations and dosage units.

In certain embodiments, a composition comprises a virus stock which is a recombinant AAV (rAAV) suitable for use in treating progranulin-related frontal temporal dementia (FTD), said rAAV comprising: (a) an adeno-associated virus 1 capsid, and (b) a vector genome packaged in the AAV capsid, said vector genome comprising AAV inverted terminal repeats, a coding sequence for human progranulin, and regulatory sequences which direct expression of the progranulin. In certain embodiments, the vector genome comprises a promoter, an enhancer, an intron, a human PGRN coding sequence, and a polyadenylation signal. In certain embodiments, the intron consists of a chicken beta actin splice donor and a rabbit β splice acceptor element. In certain embodiments, the vector genome further comprises an AAV2 5' ITR and an AAV2 3' ITR which flank all elements of the vector genome.

The rAAV.hPGRN, preferably suspended in a physiologically compatible carrier, may be administered to a human or non-human mammalian patient. In certain embodiments, for administration to a human patient, the rAAV is suitably suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.5 to 7.5, pH 7.0 to 7.7, or pH 7.2 to 7.8. As the pH of the cerebrospinal fluid is about 7.28 to about 7.32, or a pH of 7.2 to 7.4, for intrathecal delivery, a pH within this range may be desired; whereas for intravenous delivery, a pH of about 6.8 to about 7.2 may be desired. However, other pHs within the broadest ranges and these subranges may be selected for other route of delivery.

In certain embodiments, the formulation may contain a buffered saline aqueous solution not comprising sodium bicarbonate. Such a formulation may contain a buffered saline aqueous solution comprising one or more of sodium phosphate, sodium chloride, potassium chloride, calcium chloride, magnesium chloride and mixtures thereof, in water, such as a Harvard's buffer. The aqueous solution may further contain Kolliphor® P188, a poloxamer which is commercially available from BASF which was formerly sold under the trade name Lutrol® F68. The aqueous solution may have a pH of 7.2 or a pH of 7.4.

In another embodiment, the formulation may contain a buffered saline aqueous solution comprising 1 mM Sodium Phosphate (Na3PO4), 150 mM sodium chloride (NaCl), 3 mM potassium chloride (KCl), 1.4 mM calcium chloride (CaCl2), 0.8 mM magnesium chloride (MgCl2), and 0.001% Kolliphor® 188. See, e.g., harvardapparatus.com/harvard-apparatus-perfusion-fluid.html. In certain embodiments, Harvard's buffer is preferred.

In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

In another embodiment, the composition includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV, from sticking to the infusion tubing but does not interfere with the rAAV binding activity in vivo.

Optionally, the compositions may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host. Delivery vehicles such as liposomes, nanocapsules, microparticles, microspheres, lipid particles, vesicles, and the like, may be used for the introduction of the compositions of the present invention into suitable host cells. In particular, the rAAV vector delivered transgenes may be formulated for delivery either encapsulated in a lipid particle, a liposome, a vesicle, a nanosphere, or a nanoparticle or the like.

In one embodiment, a composition includes a final formulation suitable for delivery to a subject, e.g., is an aqueous liquid suspension buffered to a physiologically compatible pH and salt concentration. Optionally, one or more surfactants are present in the formulation. In another embodiment, the composition may be transported as a concentrate which is diluted for administration to a subject. In other embodiments, the composition may be lyophilized and reconstituted at the time of administration.

A suitable surfactant, or combination of surfactants, may be selected from among non-ionic surfactants that are non-toxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL® (Polyoxy capryllic glyceride), polyoxy 10 oleyl ether, TWEEN® (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

The vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Optionally, routes other than intrathecal administration may be used, such as, e.g., direct delivery to a desired organ (e.g., the liver (optionally via the hepatic artery), lung, heart, eye, kidney), oral, inhalation, intranasal, intratracheal, intraarterial, intraocular, intravenous, intramuscular, subcutaneous, intradermal, and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 25 to about 1000 microliters to about 100 mL of solution containing concentrations of from about $1 \times 10^9$ to $1 \times 10^{16}$ genomes virus vector (to treat an average subject of 70 kg in body weight) including all integers or fractional amounts within the range, and preferably $1.0 \times 10^{12}$ GC to $1.0 \times 10^{14}$ GC for a human patient. In one embodiment, the compositions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, or $9 \times 10^{11}$ GC per dose including all integers or fractional amounts within the range. In another embodiment, the compositions are formulated to contain at least $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per dose including all integers or fractional amounts within the range. In another embodiment, the compositions are formulated to contain at least $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $1 \times 10^{10}$ to about $1 \times 10^{12}$ GC per dose including all integers or fractional amounts within the range.

In certain embodiments, the dose is in the range of about $1 \times 10^9$ GC/g brain mass to about $1 \times 10^{12}$ GC/g brain mass. In certain embodiments, the dose is in the range of about $1 \times 10^{10}$ GC/g brain mass to about $3.33 \times 10^{11}$ GC/g brain mass. In certain embodiments, the dose is in the range of about $3.33 \times 10^{11}$ GC/g brain mass to about $1.1 \times 10^{12}$ GC/g brain mass. In certain embodiments, the dose is in the range of about $1.1 \times 10^{12}$ GC/g brain mass to about $3.33 \times 10^{13}$ GC/g brain mass. In certain embodiments, the dose is lower than $3.33 \times 10^{11}$ GC/g brain mass. In certain embodiments, the dose is lower than $1.1 \times 10^{12}$ GC/g brain mass. In certain embodiments, the dose is lower than $3.33 \times 10^{13}$ GC/g brain mass.

In certain embodiments, the dose is about $1 \times 10^{10}$ GC/g brain mass. In certain embodiments, the dose is about $2 \times 10^{10}$ GC/g brain mass. In certain embodiments, the dose is about $2 \times 10^{10}$ GC/g brain mass. In certain embodiments, the dose is about $3 \times 10^{10}$ GC/g brain mass. In certain embodiments, the dose is about $4 \times 10^{10}$ GC/g brain mass. In certain embodiments, the dose is about $5 \times 10^{10}$ GC/g brain mass. In certain embodiments, the dose about $6 \times 10^{10}$ GC/g brain mass. In certain embodiments, the dose is about $7 \times 10^{10}$ GC/g brain mass. In certain embodiments, the dose about $8 \times 10^{10}$ GC/g brain mass. In certain embodiments, the dose is about $9 \times 10^{10}$ GC/g brain mass. In certain embodiments, the dose is about $1 \times 10^{11}$ GC/g brain mass. In certain embodiments, the dose is about $2 \times 10^{11}$ GC/g brain mass. In certain embodiments, the dose is about $3 \times 10^{11}$ GC/g brain mass. In certain embodiments, the dose is about $4 \times 10^{11}$ GC/g brain mass.

In certain embodiments, the dose is administered to humans as a flat dose in the range of about $1.44 \times 10^{13}$ to $4.33 \times 10^{14}$ GC of the rAAV. In certain embodiments, the dose is administered to humans as a flat dose in the range of about $1.44 \times 10^{13}$ to $2 \times 10^{14}$ GC of the rAAV. In certain embodiments, the dose is administered to humans as a flat dose in the range of about $3 \times 10^{13}$ to $1 \times 10^{14}$ GC of the rAAV.

In certain embodiments, the dose is administered to humans as a flat dose in the range of about $5 \times 10^{13}$ to $1 \times 10^{14}$ GC of the rAAV.

In some embodiments, the compositions can be formulated in dosage units to contain an amount of AAV that is in the range of about $1 \times 10^{13}$ to $8 \times 10^{14}$ GC of the rAAV. In some embodiments, the compositions can be formulated in dosage units to contain an amount of rAAV that is in the range of about $1.44 \times 10^{13}$ to $4.33 \times 10^{14}$ GC of the rAAV. In some embodiments, the compositions can be formulated in dosage units to contain an amount of rAAV that is in the range of about $3 \times 10^{13}$ to $1 \times 10^{14}$ GC of the rAAV. In some embodiments, the compositions can be formulated in dosage units to contain an amount of rAAV that is in the range of about $5 \times 10^{13}$ to $1 \times 10^{14}$ GC of the rAAV.

In certain embodiments, the rAAV is administered to a subject in a single dose. In certain embodiments, multiple doses (for example 2 doses) is desired.

The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene. Optionally, dosage regimens similar to those described for therapeutic purposes may be utilized for immunization using the compositions of the invention.

As used herein, the terms "intrathecal delivery" or "intrathecal administration" refer to a route of administration for drugs via an injection into the spinal canal, more specifically into the subarachnoid space so that it reaches the cerebrospinal fluid (CSF). Intrathecal delivery may include lumbar puncture, intraventricular (including intracerebroventricular (ICV)), suboccipital/intracisternal, and/or C1-2 puncture. For example, material may be introduced for diffusion throughout the subarachnoid space by means of lumbar puncture. In another example, injection may be into the cisterna magna or via intraparenchymal delivery. In certain embodiments, the rAAV is administered via a computed tomography- (CT-) guided sub-occipital injection into the cisterna magna (intra-cisterna magna). In certain embodiments, the patient is administered a single dose.

As used herein, the terms "intracisternal delivery" or "intracisternal administration" refer to a route of administration for drugs directly into the cerebrospinal fluid of the cisterna magna cerebellomedularis, more specifically via a suboccipital puncture or by direct injection into the cisterna magna or via permanently positioned tube.

In certain embodiments, the stock of rAAV.hPGRN is formulated in intrathecal final formulation buffer (ITFFB; artificial CSF with 0.001% Pluronic® F-68). The batch or batches are frozen, subsequently thawed, pooled if necessary, adjusted to the target concentration, sterile-filtered through a 0.22 um filter, and vials are filled. In certain embodiments, the suspension comprising the formulation buffer the rAAV1.hPGRN is adjusted to a pH of 7.2 to 7.4.

In one embodiment, volumes for delivery of the doses of rAAV1.hPGRN provided herein and concentrations may be determined by one of skill in the art. For example, volumes of about 1 µL to 150 mL may be selected, with the higher volumes being selected for adults. Typically, for newborn infants a suitable volume is about 0.5 mL to about 10 mL, for older infants, about 0.5 mL to about 15 mL may be selected. For toddlers, a volume of about 0.5 mL to about 20 mL may be selected. For children, volumes of up to about 30 mL may be selected. For pre-teens and teens, volumes up to about 50 mL may be selected. In still other embodiments, a patient may receive an intrathecal administration in a volume of about 5 mL to about 15 mL are selected, or about 7.5 mL to about 10 mL. Other suitable volumes and dosages may be determined. The dosage will be adjusted to balance the therapeutic benefit against any side effects and such dosages may vary depending upon the therapeutic application for which the recombinant vector is employed.

In certain embodiments, a composition comprises: rAAV.EF1a.huPGRN.SV40, rAAV.UbC.PI.huPGRN.SV40, or rAAVCB7.CI.hPGRN1.rGB. Compositions in which the rAAV capsid is AAVhu68, AAV5 or AAV1 are illustrated in the examples below. In particularly preferred embodiments, the rAAV is AAV1. In certain embodiments, the huPGRN coding sequences are selected from those defined in the present specification. See, e.g., SEQ ID NO: 3 or a sequence 95% to 99.9% identical thereto, or SEQ ID NO: 4 or a sequence 95% to 99.9% identical thereto, or a fragment thereof as defined herein. Illustrative sequences of vector elements used in the examples below are provided, e.g., in SEQ ID NO: 6 (rabbit globin polyA), AAV ITRs (SEQ ID NO: 7 and 8), human CMV IE promoter (SEQ ID NO: 9), CB promoter (SEQ ID NO: 10), a chimeric intron (SEQ ID NO: 11), UbC promoter (SEQ ID NO: 12), an EF-1a promoter (SEQ ID NO: 17), an intron (SEQ ID NO: 13), and an SV40 late poly A (SEQ ID NO: 14).

Uses

As used herein, a PGRN haploinsufficiency refers to patients with a mutation in the PGRN gene, which results in deficient PGRN and/or deficient GRN(s) levels. The target population for an rAAV1-PGRN therapy includes patients which have a PGRN haploinsufficiency and/or patients who otherwise have deficient PGRN or deficient GRN levels. In certain embodiments, the patient is heterozygous for a PGRN mutation. In yet another embodiment, the patient is homozygous from a PGRN mutation. In certain embodiments, the patient is administered an immune suppression regimen in combination with rAAV1-mediated hPGRN therapy provided herein.

In certain embodiments, the rAAV1.PGRN is useful in treating patients having a GRN haploinsufficiency. Such patients may have been diagnosed with adult-onset neurodegeneration caused by GRN haploinsufficiency or may be pre-symptomatic. The rAAV1.PGRN can be administered as a single dose via a computed tomography- (CT-) guided sub-occipital injection into the cisterna magna (intra-cisterna magna RCMP. A single dose is administered at a pre-determined dose level. The superior brain transduction achieved with a single ICM injection in NHPs resulted in the selection of this route of administration. In certain embodiments, administration of the vector into the ICM also results in reduced anti-PGRN T cell responses as compared to another route of administration (e.g. injection into the lateral ventricle). Once a common procedure, ICM injection (also known as suboccipital puncture) had previously been supplanted by lumbar-puncture. However, other dosing levels and routes of delivery may be selected and/or used in conjunction with this rAAV1-mediated hPGRN therapy.

In certain embodiments, the rAAV1-mediated therapy described herein may provide PGRN expression at about average, normal, physiological levels for a human without a GRN mutation (haploinsufficiency). However, the treatment may provide therapeutic effect even if the increase in PGRN expression is below normal levels, providing about 40% to 99% of normal average levels, e.g., 35%, 40%, 45%, 50%, 55%, 60%, 65%, 70%, 75%, 80%, 85%, 90%, 95%, or other values therebetween these ranges. In certain embodiments, this may result from an increased PGRN level of at least 5% to about 70%, or more, above the patient's expression levels prior to treatment. In certain embodiments, the treatment provides therapeutic efficacy where administration of rAAV1-mediated hPGRN results in elevated levels of PGRN in the CSF (e.g., 10-fold to 40-fold higher than normal levels).

In certain embodiments, efficacy is assessed by one or more of: increased levels of PGRN protein in CSF and/or changes in brain cortical thickness. In certain embodiment, efficacy of rAAV1-mediated therapy is assessed following administration of a single ICM dose as measured by one or more of: prolonged survival, and improvement on of clinical symptoms and daily functioning as assessed by the Mini-Mental State Exam (MMSE), Clinical Global Impression of Change (CGI-C), Frontal Assessment Battery (FAB), Frontotemporal Dementia Rating Scale (FRS), Frontal Behavioral Inventory (FBI), Unified Parkinson's Disease Rating Scale (UPDRS), verbal fluency testing, Clinical Dementia Rating for Frontotemporal Lobar Degeneration Sum of Boxes (CDR-FTLD sb), and/or Neuropsychiatric Inventory (NPI). In certain embodiments, efficacy is demonstrated by improvement in CSF levels of neurofilament light chain (NFL), tau, phosphorylated tau, and inflammatory markers and/or increased Plasma levels of PGRN. In certain embodiments, efficacy is assessed by measuring a reduction or reversal in levels of microgliosis.

In certain embodiments, efficacy is measured by improvement in one or more of the clinical symptoms associated with GRN patients, including, e.g., behavioral deficits (disinhibition, apathy, loss of sympathy or empathy, compulsive or stereotyped behaviors, or hyperorality) and cognitive deficits (decline in executive function without a significant impact on episodic memory or visual-spatial skills).

In certain embodiments, improvement is observed in some other, more atypical symptoms, including psychiatric features (delusions, hallucinations, and obsessive behaviors) and/or other cognitive deficits (episodic memory impairment, apraxia, and visuospatial dysfunction). Assessment may be performed using FTDC criteria may be evaluated, including brain imaging for signs of frontal and/or temporal degeneration, an assessment of decline on a clinical rating scale (such as the Clinical Dementia Rating for Frontotemporal Lobar Degeneration [CDR-FTLD], Frontal Behavior Inventory [FBI], Neuropsychiatric Inventory [NPI], and Frontotemporal Dementia Rating Scale [FRS]), and, ultimately, genetic testing to confirm a pathogenic GRN mutation. Cerebrospinal fluid (CSF) biomarkers, including tau and amyloid-β, as well amyloid positron emission tomography (PET) imaging, may be used.

In certain embodiments, improvement is observed in GRN mutation carriers having primary progressive aphasia (PPA), which is characterized by symptoms related to speech and language. They may be diagnosed using guidelines based upon the Mesulam criteria, which distinguishes three clinical variants of PPA: semantic variant PPA (svPPA), nonfluent variant PPA (nfvPPA), and logopenic variant PPA (1vPPA) (Gorno-Tempini et al., (2011). "Classification of primary progressive aphasia and its variants." Neurology. 76(11):1006-14). nfvPPA presents with deficits in the ability to produce speech, and the core features include agrammatism in language production, effortful speech, and apraxia of speech. svPPA presents with deficits in the ability to understand the meanings of words, and the core features include impaired naming of words and single-word comprehension. 1vPPA is characterized by difficulty finding the appropriate words while speaking, and is not accompanied by a decline in word comprehension. The core features of lvPPA are deficits in word retrieval and the capacity to repeat sentences. GRN mutation carriers most commonly present with nfvPPA; however, they can have broader symptoms spanning the PPA clinical spectrum, resulting in a diagnosis of "PPA—not otherwise specified" (Gorno-Tempini et al., 2011; Woollacott and Rohrer, 2016).

A method of treating a human patient with a neurodegenerative condition associated with GRN haploinsufficiency is provided. In certain embodiments, this condition is progranulin-related frontotemporal dementia (FTD). The method comprises delivering a coding sequence for a progranulin to the central nervous system (CNS) via a recombinant adeno-associated virus (rAAV) having an adeno-associated virus 1 (AAV1) capsid, said rAAV further comprising a vector genome packaged in the AAV capsid, said vector genome comprising AAV inverted terminal repeats, a coding sequence for human progranulin, and regulatory sequences which direct expression of the progranulin.

A method for treating a human patient with brain lesions associated with progranulin-related frontal temporal dementia or another neurodegenerative condition associated with GRN haploinsufficiency is provided. The method comprises administering a coding sequence for a progranulin to the central nervous system (CNS) via a recombinant adeno-associated virus (rAAV) having an adeno-associated virus 1 (AAV1) capsid, said rAAV further comprising a vector genome packaged in the AAV capsid, said vector genome comprising AAV inverted terminal repeats, a coding sequence for human progranulin, and regulatory sequences which direct expression of the progranulin.

In certain embodiments, the methods provided herein may further comprise monitoring treatment by (a) non-invasively assessing the patient for reduction in retinal storage lesions as a predictor of reduction of brain lesions, (b) performing magnetic resonance imaging to assess brain volume, and/or (c) measuring concentration of progranulin in the CSF. Optionally, progranulin concentration in plasma may be assessed.

In certain embodiments, efficacy of an rAAV.hPGRN composition is assessed by one or more of the following primarily cognitive, primarily behavioral, or cognitive/other methods. The following describes suitable assessments.

Primarily Cognitive assessments include verbal fluency testing, clinical dementia ratio for FTLD, or mini-mental state exam (MMSE). Verbal fluency testing will likely be conducted by presenting the same picture/photograph to each subject and asking for a verbal description. During the description, rate of speech (words/minute) will be counted, recorded and ultimately compared to rates reflective of neuro-typical adults. The CDR-FTLD is an extended version of the classic CDR, which is historically used to rate the severity of Alzheimer's disease spectrum disorders. The assessment includes the original 6 domains of the CDR (memory, orientation, judgment and problem solving, community affairs, home and hobbies, personal care) as well as two additional domains: language and behavior, which allows for more sensitivity in detection of decline in FTLD. A rating of "0" indicates normal behavior or language, while scores of "1", "2" or "3" indicate mild to severe deficits. The 'sum of boxes', or the sum of the individual domain scores, is used to determine global dementia severity. The MMSE is an 11-question global cognitive assessment widely used in clinical and research practice. Questions such as "What is the year? Season? Date? Day of the week? Month?" are asked and one point is given for each correct answer, with maximum scores provided for each question. The maximum, total score is 30, with two cut-offs at scores of 24 and 27. These cutoffs are indicators of cognitive decline.

Primarily Motor assessments include, e.g., Unified Parkinson's Disease Rating Scale (UPDRS). The UPDRS is a 42-item, 4-part assessment of several domains related to Parkinsonism, such as Mentation, Behavior and Mood and Activities of Daily Living. Each item includes a rating scale typically ranging from 0 (typically indicating no impairment) to 4 (typically indicating the most severe impairment). The scores for each part are tallied to provide an indication of severity of the disease with a high score of 199 indicating the worst/most total disability.

Primarily Behavioral assessments include, e.g., neuropsychiatric inventory (NPI) or Frontal Behavioral Inventory (FBI). The NPI is used to elucidate the presence of psychopathology in patients with disorders of the brain. Initially, it was developed for use in Alzheimer's disease populations; however, it may be useful to assess behavioral changes in other conditions. The assessment consists of 10 behavioral domains and 2 neurovegetative areas, within which there are 4 scores: frequency, severity, total and caregiver distress. The NPI total score is obtained by adding the domain scores of the behavioral domains, less the caregiver distress scores. The FBI is a 24-item assessment targeted to assess changes in behavior and personality associated specifically with bvFTD and to differentiate between FTD and other dementias. It is administered as a face-to-face interview with the primary caregiver, as patients with a bvFTD diagnosis generally do not have sufficient insight into these types of changes. It focuses on several behavioral and personality-related areas, scoring each question from 0 (none) to 3 (severe/most of the time). The total score provides insight into the severity of illness and can be used to assess change over time.

Other/Both Cognitive and Motor assessments include, e.g., Columbia Suicide Severity Rating Scale (C-SSRS), Clinical Global Impression of Change (CGI-C), Frontal Assessment Battery (FAB), and/or Frontotemporal Dementia Rating Scale (FDR). The C-SSRS is a 3-part scale measuring Suicidal Ideation, Intensity of Ideation and Suicidal Behavior through questions evaluating suicidal ideation and behavior. The outcome of this assessment is composed of a suicidal behavior lethality rating taken directly from the scale, a suicidal ideation score and a suicidal ideation intensity ranking. An ideation score greater than 0 may indicate the need for intervention, based on the assessment guidelines. The intensity rating has a range of 0 to 25, with 0 representing no endorsement of suicidal ideation. The CGI-C is one of three parts of a brief, widely used assessment composed of 3 items that are clinician-observer rated. The CGI-C is rated on a 7 point scale, ranging from 1 (very much improved) to 7 (very much worse) starting from enrollment in the study, whether or not any improvement is due entirely to treatment. The FAB is a brief assessment to assist in differentiating between dementias with a frontal dysexecutive phenotype and of Alzheimer's type. It is particularly useful in mildly demented patients (MMSE>24). The assessment consists of 6 parts, addressing cognitive, motor and behavioral areas, with a total score of 18 and higher scores indicating better performance. The FDR is a brief staging assessment for patients with frontotemporal dementia that detects differences in disease progression for FTD subtypes over time. This brief interview is conducted with the primary caregiver and consists of 30 items which are categorized as occurring Never, Sometimes or Always. A percentage score is then calculated and converted to a logit score and, ultimately, a severity score. The severity score will range from Very Mild to Profound.

Other measures of efficacy include, increased survival term from the point of diagnosis, following onset of symptoms, is a measure of efficacy. Currently, patients diagnosed with neurodegeneration caused by GRN mutations have a life expectancy of 7-11 years from symptom onset. Another measure of efficacy is stabilization and/or increase of atrophy in the thickness of the middle frontal cortex and parietal regions, which are the most commonly affected brain regions across all clinical presentations in the target population. This may be assessed using MRI or other imaging techniques. Still other assessments include biochemical biomarkers. Levels of PGRN protein in the CSF and plasma are measured as a readout of AAV transduction, and are expected to increase in patients following administration of rAAV1.hPGRN. In other embodiments, CSF levels of neurofilament light chain (NFL), tau, phosphorylated tau, and other inflammatory markers are assessed. In certain embodiments, modulation and/or a decrease of these biomarkers levels correlates to efficacy.

Although the examples below focus on treatment of certain conditions associated with heterozygous GRN haploinsufficiencies, in certain embodiments, the vectors and compositions described herein may be used in treatment of other diseases, e.g., diseases associated with homozygous mutation of the GRN gene such as neuronal ceroil lipofuscinosis, cancer (e.g., ovarian, breast, adrenal, and/or pancreatic cancer), atherosclerosis, type 2 diabetes, and metabolic diseases.

As used herein, the term Computed Tomography (CT) refers to radiography in which a three-dimensional image of a body structure is constructed by computer from a series of plane cross-sectional images made along an axis.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The terms "sequence identity" "percent sequence identity" or "percent identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length and may be up to about 700 amino acids. Examples of suitable fragments are described herein.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. In the examples, AAV alignments are performed using the published AAV9 sequences as a reference point. Alignments are performed using any of a variety of publicly or commercially available Multiple Sequence Alignment Programs. Examples of such programs include, "Clustal Omega", "Clustal W", "CAP Sequence Assembly", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference. Multiple sequence alignment programs are also available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13): 2682-2690 (1999).

It is to be noted that the term "a" or "an" refers to one or more. As such, the terms "a (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% (±10%, e.g., ±1, ±2, ±3, ±4, ±5, ±6, ±7, ±8, ±9, ±10, or values therebetween) from the reference given, unless otherwise specified.

As used herein, "disease", "disorder" and "condition" are used interchangeably, to indicate an abnormal state in a subject.

Unless defined otherwise in this specification, technical and scientific terms used herein have the same meaning as commonly understood by one of ordinary skill in the art and by reference to published texts, which provide one skilled in the art with a general guide to many of the terms used in the present application.

The term "expression" is used herein in its broadest meaning and comprises the production of RNA or of RNA and protein. With respect to RNA, the term "expression" or "translation" relates in particular to the production of peptides or proteins. Expression may be transient or may be stable.

As used herein, an "expression cassette" refers to a nucleic acid molecule which comprises a coding sequence, promoter, and may include other regulatory sequences therefor, which cassette may be delivered via a genetic element (e.g., a plasmid) to a packaging host cell and packaged into the capsid of a viral vector (e.g., a viral particle). Typically, such an expression cassette for generating a viral vector contains the coding sequence for the gene product described herein flanked by packaging signals of the viral genome and other expression control sequences such as those described herein.

As used herein, the term "operably linked" refers to both expression control sequences that are contiguous with the gene of interest and expression control sequences that act in trans or at a distance to control the gene of interest.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

The term "translation" in the context of the present invention relates to a process at the ribosome, wherein an mRNA strand controls the assembly of an amino acid sequence to generate a protein or a peptide.

The following examples are illustrative only and are not intended to limit the present invention.

EXAMPLES

| Abbreviations | Description |
|---|---|
| A | Absorbance |
| aa | Amino Acids |
| AAV | Adeno-Associated Virus |
| AAV1 | Adeno-Associated Virus Serotype 1 |
| AAV2 | Adeno-Associated Virus Serotype 2 |
| AAV5 | Adeno-Associated Virus Serotype 5 |
| AAVhu68 | Adeno-Associated Virus Serotype hu68 |
| ACMG | American College of Medical Genetics |
| AD | Alzheimer's Disease |
| AD & FDM | Alzheimer's Disease and Frontotemporal Dementia Mutation Database |
| Ad5 | Adenovirus Serotype 5 |
| AE | Adverse Events |
| AEX | Anion Exchange |
| AmpR | Ampicillin Resistance (gene) |
| ANOVA | Analysis of Variance |
| ARTFL | Advancing Research and Treatment for Frontotemporal Lobar Degeneration |
| AUC | Analytical Ultracentrifugation |
| BA | β-Actin |
| BCA | Bicinchoninic Acid |
| BDS | Bulk Drug Substance |
| BMCB | Bacterial Master Cell Bank |
| bp | Base Pairs |
| BRF | Batch Record Form |
| BSA | Bovine Serum Albumin |
| BSE | Bovine spongiform encephalopathy |
| BSC | Biological Safety Cabinet |
| bvFTD | Behavioral Variant Frontotemporal Dementia |
| BWCB | Bacterial Working Cell Bank |
| C9orf72 | Chromosome 9 Open Reading Frame 72 (gene, human) |
| cap | Capsid (gene) |
| CB7 | Chicken β-Actin Promoter and CMV enhancer |
| CBC | Complete Blood Count |
| CBER | Center for Biologics Evaluation and Research |
| CBS | Corticobasal Syndrome |
| CDR-FTLD sb | Clinical Dementia Rating (CDR) Scale for Frontotemporal Lobar Degeneration Sum of Boxes |
| CFR | Code of Federal Regulations |
| CFU | Colony Forming Units |
| CGI-C | Clinical Global Impression of Change |
| CI | Chimeric Intron |
| CMC | Chemistry Manufacturing and Controls |
| CMO | Contract Manufacturing Organization |
| CMV IE | Cytomegalovirus Immediate-Early Enhancer |
| CNS | Central Nervous System |
| COA | Certificate of Analysis |
| CPE | Cytopathic Effects |

-continued

| Abbreviations | Description |
|---|---|
| CRL | Charles River Laboratories |
| CRO | Contract Research Organization |
| CSF | Cerebrospinal Fluid |
| C-SSRS | Columbia-Suicide Severity Rating Scale |
| CT | Computed Tomography |
| CTL | Cytotoxic T Lymphocyte |
| CTSD | Cathepsin D |
| ddPCR | Droplet Digital Polymerase Chain Reaction |
| DLS | Dynamic Light Scattering |
| DMEM | Dulbecco's Modified Eagle Medium |
| DMF | Drug Master File |
| DNA | Deoxyribonucleic Acid |
| DO | Dissolved Oxygen |
| DP | Drug Product |
| DRG | Dorsal Root Ganglia |
| DS | Drug Substance |
| E1A | Early Region 1A (gene) |
| ECG | Electrocardiogram |
| EDTA | Ethylenediaminetetraacetic Acid |
| ELISA | Enzyme-Linked Immunosorbent Assay |
| ELISpot | Enzyme-Linked Immunospot |
| EU | Endotoxin Units |
| F | Female |
| F/U | Follow-Up |
| FAB | Frontal Assessment Battery |
| FBI | Frontal Behavioral Inventory |
| FBS | Fetal Bovine Serum |
| FDA | Food and Drug Administration |
| FDP | Filled Drug Product |
| FFB | Final Formulation Buffer |
| FIH | First-in-Human |
| FRS | Frontotemporal Dementia Rating Scale |
| FTD | Frontotemporal Dementia |
| FTLD | Frontotemporal Lobar Degeneration |
| FTDC | International Behavioral Variant FTD Criteria Consortium |
| GC | Genome Copies |
| GENFI | Genetic Frontotemporal Dementia Initiative |
| GLP | Good Laboratory Practice |
| GMP | Good Manufacturing Practice |
| GRN | Granulin Precursor (gene, human) |
| Grn | Granulin Precursor (gene, mouse) |
| GTP | Gene Therapy Program |
| HCDNA | Host Cell Deoxyribonucleic Acid |
| HCP | Host Cell Protein |
| HEK293 | Human Embryonic Kidney 293 |
| HEX | Hexosaminidase (protein) |
| hPGRN | Human Progranulin |
| hPGRN v2 | Human Progranulin version 2 |
| ICH | International Conference on Harmonization |
| ICM | Intra-Cisterna Magna |
| ICP | Intracranial Pressure |
| ICV | Intracerebroventricular |
| IDS | Iduronate-2-Sulfatase |
| IDUA | Iduronidase |
| IFN-γ | Interferon Gamma |
| IND | Investigational New Drug |
| IT | Intrathecally |
| ITFFB | Intrathecal Final Formulation Buffer |
| ITR | Inverted Terminal Repeat |
| IU | Infectious Unit |
| IV | Intravenous |
| KanR | Kanamycin Resistance (gene) |
| kb | kilobases |
| KO | Knockout |
| LAL | Limulus Amoebocyte Lysate |
| LBD | Lewy Body Dementia |
| LEFFTDS | Longitudinal Evaluation of Familial Frontotemporal Dementia Subjects |
| LFTs | Liver Function Tests |
| LLOQ | Lower Limit of Quantification |
| LOD | Limit of Detection |
| LP | Lumbar Puncture |
| LTFU | Long-Term Follow-Up |
| lvPPA | Logopenic Variant Primary Progressive Aphasia |
| M | Male |
| MAPT | Microtubule-Associated Protein Tau (gene, human) |
| MBR | Master Batch Record |
| MCB | Master Cell Bank |

| Abbreviations | Description |
|---|---|
| MED | Minimum Effective Dose |
| MMSE | Mini-Mental State Exam |
| MRI | Magnetic Resonance Imaging |
| mRNA | Messenger Ribonucleic Acid |
| MS | Mass Spectrometry |
| MTD | Maximum Tolerated Dose |
| N | Number of Subjects or Animals |
| N/A | Not Applicable |
| NAbs | Neutralizing Antibodies |
| NCL | Neuronal Ceroid Lipofuscinosis |
| nfvPPA | Nonfluent Variant Primary Progressive Aphasia |
| NFL | Neurofilament Light Chain |
| NGS | Next-Generation Sequencing |
| NHP | Non-Human Primate |
| NHS | Natural History Study |
| NPI | Neuropsychiatric Inventory |
| NSAID | Non-Steroidal Anti-Inflammatory Drug |
| OL | Open-Label |
| PBS | Phosphate-Buffered Saline |
| PD | Parkinson's Disease |
| PEI | Polyethylenimine |
| PES | Polyethersulfone |
| PET | Positron Emission Tomography |
| PGRN | Progranulin (protein) |
| PI | Principal Investigator |
| POC | Proof-of-Concept |
| PolyA | Polyadenylation |
| PPA | Primary Progressive Aphasia |
| PSP | Progressive Supranuclear Palsy |
| QA | Quality Assurance |
| QC | Quality Control |
| qPCR | Quantitative Polymerase Chain Reaction |
| rAAV | Recombinant Adeno-Associated Virus |
| ROA | Route of Administration |
| rcAAV | Replication-Competent Adeno-Associated Virus |
| rBG | Rabbit β-Globin |
| rDNA | Ribosomal Deoxyribonucleic Acid |
| rep | Replicase (gene) |
| RNA | Ribonucleic Acid |
| SA | Single Arm |
| SAE | Serious Adverse Events |
| SDS | Sodium Dodecyl Sulfate |
| SDS-PAGE | Sodium Dodecyl Sulfate Polyacrylamide Gel Electrophoresis |
| SOP | Standard Operating Procedure |
| SRT | Safety Review Trigger |
| ssDNA | Single-Stranded Deoxyribonucleic Acid |
| svPPA | Semantic Variant Primary Progressive Aphasia |
| TBD | To Be Determined |
| $TCID_{50}$ | 50% Tissue Culture Infective Dose |
| TDP-43 | TAR DNA-Binding Protein 43 (protein) |
| TE | Tris-EDTA |
| TFF | Tangential Flow Filtration |
| UbC | Ubiquitin C |
| UCSF | University of California at San Francisco |
| UPenn | University of Pennsylvania |
| UPenn-GTP | University of Pennsylvania Gene Therapy Program |
| UPDRS | Unified Parkinson's Disease Rating Scale |
| UPLC | Ultra-Performance Liquid Chromatography |
| US | United States |
| USP | United States Pharmacopeia |
| WCB | Working Cell Bank |
| WT | Wild Type |

Example 1: Materials and Methods

Vectors

An engineered human PGRN cDNA was cloned into an expression construct containing a chicken beta actin promoter with cytomegalovirus early enhancer, a chimeric intron, and a rabbit beta-globin polyadenylation sequence (FIG. 1). A second engineered human PGRN cDNA was cloned into an expression construct containing the human ubiquitin C promoter. The expression constructs were flanked by AAV2 inverted terminal repeats. Adeno-associated virus serotypes 1, 5 and human 68 (AAVhu68) were generated from this construct by triple transfection of HEK293 cells and iodixanol purification as previously described (Lock M, et al. Hum Gene Ther. 2010; 21(10): 1259-71).

Animal Procedures

All animal protocols were approved by the Institutional Animal Care and Use Committee of the University of Pennsylvania. Breeding pairs of GRN knockout mice were purchased from The Jackson laboratory (stock #013175), and a colony was maintained at the University of Pennsylvania. Wild type C57BL/6 (stock #000664) served as controls. In the first study, mice 2 months of age were anesthetized with isoflurane and injected in the lateral cerebral ventricle (ICV) with $1\times10^{11}$ vector genome copies (GC) in a volume of 5 μL. 60 days post injection mice were euthanized by exsanguination under ketamine/xylazine anesthesia and death was confirmed by cervical dislocation. In the second study, mice were treated at 7 months of age and sacrificed at 11 months of age. At the time of necropsy serum was collected by cardiac puncture and CSF was collected by suboccipital puncture with a 32-gauge needle connected to polyethylene tubing. Serum and CSF samples were immediately frozen on dry ice and stored at −80 degrees until analysis. The frontal cortex was collected for biochemistry and was immediately frozen on dry ice, while the rest of the brain was fixed in 10% formalin for histology.

3-4-year-old rhesus macaques were purchased from Covance. For vector administration, animals were sedated with intramuscular dexmedetomidine and ketamine, and administered a single intra-cisterna magna (ICM) injection of $3\times10^{13}$ GC of an AAV vector in 1 mL artificial CSF. Needle placement was verified via myelography using a fluoroscope (OEC9800 C-Arm, GE), as previously described (Katz N, et al. Hum Gene Ther Methods. 2018 October; 29(5):212-219). Animals were euthanized by barbiturate overdose. Collected tissues were immediately frozen on dry ice or fixed in 10% formalin for histology.

Histology and Imaging

Mouse brains were fixed in 10% formalin, cryo-preserved in sucrose, embedded in optimal cutting temperature (OCT) compound and cryostat sectioned. Low magnification images of autofluorescent material (lipofuscin) of regions of interest were taken. Lipofuscin deposits were quantified in a blinded manner, using Image J software. Nonhuman primate tissues were fixed in 10% formalin, paraffin embedded and stained with Hematoxylin and Eosin (H&E). Slides were reviewed by a board-certified veterinary pathologist (ELB). For animals treated with GFP vectors, brain sections were stained with antibodies against olig2, GFAP, or NeuN. All sections were co-stained with DAPI and an antibody against GFP, followed by fluorescent secondary antibodies. Slides were scanned on a Leica Aperio Versa® 200 slide scanner and downloaded from eSlide Manager to be analyzed on HALO imaging software (Indica Labs). Five regions of the right hemisphere were sampled for each animal, and cells with each cell type marker were quantified. Cells were detected by adjusting the following settings: "minimum nuclear intensity", "nuclear size", "nuclear segmentation aggressiveness", and "minimum nuclear roundness", under the nuclei detection tab. Then, criteria were defined for each individual dye to further identify cells and generate a quantitative total cell count for each marker. Settings were determined empirically based on the sensitivity and reliability of detection the desired cell type; in some cases, settings such as NeuN detection in cytoplasm did not reflect the true intracellular localization of the marker yet provided greater specificity and sensitivity of detection. All cells detected by automated means were manually verified. For neurons, under the "dye 1" tab, the "nucleus positive threshold" and "cytoplasm positive threshold" were adjusted to detect only cells with NeuN present in both the nucleus and cytoplasm. For astrocytes, DAPI and GFAP markers were selected and both had to be present in the nucleus and cytoplasm of a cell for it to be included in the count. For oligodendrocytes, a cell was counted if DAPI and olig2 were both present in the nucleus, but not the cytoplasm of the cell. For colocalization, the same settings were used, however GFP was included as an additional dye in the nucleus for neurons, and in both the nucleus and the cytoplasm for astrocytes. Cells that did not express all selected markers were eliminated from the generated results table by "masking" them using the nucleus or cytoplasm "mask" function. Because of the scarcity of GFP positive cells colocalized with olig2, transduced oligodendrocytes were manually counted. In some cases, blood vessels or portions of the choroid plexus exhibited autofluorescence and were manually outlined and excluded using the "scissors" tool. The resulting values were expressed as percentages of GFP positive cells for each cell type marker.

Sample Preparation for Hexosaminidase (Hex) Assay

Serum was used directly in the Hex activity assay while brain samples were homogenized in lysis buffer (0.2% Triton® X-100, 0.9% NaCl, pH 4.0), followed by three freeze-thaw cycles and clarification by centrifugation. Protein concentrations were determined by Bradford assay. Hex activity measurements were performed as previously described (Hinderer C, et al. Molecular therapy: the journal of the American Society of Gene Therapy. 2014; 22(12): 2018-27).

ELISA

Human PGRN was measured using a DuoSet® ELISA kit (R&D #DY2420) with minor modifications. Briefly, high binding polystyrene ELISA plates were coated over night at 4° C. with 5 ug/ml human PGRN capture antibody diluted in phosphate buffered saline (PBS). After washing, plates were blocked with 1% bovine serum albumin (BSA) in PBS for 2 hours, followed by sample incubation for one hour. Human and nonhuman primate CSF was diluted 1:5, while murine CSF samples were diluted 1:40 in PBS. Brain samples were diluted to 2 mg/ml total protein concentration in lysis buffer. Bound antibody was detected with biotinylated Mouse anti-Human Progranulin antibody and Streptavidin-HRP. Plates were developed using tetramethylbenzidine substrate for 20 minutes then reaction was stopped with 2 N sulfuric acid, before absorbance measurement at 450 nm.

Neutralizing Antibody Assay

Neutralizing antibodies against AAVhu68 were evaluated as previously described (Calcedo R, et al. J Infect Dis. 2009; 199(3):381-90).

Statistics

Comparisons of Hex enzymatic activity, lipofuscin counts and CD68+ area in wild type, GRN knockout and AAV-treated GRN knockout mice, were preformed using one-way ANOVA followed by post-hoc Tukey's multiple comparisons test.

Example 2: AAV-Mediated Delivery of a Human GRN Transgene in a Murine Disease Model Recombinant AAV vectors having AAVhu68 capsids expressing human PGRN (SEQ ID NO: 3) under the control of a CB7 promoter and chimeric intron (CB7.CI.hPGRN.rBG) were produced using published triple transfection technques as described, e.g., WO 2018/160582.

We evaluated AAV-mediated delivery of a human GRN transgene in a GRN knockout mouse model. Mice heterozygous for GRN mutations (GRN$^{+/-}$) do not exhibit pathological hallmarks of GRN-related neurodegenerative disease, likely because the mouse lifespan does not allow for development of the sequelae of GRN haploinsufficiency, which first manifest after several decades in humans. In contrast, complete PGRN deficiency in GRN' mice recapitulates several early hallmarks of GRN haploinsufficieny in humans, such as impaired lysosomal function, accumulation of autofluorescent lysosomal storage material (lipofuscin), and activation of microglia, though GRN$^{-/-}$ mice do not exhibit neuron loss even up to two years of age (Lui H, et al. Cell. 2016; 165(4):921-35; Ward M E, et al. Sci Transl Med. 2017 Apr. 12; 9(385):pii: eaah5642). Both GRN$^{+/-}$ and GRN$^{-/-}$ mice have been reported to exhibit behavior abnormalities, but findings have been inconsistent between groups (Ahmed Z, et al. Am J Pathol. 2010; 177(1):311-24; Wils H, et al. The Journal of Pathology. 2012; 228(1):67-76; Ghoshal N, et al. Neurobiology of Disease. 2012; 45(1):395-408; Filiano A J, et al. The Journal of neuroscience: the official journal of the Society for Neuroscience. 2013; 33(12):5352-61; Yin F, et al. The FASEB Journal. 2010; 24(12):4639-47). Similarly, some reports have indicated reduced survival in GRN$^{-/-}$ mice, whereas others have found that GRN$^{-/-}$ mice have a normal lifespan, consistent with our experience (Ahmed Z, et al. Am J Pathol. 2010; 177(1):311-24; Wils H, et al. The Journal of Pathology. 2012; 228(1):67-76). Although GRN$^{-/-}$ mice do not exhibit overt neurodegeneration or neurological signs, the remarkable biochemical and histological similarities to GRN haploinsufficiency in humans make them a potentially informative model to evaluate novel therapies. We therefore focused our analyses on these biochemical and histological findings in GRN$^{-/-}$ mice.

The aim of this study was to assess whether delivery of the human GRN gene to the brain can eliminate existing lysosomal storage material and normalize lysosome function in GRN$^{-/-}$ mice. In response to lysosomal storage, cells upregulate expression of lysosomal enzymes, which can be used as biomarkers for lysosomal storage diseases (Hinderer C, et al. Molecular therapy: the journal of the American Society of Gene Therapy. 2014; 22(12):2018-27; Gurda B L, et al. Molecular therapy: the journal of the American Society of Gene Therapy. 2016; 24(2):206-16; Karageorgos L E, et al. Experimental Cell Research. 1997; 234(1):85-97). We evaluated the activity of the lysosomal enzyme hexosaminidase in brain tissue from GRN$^{-/-}$ and GRN$^{+/+}$ mice of different ages, as well as lipofuscin deposits in the cortex, hippocampus and thalamus (FIG. 3A-FIG. 3D). Elevated hexosaminidase activity was evident throughout life, whereas lipofuscin exhibited progressive accumulation. Lipofuscin was apparent as early as 2 months of age, consistent with previous findings (Klein Z A, et al. Neuron. 2017; 95(2):281-96 e6). Our initial studies were performed with an AAV vector based on the natural isolate AAVhu68, which is closely related to the clade F isolate AAV9. We treated GRN$^{-/-}$ mice at 2-3 months of age with an intracerebroventricular (ICV) injection of either an AAVhu68 vector expressing human GRN or vehicle (PBS) (N=10 per group). In addition, a cohort of wild type mice was injected with vehicle (N=10). The ICV ROA (involving injection of AAV vector directly into the CSF of the cerebral ventricles) was used because the small size of the 2-month-old mouse makes it challenging to reliably administer vector via the ICM route, which is the ROA that is used for the NHP study and the proposed FIH clinical trial. Previous studies demonstrated that ICV administration of AAVhu68 at the dose selected for this study ($10^{11}$ GC) results in transduction limited to brain regions near the injected ventricle, making this a useful system to evaluate whether global improvements in brain lesions can be achieved through secretion of PGRN by a small population of cells.

Two months after vector administration the animals were euthanized, and brain, CSF and serum were collected. Quantification of human PGRN protein levels in the brain confirmed transduction in the AAV-treated group (FIG. 4A-FIG. 4F). PGRN is a secreted protein that can be measured in the CSF, and is reduced in the CSF of human GRN mutation carriers (Lui H, et al. Cell. 2016; 165(4):921-35; Meeter L H, et al. Dement Geriatr Cogn Dis Extra. 2016; 6(2):330-40). We therefore evaluated PGRN protein levels in the CSF of AAV-treated GRN$^{-/-}$ mice, which revealed an average CSF concentration of 14 ng/mL, while in vehicle-treated groups, human PGRN was below detection levels (FIG. 4A-FIG. 4F). Expression of PGRN was accompanied by normalization of lysosomal enzyme expression, with Hex activity levels returning to near normal levels in the brains of AAV-treated GRN$^{-/-}$ mice (FIG. 4A-FIG. 4F).

After confirming PGRN expression in the brains of GRN$^{-/-}$ mice, we assessed whether PGRN expression reduced the number of lipofuscin deposits in the hippocampus, thalamus and cortex. For that purpose, unstained fixed brain sections were mounted on cover glass and autofluorescent lipofuscin was imaged and quantified in a blinded manner. AAV treated GRN$^{-/-}$ mice exhibited reduced lipofuscin in all brain regions compared to vehicle treated GRN$^{-/-}$ mice, and similar levels to age-matched wild-type controls (FIG. 4A-FIG. 4F).

Figure 6A:
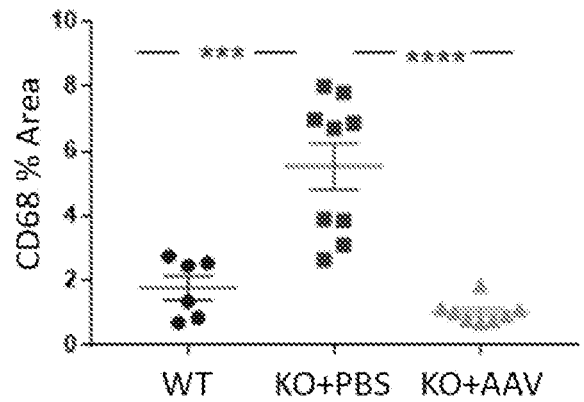
FIG. 6A-FIG. 6C show correction of brain microgliosis in aged $GRN^{-/-}$ mice by AAV-mediated PGRN expression. $GRN^{-/-}$ mice (KO) or $GRN^{+/+}$ (WT) controls were treated with a single ICV injection of vehicle (PBS) or an AAVhu68 vector expressing human PGRN ($10^{11}$ GC) at 7 months of age. Animals were sacrificed 4 months after injection, and brain sections were stained for CD68. CD68 positive areas in images of hippocampus, thalamus and frontal cortex was quantified using ImageJ software by a blinded reviewer (FIG. 6A-FIG. 6C). Areas are expressed per high power field. *$p<0.05$, $p<0.005$, *$p<0.001$, ****$p<0.0001$, one-way ANOVA followed by Tukey's multiple comparisons test.
Figure 6B:
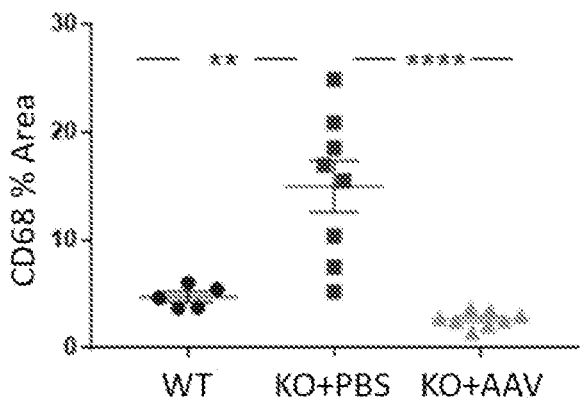
Figure 6C:
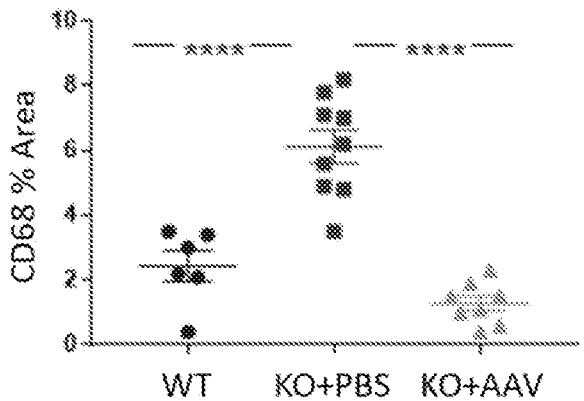

The initial proof of concept study demonstrated the therapeutic activity of AAV-mediated PGRN expression in mice treated at an early age, when storage material has just begun to appear in the brain. We subsequently evaluated the impact of gene transfer in older mice with more severe pre-existing pathology. In this study, 7-month-old GRN$^{-/-}$ mice received a single ICV injection of an AAVhu68 vector expressing human PGRN or vehicle and were sacrificed at 11 months of age. In addition to extensive brain lipofuscin deposits (FIG. 5A-FIG. 5D) 11-month-old GRN$^{-/-}$ mice exhibited extensive microgliosis, similar to patients with FTD caused by GRN mutations (FIG. 6A-FIG. 6C) (Ahmed Z, et al. Journal of neuroinflammation. J Neuroinflammation. 2007 Feb. 11; 4:7). GRN gene transfer reduced brain Hex activity and lipofuscin deposits in aged mice similar to the findings in younger animals (FIG. 5A-FIG. 5D). In addition, the size and number of microglia was normalized in the brains of treated mice (FIG. 6A-FIG. 6C).

Cumulatively, ICV delivery of an AAV vector expressing human PGRN to the brain of GRN$^{-/-}$ mice cleared lipofuscin aggregates and almost fully normalized lysosomal enzymatic activity, demonstrating that PGRN gene delivery can effectively correct key aspects of the underlying pathophysiology of GRN-related neurodegenerative diseases.

Example 3: AAV-Mediated GRN Gene Transfer in Nonhuman Primates

The findings in GRN$^{-/-}$ mice demonstrate that delivery of an AAV vector into the CSF can achieve sufficient brain transduction to produce therapeutic levels of PGRN and prevent or reverse biochemical and histological findings associated with PGRN deficiency. In order to translate this approach to humans, studies were carried out in nonhuman primates using ICM delivery, a clinically relevant route of vector administration. Intrathecal AAV delivery via injection into the cisterna magna is a minimally invasive approach that results in more extensive brain transduction than administration by lumbar puncture (Hinderer C, et al. Molecular therapy Methods & clinical development. 2014; 1:14051). NHPs aged 3-10 years old were utilized because this age is representative of the intended adult patient population. Rhesus macaques (N=2 per group) were administered a single image-guided ICM injection of an AAV1, AAV5, or AAVhu68 vector expressing human GRN from a transgene termed hPGRN (SEQ ID NO: 3) under the control of a chicken BA promoter and CMV IE enhancer (referred to as the CB7 promoter). An additional group was treated with an AAVhu68 vector carrying a different engineered transgene sequence (hPGRN v2, SEQ ID NO: 4) expressed from a ubiquitin C promoter (UbC). Human progranulin levels in CSF were measured weekly, and animals were sacrificed 35 days after injection for analysis of histopathology. Preliminary safety analyses were performed, including daily cage-side observations, serial physical exams, complete blood counts, serum chemistry panels, CSF chemistry and cytology, and a full necropsy with microscopic evaluation of brain and spinal cord. The treatment groups are summarized in the table below.

| Capsid | Transgene | Promoter | Species | N | ROA | Dose | Injection Volume |
|---|---|---|---|---|---|---|---|
| AAVhu68 | hPGRN | CB7 | Adult rhesus macaque | 2 | ICM | $3.00 \times 10^{13}$ GC | 1 mL |
| AAVhu68 | hPGRN v2 | UbC | | 2 | | | |
| AAV1 | hPGRN | CB7 | | 2 | | | |
| AAV5 | hPGRN | CB7 | | 2 | | | |

Figure 7A:
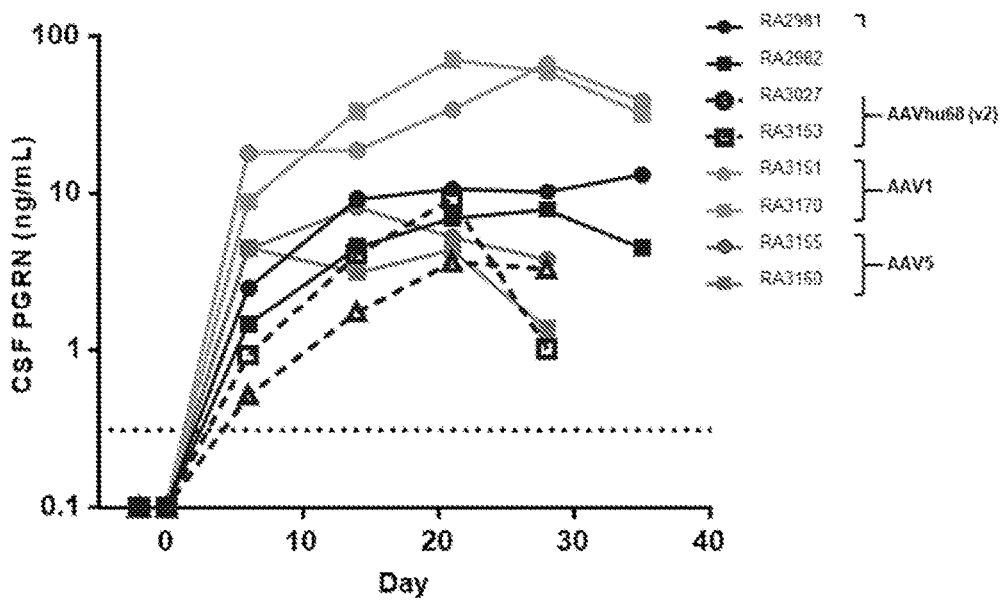
FIG. 7A-FIG. 7C show human PGRN expression in rhesus macaques following AAV delivery. Adult rhesus macaques were administered AAV1, AAV5, or AAVhu68 vectors ($3\times10^{13}$ GC) expressing human PGRN from a chicken beta actin promoter by ICM injection on study day 0 (n=2 per vector). Two additional macaques were administered an AAVhu68 vector expressing hPGRN from a ubiquitin C promoter (AAVhu68 V2). ICM injection was performed under fluoroscopic guidance. After confirming needle placement by fluoroscopy and CSF return injection of contrast material demonstrated distribution within the cisterna magna. Displacement of the contrast was apparent during subsequent vector infusion. Human PGRN was measured in CSF of treated macaques (FIG. 7A) and of healthy adult human subjects (FIG. 7B) and in the serum of treated macaques (FIG. 7C) by ELISA.
Figure 7B:
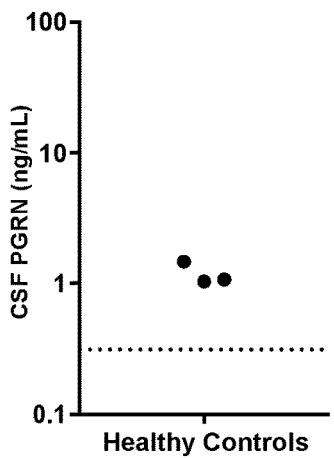
Figure 7C:
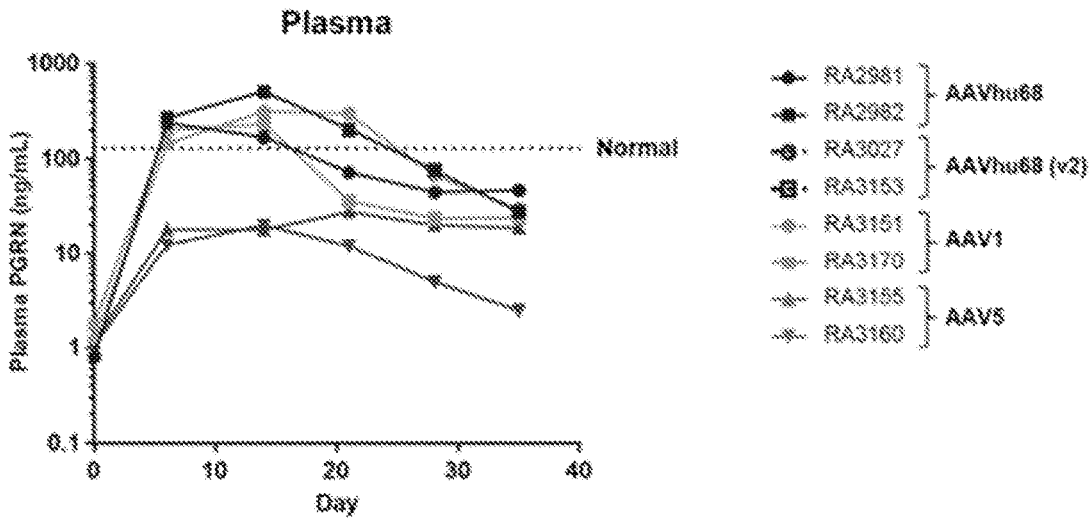

Robust PGRN expression was detected in the CSF of all NHPs following vector administration (FIG. 7A). The two animals treated with the AAVhu68 vector exhibited CSF human PGRN levels up to 10-fold greater than those of healthy human controls, and similar to the levels that reversed lysosomal abnormalities in the brains of $GRN^{-/-}$ mice. AAV5 treatment yielded roughly equivalent CSF expression levels to AAVhu68. Expression of human PGRN was greatest in the animals treated with an AAV1 vector, reaching more than 40-fold normal human levels. CSF and plasma samples from the NHPs treated with AAVhu68 and AAV1 vectors were tested for antibodies to human PGRN. All four animals developed antibodies to the human transgene product (FIG. 8A-FIG. 8C), which may explain the declining expression levels at the end of the study. The onset of the anti-human PGRN antibody response in CSF correlated with transgene expression levels, peaking earlier in the AAV1 group.

ICM AAV delivery was well-tolerated in all treatment groups. No treatment-related abnormalities were identified on daily observations, physical exams, complete blood counts, or serum chemistry panels. Similar to other ICM AAV studies utilizing a xenogenic transgene (Hordeaux J, et al. Mol Ther Methods Clin Dev. 2018; 10(79-88), CSF analysis revealed an asymptomatic lymphocytic pleocytosis beginning 7-21 days after injection for all vector serotypes, mirroring the antibody response to the transgene product (FIG. 8A-FIG. 8C). CSF cell counts declined from peak levels but remained elevated at the time of necropsy for most animals. Histopathology of the brain and spinal cord was evaluated for the AAV1- and AAVhu68-treated groups. Findings were similar to previous ICM AAV studies (Hordeaux J, et al. Mol Ther Methods Clin Dev. 2018; 10:79-88; Hordeaux J, et al. Mol Ther Methods Clin Dev. 2018; 10:68-78), with occasional minimal lymphocytic infiltrates identified in the meninges and choroid plexus, and degeneration of sensory neurons and their associated axons in some dorsal root ganglia (DRG) and spinal cord sections. As in previous ICM AAV studies, the sensory neuron findings were typically minimal to mild in severity and not associated with clinical signs (Gurda B L, et al. Molecular therapy: the journal of the American Society of Gene Therapy. 2016; 24(2):206-16; Hordeaux J, et al. Mol Ther Methods Clin Dev. 2018; 10:79-88; Hordeaux J, et al. Mol Ther Methods Clin Dev. 2018; 10:68-78). No vector-related abnormalities we noted in the brain parenchyma of any animal.

Differing Patterns of CNS Transduction Following ICM Administration of AAV1 and AAVhu68 Vectors to Nonhuman Primates The markedly higher PGRN expression in the CSF of NHPs treated with an AAV1 vector led us to further explore differences in the transduction patterns of AAV1, AAV5, and AAVhu68 vectors. NHPs were administered a single ICM injection of an AAV1, AAV5 or AAVhu68 vector ($3 \times 10^{13}$ GC, n=2 per vector) expressing a GFP reporter gene. Animals were sacrificed 28 days after injection for histological analysis of brain transduction.

Figure 9:
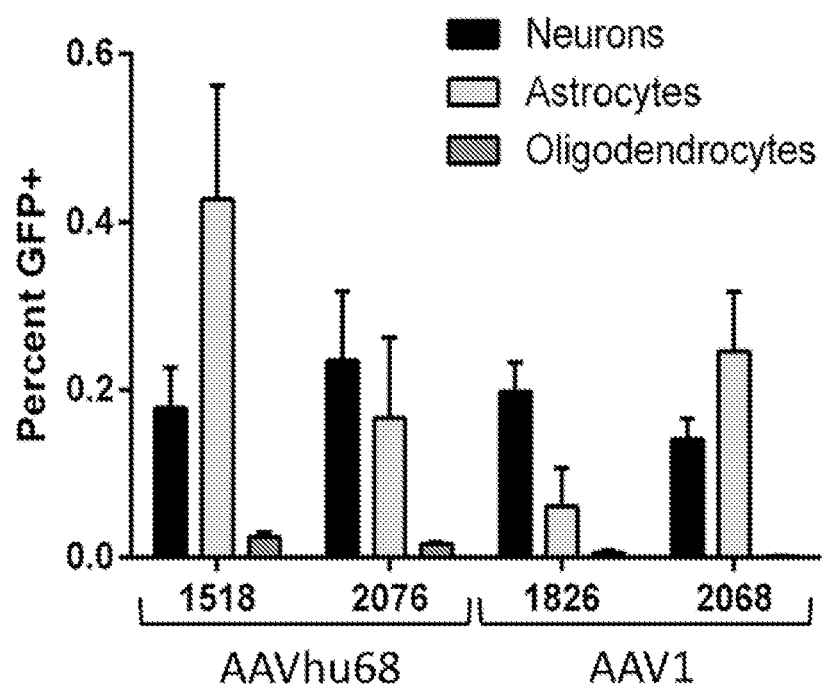
FIG. 9 shows levels of brain transduction following ICM administration of AAV1 and AAVhu68 vectors to nonhuman primates. Adult rhesus macaques were administered $3\times10^{13}$ GC AAVhu68 (n=2) or AAV1 (n=2) vectors expressing GFP from a chicken beta actin promoter by ICM injection. Animals were necropsied 28 days after vector administration, and sections of five regions of the right hemisphere of the brain were analyzed by GFP immunohistochemistry or immunofluorescence with staining for GFP and DAPI. Costaining with markers of specific cell types (NeuN, GFAP and Olig2) allowed for quantification of transduced, astrocytes, and oligodendrocytes. Mean transduction of each cell type was calculated for all sampled brain regions. Error bars=SEM of the five sections.

Immunohistochemistry revealed diffuse, patchy transduction throughout the brains of NHPs treated with AAV1 and AAVhu68 vectors (not shown). Minimal transduction was evident in brain of animals that received the AAV5 vector. In order to more precisely characterize differences in transduction between AAV1 and AAVhu68, a semi-automated method was developed to quantify transduced cells in sections collected from multiple brain regions. Using sections stained with fluorescently labeled antibodies against GFP and markers of specific cell types, the total numbers of neurons, oligodendrocytes and astrocytes were quantified by NeuN, olig2 and GFAP staining, respectively, followed by quantification of GFP expressing cells of each type (FIG. 9, FIG. 10). AAV1 and AAVhu68 each transduced less than one percent of each cell type in all regions examined. Transduction of neurons was nearly equivalent between the two vectors, whereas AAVhu68 appeared to transduce modestly greater numbers of astrocytes and oligodendrocytes.

The roughly equivalent brain transduction observed with AAV1 and AAVhu68 vectors was unexpected, given the dramatically higher CSF PGRN levels achieved with AAV1. Ependymal cell transduction was evaluated by immunohistochemistry in multiple regions of the lateral ventricle and fourth ventricle of animals treated with AAVhu68 and animal RA1826 treated with AAV1. Interestingly, multiple brain sections from an AAV1 treated animal (RA1826) that contained portions of the ventricular system demonstrated extensive transduction of the ependymal cells that line the ventricles, which was not observed in either AAVhu68 treated animal (not shown). An average of 48% of ependymal cells were transduced across all sampled regions, including the frontal, temporal and occipital horn of the lateral ventricle and the fourth ventricle. In contrast, only 1-2% of ependymal cells were transduced in the same brain regions of the animals that were given the AAVhu68 vector. Only small segments of one lateral ventricle were evaluable in the second AAV1-treated animal, which showed approximately 1% ependymal cell transduction, though the analysis was limited to the small sampled region. These findings suggest that highly transduced ependymal cells in AAV1-treated animals could be the source of high levels of PGRN in the CSF, given that the transduction of other cells types appeared similar between the two serotypes. The bystander effect mediated by secreted PGRN makes FTD caused by GRN mutations exceptionally amenable to AAV gene therapy. Since extracellular PGRN can be taken up by neurons, the high CSF PGRN levels achieved with the AAV1 vector—apparently mediated by robust ependymal cell transduction—makes AAV1 an ideal choice for GRN gene therapy.

Example 4: Recombinant AAV1.PGRN rAAV1.PGRN is produced by triple plasmid transfection of HEK293 cells with: 1) the AAV cis plasmid (termed pENN.AAV.CB7.CI.hPGRN.rBG.KanR) encoding the transgene cassette flanked by AAV ITRs, 2) the AAV trans plasmid (termed pAAV2/1.KanR) encoding the AAV2 rep and AAV1 cap genes, and 3) the helper adenovirus plasmid (termed pAdAF6.KanR). The size of the rAAV1.PGRN packaged vector genome is 4129 bases.

A. AAV Vector Genome Plasmid Sequence Elements

Figure 2:
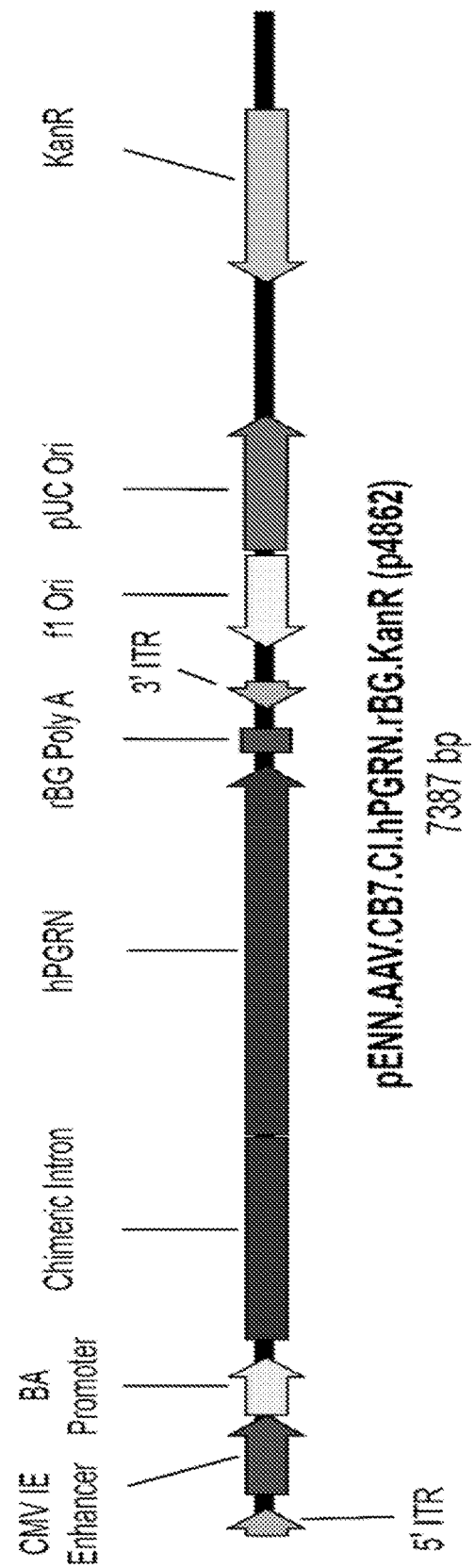
FIG. 2 is a linear vector map of a cis plasmid carrying the vector genome.
Figure 5A:
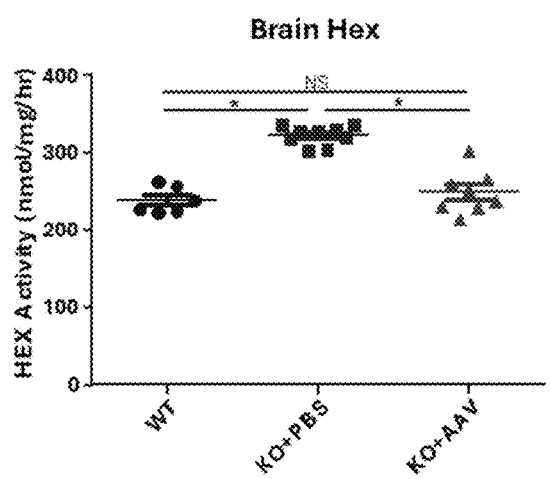
FIG. 5A-FIG. 5D show correction of lysosomal pathology in brains of aged $GRN^{-/-}$ mice by AAV-mediated expression of human PGRN. $GRN^{-/-}$ mice (KO) or $GRN^{+/+}$ (WT) controls were treated with a single ICV injection of vehicle (PBS) or an AAVhu68 vector expressing human PGRN ($10^{11}$ GC) at 7 months of age. Animals were sacrificed 4 months after injection. Hexosaminidase activity was measured in brain samples (FIG. 5A) and lipofuscin deposits were quantified in hippocampus, thalamus and cortex by a blinded reviewer (FIG. 5B-FIG. 5D). Lipofuscin counts are expressed per high power field. *$p<0.05$, **$p<0.005$, one-way ANOVA followed by Tukey's multiple comparisons test.
Figure 5B:
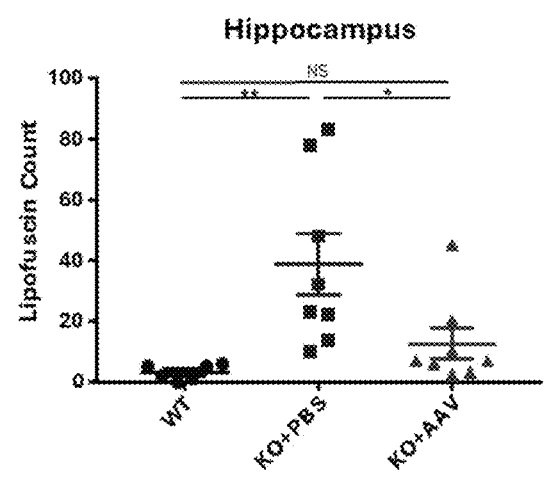
Figure 5C:
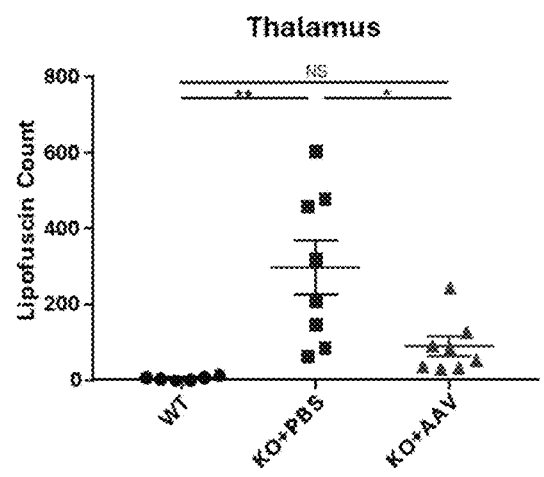
Figure 5D:
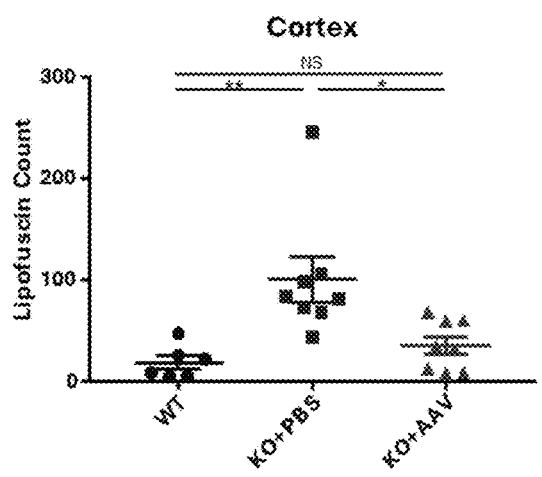

A linear map of the vector genome from the cis plasmid, termed pENN.AAV.CB7.CI.hPGRN.rBG.KanR (p4862). See, FIG. 2.

The cis plasmid contains the following vector genome sequence elements:

1. Inverted Terminal Repeat (ITR): The ITRs are identical, reverse complementary sequences derived from AAV2 (130 base pairs [bp], GenBank: NC_001401) that flank all components of the vector genome. The ITRs function as both the origin of vector DNA replication and the packaging signal for the vector genome when AAV and adenovirus helper functions are provided in trans. As such, the ITR sequences represent the only cis sequences required for vector genome replication and packaging.

2. Human Cytomegalovirus Immediate-Early Enhancer (CMV IE): This enhancer sequence obtained from human-derived CMV (382 bp, GenBank: K03104.1) increases expression of downstream transgenes.

3. Chicken β-Actin Promoter (BA): This ubiquitous promoter (282 bp, GenBank: X00182.1) was selected to drive transgene expression in any CNS cell type.

4. Chimeric Intron (CI): The hybrid intron consists of a chicken β-actin splice donor (973 bp, GenBank: X00182.1) and rabbit β-globin splice acceptor element. The intron is transcribed, but removed from the mature mRNA by splicing, bringing together the sequences on either side of it. The presence of an intron in an expression cassette has been shown to facilitate the transport of mRNA from the nucleus to the cytoplasm, thus enhancing the accumulation of the steady level of mRNA for translation. This is a common feature in gene vectors intended for increased levels of gene expression.

5. Coding sequence: The engineered cDNA of the human GRN gene encodes human PGRN (hPGRN) protein, which is implicated in lysosomal function and other nervous system roles (1785 bp, GenBank: NM_002087.3; 593 amino acids [aa], GenBank: NP_002078).

6. Rabbit β-Globin Polyadenylation Signal (rBG PolyA): The rBG PolyA signal (127 bp, GenBank: V00882.1) facilitates efficient polyadenylation of the transgene mRNA in cis. This element functions as a signal for transcriptional termination, a specific cleavage event at the 3' end of the nascent transcript and the addition of a long polyadenyl tail.

B. AAV1 Trans Plasmid: pAAV2/1.KanR (p0069)

The AAV2/1 trans plasmid is pAAV2/1.KanR (p0069). The pAAV2/1.KanR plasmid is 8113 bp in length and encodes four wild type AAV2 replicase (Rep) proteins required for the replication and packaging of the AAV vector genome. pAAV2/1.KanR also encodes three wild type AAV1 virion protein capsid (Cap) proteins, which assemble into a virion shell of the AAV serotype 1 (AAV1) to house the AAV vector genome. The AAV1 cap genes contained on pAAV2/1.KanR were isolated from a simian source.

To create the pAAV2/1.KanR construct, a 3.0-kilobase (kb) fragment from p5E18(2/2), a 2.3-kb fragment from pAV1H, and a 1.7-kb fragment from p5E18(2/2) were incorporated to form pAAV2/1 (p0001), which contains AAV2 rep and AAV1 cap in an ampicillin resistance (AmpR) cassette (referred to in the literature as p5E18[2/1]). This cloning strategy also relocated the AAV p5 promoter sequence (which normally drives rep expression) from the 5' end of rep to the 3' end of cap, leaving behind a truncated p5 promter upstream of rep. This truncated promoter serves to down-regulate expression of rep and, consequently, maximize vector production (Xiao et al., (1999) Gene therapy vectors based on adeno-associated virus type 1. J Virol. 73(5):3994-4003).

To generate pAAV2/1.KanR for clinical product manufacturing, the ampicillin resistance (AmpR) gene in the backbone sequence of pAAV2/1 was replaced with the kanamycin resistance (KanR) gene. All component parts of the trans plasmids have been verified by direct sequencing.

C. Adenovirus Helper Plasmid: pAdDeltaF6(KanR)

Figure 13:
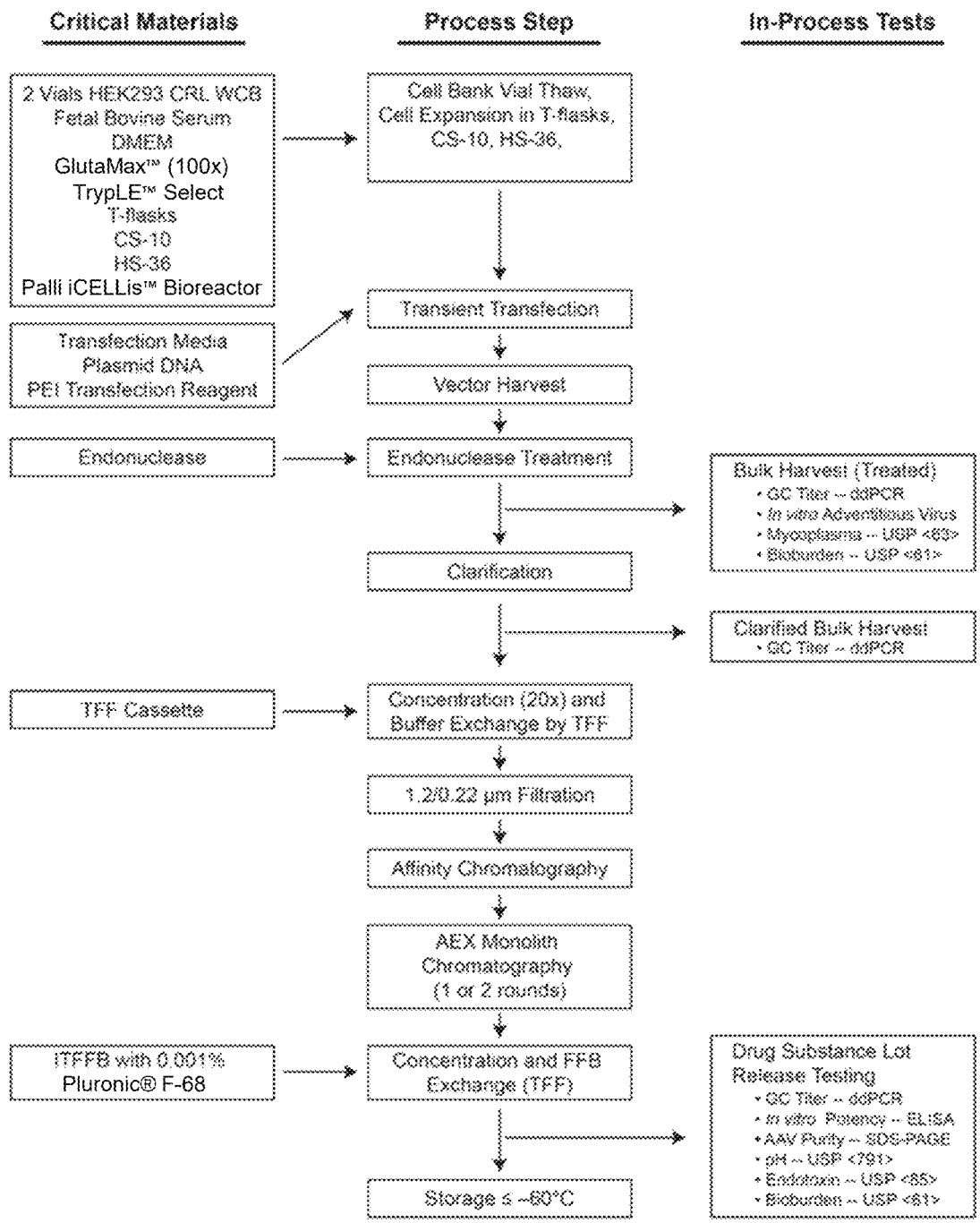
FIG. 13 shows a manufacturing process flow diagram for vector production. Abbreviations: AEX, anion exchange; CRL, Charles River Laboratories; ddPCR, droplet digital polymerase chain reaction; DMEM, Dulbecco's modified Eagle medium; DNA, deoxyribonucleic acid; FFB, final formulation buffer; GC, genome copies; HEK293, human embryonic kidney 293 cells; ITFFB, intrathecal final formulation buffer; PEI, polyethylenimine; SDS-PAGE, sodium dodecyl sulfate polyacrylamide gel electrophoresis; TFF, tangential flow filtration; USP, United States Pharmacopeia; WCB, working cell bank.
Figure 14:
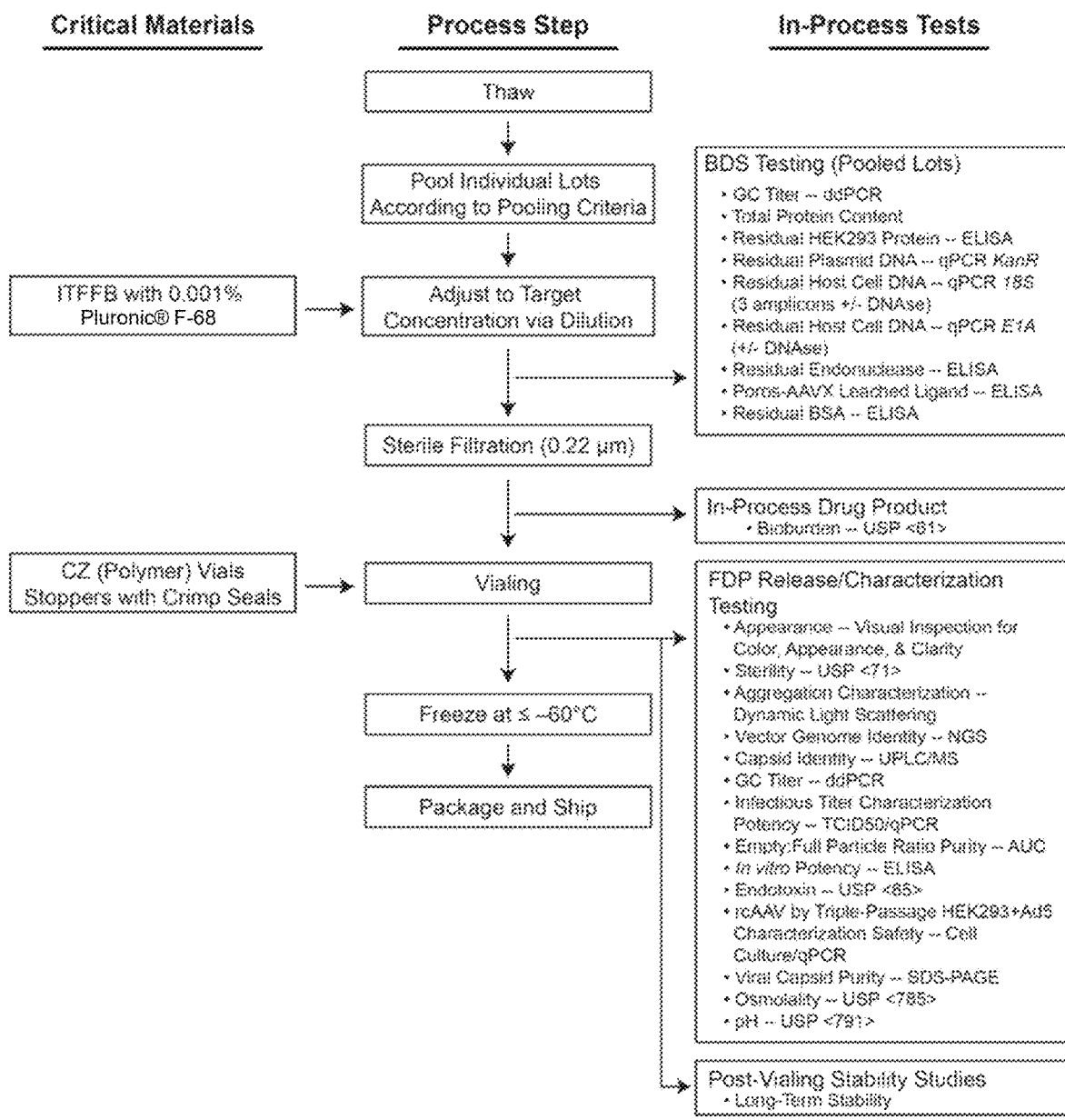
FIG. 14 shows a manufacturing process flow diagram for vector formulation. Manufacturing process for producing GTP-205 drug product. Abbreviations: Ad5, adenovirus serotype 5; AUC, analytical ultracentrifugation; BDS, bulk drug substance; BSA, bovine serum albumin; CZ, Crystal Zenith; ddPCR, droplet digital polymerase chain reaction; E1A, early region 1A (gene); ELISA, enzyme-linked immunosorbent assay; FDP, final drug product; GC, genome copies; HEK293, human embryonic kidney 293 cells; ITFFB, intrathecal final formulation buffer; KanR, kanamycin resistance (gene); MS, mass spectrometry; NGS, next-generation sequencing; qPCR, quantitative polymerase chain reaction; SDS-PAGE, sodium dodecyl sulfate polyacrylamide gel electrophoresis; TCID50 50% tissue culture infective dose; UPLC, ultra-performance liquid chromatography; USP, United States Pharmacopeia.

Plasmid pAdDeltaF6(KanR) was constructed in the laboratory of Dr. James M. Wilson and colleagues at the University of Pennsylvania and is 15,774 bp in size. The plasmid contains the regions of adenovirus genome that are important for AAV replication; namely, E2A, E4, and VA RNA (the adenovirus E1 functions are provided by the HEK293 cells). However, the plasmid does not contain other adenovirus replication or structural genes. The plasmid does not contain the cis elements critical for replication, such as the adenoviral ITRs; therefore, no infectious adenovirus is expected to be generated. The plasmid was derived from an E1, E3-deleted molecular clone of Ad5 (pBHG10, a pBR322-based plasmid). Deletions were introduced into Ad5 to eliminate expression of unnecessary adenovirus genes and reduce the amount of adenovirus DNA from 32 kb to 12 kb). Finally, the ampicillin resistance gene was replaced by the kanamycin resistance gene to create pAdeltaF6(KanR). The E2, E4, and VAI adenoviral genes that remain in this plasmid, along with E1, which is present in HEK293 cells, are necessary for AAV vector production. Vector is produced according to the following flow charts shown in FIG. 13 and FIG. 14.

The final product should have a pH in the range of 6.2 to 7.7, as determined by USP<791>, and an osmolality conent of 260 to 320 mOsm/kg as determined by USP<785>, and a GCtiter of greater than or equal to $2.5 \times 10^{13}$ GC/mL as determined by ddPCR (Lock et al, (2014). "Absolute determination of single-stranded and self-complementary adeno-associated viral vector genome titers by droplet digital PCR." Hum Gene Ther Methods. 25(2):115-25.

Example 5: Identification of the Minimum Effective Dose of rAAV1.PGRN in the GRN$^{-/-}$ Mouse Model

| Dose (GC/g brain mass) | Mouse (GC) | NHP (GC) | Human (GC) |
|---|---|---|---|
| $3.33 \times 10^{11}$ | $1.30 \times 10^{11}$ | $3.00 \times 10^{13}$ | $4.33 \times 10^{14}$ |
| $1.11 \times 10^{11}$ | $4.40 \times 10^{10}$ | $1.00 \times 10^{13}$ | $1.44 \times 10^{14}$ |
| $3.33 \times 10^{10}$ | $1.30 \times 10^{10}$ | $3.00 \times 10^{12}$ | $4.33 \times 10^{13}$ |
| $1.11 \times 10^{10}$ | $4.40 \times 10^{9}$ | — | $1.44 \times 10^{13}$ |

The impact of different doses of rAAV1.PGRN on CNS lesions in the Grn$^{-/-}$ mouse model is assessed as follows. Efficacy is assessed by the extent of reduction in brain storage pathology (lipofuscin) which serves as a quantitative outcome measure that is directly linked to disease pathophysiology. In addition, terminal blood collection for complete blood counts and serum chemistry panels as well as histopathology of target organs are included to identify disease-specific toxicity that may not be detected in the NHP toxicology study. Mice are treated at 5-6 months of age, when extensive lipofuscin storage is present to replicate the disease state in aged subjects with GRN haploinsufficiency. Grn$^{-/-}$ mice receive one of four doses of rAAV1.PGRN ($1.30\times10^{11}$ GC, $4.40\times10^{10}$ GC, $1.30\times10^{10}$ GC, or $4.40\times10^{9}$ GC) or vehicle (ITFFB [artificial CSF with 0.001% Pluronic F-68]) by ICV injection (N=15 per group). Grn$^{-/-}$ mice treated with vehicle (N=15) serve as normal controls. Animals are sacrificed 90 days after treatment, brains are harvested and sectioned, and lipofuscin lesions are quantified. The MED is determined by the dose that shows significant reduction in brain storage lesions relative to vehicle-treated Grn–/– mice and significance is determined using one-way ANOVA followed by Tukey's multiple comparisons test (alpha=0.05), if applicable.

Example 6: Toxicology Study in Non-Human Primates rAAV1.CB7.CI.hPGRN.rBG, is a non-replicating recombinant adeno-associated (AAV) vector consisting of serotype AAV1, which contains an engineered human progranulin (PGRN) cDNA under the control of a chicken beta actin promoter with cytomegalovirus enhancer and a rabbit beta globin polyadenylation sequence flanked by AAV serotype 2 inverted terminal repeats formulated in Intrathecal Final Formulation Buffer (ITFFB). The ddPCR titer was $2.04\times10^{13}$ GC/mL. The pH of the ITFFB was adjusted to pH 7.4 to maximize the solubility of the test article product. Control article(s) were prepared on the day of dosing. Diluted articles are kept on wet ice or at 2-8° C. until dosing on the same day.

A 90-day GLP-compliant safety study in adult rhesus macaques to investigate the toxicology of rAAV1.PGRN following ICM administration was performed. NHPs aged 3-10 years old were utilized for this study because this age is representative of our intended adult human patient population. The 90-day evaluation period was selected because this allows sufficient time for a secreted transgene product to reach stable plateau levels following ICM AAV administration. Rhesus macaques received either one of three dose levels—$3.00\times10^{12}$ GC total, $1.00\times10^{13}$ GC total, or $3.00\times10^{13}$ GC total (N=3 per dose) of rAAV1.hPGRN—or vehicle (ITFFB; N=2). Dose levels were selected to be equivalent to those that are to be evaluated in the planned minimum effective dose (MED) study when scaled by brain mass (assuming 0.4 g for the mouse brain and 90 g for the rhesus macaque brain). Baseline neurologic examinations, clinical pathology (cell counts with differentials, clinical chemistriess, and a coagulation panel), CSF chemistry, and CSF cytology were performed. After rAAV1.PGRN or vehicle administration, the animals were monitored daily for signs of distress and abnormal behavior.

Blood and CSF clinical pathology assessments and neurologic examinations were performed on a weekly basis for 30 days following rAAV1.PGRN or vehicle administration, followed by every 30 days thereafter. At baseline and at each 30-day time point thereafter, anti-AAV1 neutralizing antibodies (Nabs) and cytotoxic T lymphocyte (CTL) responses to AAV1 and the rAAV1.PGRN transgene product were assessed by an interferon gamma (IFN-γ) enzyme-linked immunospot (ELISpot) assay.

| Species | *Macaca mulatta* |
|---|---|
| Synonym | Rhesus Macaques |
| Age of animals at initiation of study | 3-8 years |
| Weight of animals at initiation of study | 3.0-10.0 kg |
| Number of animals used | 11 Total |
|  | 6 Males |
|  | 5 Females |

| Group Designation | 1 | 2 | 3 | 4 |
|---|---|---|---|---|
| rAAV1.PGRN/ITFFB | Vehicle (ITFFB) | rAAV1.PGRN | rAAV1.PGRN | rAAV1.PGRN |
| rAAV1.PGRN Dose (GC) | N/A | $3.0 \times 10^{12}$ | $1.0 \times 10^{13}$ | $3.0 \times 10^{13}$ |
| Number of Macaques | 2 | 3 | 3 | 3 |
| Sex | Both | Both | Both | Both |
| ROA | ICM | ICM | ICM | ICM |
| Administration Volume (mL) | Up to 2.0 | Up to 2.0 | Up to 2.0 | Up to 2.0 |
| Necropsy Day | 90 ± 5 | 90 ± 5 | 90 ± 5 | 90 ± 5 |

Ninety days after rAAV1.PGRN or vehicle administration, animals were euthanized and tissues were harvested for a comprehensive microscopic histopathological examination. In addition, lymphocytes were harvested from the liver, spleen, and bone marrow to evaluate the presence of T cells reactive to both the capsid and transgene product in these organs at the time of necropsy.

Vector biodistribution was evaluated by qPCR in tissue samples. Vector genomes were also quantified in serum and CSF samples. Vector excretion was evaluated by analysis of vector genomes detected in urine and feces. These analyses were performed only for the highest dose cohort because previous studies had demonstrated that the pattern of vector distribution after ICM administration is dose-independent, and higher vector doses yield greater overall signal in the qPCR-based biodistribution assay, allowing for the most sensitivity in the detection of vector deposition in target tissues (Hordeaux et al., 2018b).

Nerve Conduction Velocity Assessment

Animals were sedated with a combination of ketamine/dexmedetomidine. Sedated animals were placed in lateral or dorsal recumbency on a procedure table, with heat packs to maintain body temperature. Electronic warming devices were not recommended due to potential for interference with electrical signal acquisition.

For sensory nerve conduction studies (NCS), the stimulator probe was positioned over the median nerve with the cathode closest to the recording site, and two needle electrodes inserted subcutaneously on digit II at the level of the distal phalanx (reference electrode) and proximal phalanx (recording electrode), while the ground electrode was placed proximal to the stimulating probe (cathode). A pediatric stimulator was used. The elicited responses were differentially amplified and displayed on the monitor. The initial acquisition stimulus strength was set to 0.0 mA in order to confirm a lack of background electrical signal. In order to find the optimal stimulus location, the stimulus strength was increased up to 10.0 mA, and a train of stimuli was generated while the probe was moved along the median nerve until the optimal location was found as determined by a definitive waveform. Keeping the probe at the optimal location, the stimulus strength was progressively increased in a step wise fashion until the peak amplitude response was no longer increasing. Each stimulus response was recorded and saved in the software. Up to 10 maximal stimuli were averaged and reported for the median nerve. The distance (cm) from the recording site to the stimulation cathode was measured and entered into the software and the conduction velocity was calculated using the onset latency of the response and the distance (cm). Both the conduction velocity and the average of the sensory nerve action potential (SNAP) amplitude were reported. The median nerve was tested bilaterally. All raw data generated by the instrument were retained as part of the study file.

Figure 11A:
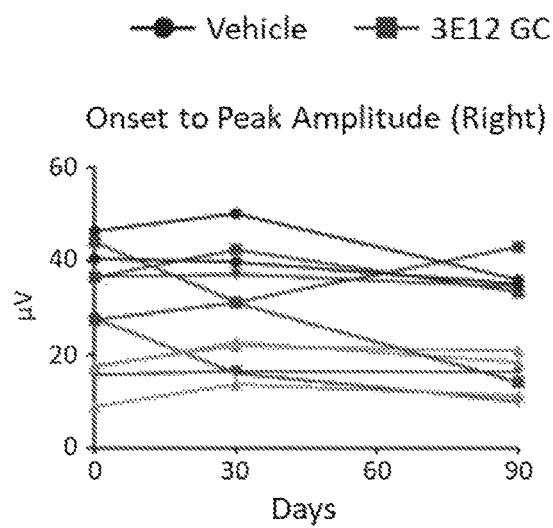
FIG. 11A-FIG. 11B show results from median sensory nerve conduction studies in non-human primates. The Y-axis represents latencies from onset to peak amplitude (peak latency) measured over time (x-axis) following administration of three different doses ($3 \times 10^{12}$ GC, $1 \times 10^{13}$ GC, or $3 \times 10^{13}$ GC of rAAV1.hPGRN or a vehicle control).
Figure 11B:
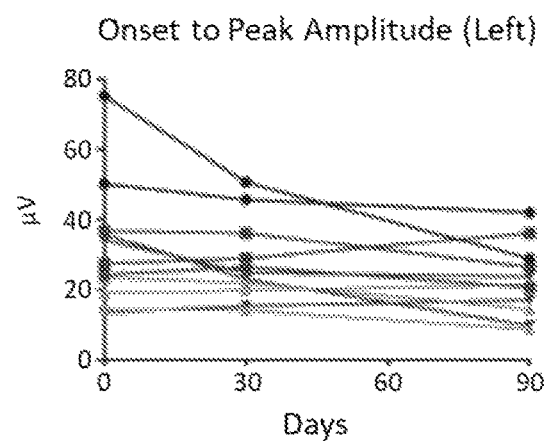
Figure 12A:
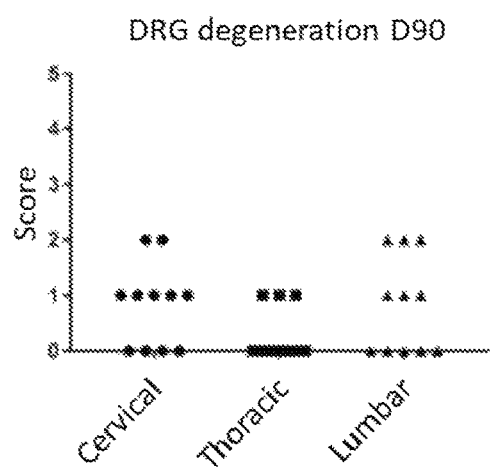
FIG. 12A-FIG. 12D show results from neuropathological studies of dorsal root ganglia (DRG), median nerve, and spinal cord (SC) in non-human primates (NHP), 90 days after treatment with rAAV1.hPGRN.
Figure 12B:
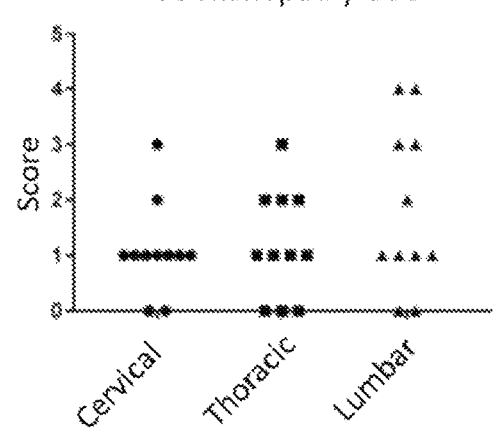
Figure 12C:
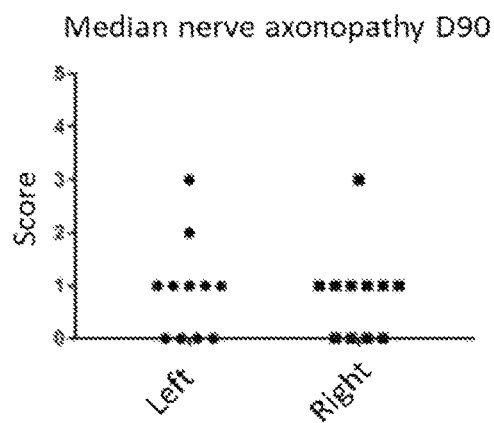
Figure 12D:
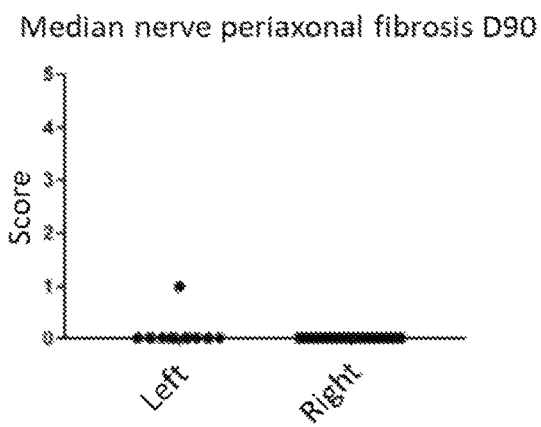

FIG. 11A and FIG. 11B show results from the median sensory nerve conduction studies in NHPs. No effects on median sensory nerve conduction were observed at the doses administered. Preliminary histological analysis showed findings primarily within the DRG, TRG, dorsal white matter tracts of the spinal cord and peripheral nerves (FIG. 12A-FIG. 12D). These findings consisted of neuronal degeneration within the DRG/TRG and axonal degeneration (i.e., axonopathy) within the dorsal white matter tracts of the spinal cord and peripheral nerves. Overall, these findings were observed across all treated groups; however, the incidence and severity tended to be higher in individual animals from the mid and high-dose groups at both time points.

Given the severity of GRN-related neurodegenerative disease, the benefit/risk profile for ICM administration of rAAV1.PGRN is expected to remain favorable.

Example 7: Human Trial

A First-in-Human FIH Phase 1/2 dose escalation study of a single administration of rAAV1.hPGRN in patients with adult-onset neurodegenerative disease caused by mutations in the GRN gene (see table below) is performed. rAAV1.hPGRN is designed to replace the GRN gene. This FIH study evaluates safety and tolerability as well as collect preliminary data on efficacy. Up to 12 symptomatic heterozygous GRN mutation carrier patients are treated with rAAV1.hPGRN and initially followed for a period of 2 years (24 months), with continued long-term follow-up for 5 years post-dose. This study provides data to support initiation of a registrational study which utilizes the Phase 1/2 maximum tolerated dose (MTD). This registrational study evaluates the effect of rAAV1.hPGRN on clinical outcomes and biomarkers relevant to the disease. All trials include administration of a single ICM dose of rAAV1.hPGRN in adult patients with GRN-associated neurodegenerative disease.

| | |
|---|---|
| Protocol(s) Title: | A Phase 1/2 Open-Label, Multi-Center Dose Escalation Study to Assess the Safety and Tolerability of a Single Dose of rAAV1.hPGRN Delivered into the Cisterna Magna (ICM) of Adult Patients with Adult-Onset Neurodegenerative Disease Caused by Heterozygous Mutations in the Granulin Precursor (GRN) Gene |
| Number of Subjects: | Up to 12 evaluable subjects |
| Objectives: | Primary:<br>To assess the safety and tolerability of rAAV1.hPGRN through 2 years (24 months) following administration of a single ICM dose through evaluation of:<br>Adverse events (AEs) and serious adverse events (SAEs)<br>Vital signs and physical examinations<br>Electrocardiograms (ECGs)<br>Sensory nerve conduction studies<br>Laboratory assessments (serum chemistry, hematology, coagulation studies, liver function tests [LFTs], urinalysis, and CSF chemistry and cytology)<br>Immunogenicity of the vector and transgene product<br>Secondary (exploratory efficacy):<br>To assess the pharmacodynamics and biological activity of rAAV1.hPGRN over 2 years (24 months) following administration of a single ICM dose based on the following endpoints:<br>Effect of rAAV1.hPGRN on levels of PGRN protein in CSF<br>Effect of rAAV1.hPGRN on changes in brain cortical thickness<br>To assess the efficacy of rAAV1.hPGRN through 2 years (24 months) following administration of a single ICM dose as measured by:<br>Effect of rAAV1.hPGRN on survival<br>Effect of rAAV1.hPGRN on clinical symptoms and daily functioning as assessed by the Mini-Mental State Exam (MMSE), Clinical Global Impression of Change (CGI-C), Frontal Assessment Battery (FAB), Frontotemporal Dementia Rating Scale (FRS), Frontal Behavioral Inventory (FBI), Unified Parkinson's Disease Rating Scale (UPDRS), verbal fluency testing, Clinical Dementia Rating Scale for Frontotemporal Lobar Degeneration sum of boxes (CDR-FTLD sb), and Neuropsychiatric Inventory (NPI)<br>Exploratory:<br>To further assess the pharmacodynamic effects of rAAV1.hPGRN through 2 years (24 months) following administration of a single ICM dose as measured by:<br>CSF levels of neurofilament light chain (NFL), tau, phosphorylated tau, and inflammatory markers<br>Plasma levels of PGRN |

| | |
|---|---|
| Protocol(s) Title: | A Phase 1/2 Open-Label, Multi-Center Dose Escalation Study to Assess the Safety and Tolerability of a Single Dose of rAAV1.hPGRN Delivered into the Cisterna Magna (ICM) of Adult Patients with Adult-Onset Neurodegenerative Disease Caused by Heterozygous Mutations in the Granulin Precursor (GRN) Gene |
| Study Design: | This is a Phase 1/2, FIH, multi-center, open-label, single-arm, dose escalation study of rAAV1.hPGRN administered by a single ICM injection in adult subjects with adult-onset neurodegenerative disease caused by GRN haploinsufficiency. Safety and tolerability, pharmacodynamics, and clinical efficacy is assessed over 2 years, and all subjects are followed through 5 years post-administration of rAAV1.hPGRN for the long-term evaluation of safety and tolerability, pharmacodynamics, and clinical outcomes.<br>The study consists of a screening phase to determine eligibility of each potential subject from approximately Day −35 to Day −7. After confirmation of subject eligibility and participation in the study, the subject undergoes baseline assessments, which will include brain magnetic resonance imaging (MRI), LP for CSF collection, blood draw, urine collection, vitals, ECG, a physical exam, and clinical assessments. Baseline assessments occur between Day −6 and Day 0 (inclusive) prior to administration of rAAV1.hPGRN. During the treatment phase, subjects are admitted to the hospital on the morning of Day 1. Subjects receive a single ICM dose of rAAV1.hPGRN on Day 1 and remain in the hospital for at least 24 hours after dosing for observation. Subsequent study visits occur at Day 7, Day 14, Day 30, and 6 months after dosing, followed by every 6 months for the first 2 years after dosing.<br>LTFU visits occur for an additional 3 years at a frequency of every 12 months, through 5 years post-dosing.<br>The study consists of the following three cohorts administered rAAV1.hPGRN as a single ICM injection:<br>Cohort 1 (Low Dose): Three eligible subjects are sequentially enrolled and administered the low dose of rAAV1.hPGRN with a 4 week safety observation period between each subject. If no safety review triggers (SRTs) are observed, all available safety data are evaluated by a safety board 4 weeks after the third subject in Cohort 1 is administered rAAV1.hPGRN.<br>Cohort 2 (High Dose): If the decision is made to proceed, three eligible subjects are sequentially enrolled and administered the high dose of hAAV1.hPGRN with a 4 week safety observation period between each subject. If no SRTs are observed, all available safety data are evaluated by the safety board 4 weeks after the third subject Cohort 2 is administered rAAV1.HPGRN.<br>Cohort 3 (MTD): Pending a positive recommendation by the safety board, 6 additional subjects are enrolled and administered the MTD dose of rAAV1.hPGRN. Dosing is not staggered with a 4 week safety observation period between each subject.<br>Cumulatively, a total enrollment of 9 subjects in either the high- or low-dose cohort, and 12 subjects in total (across all doses) is anticipated. |
| Inclusion Criteria: | 1. ≥35 years and ≤75 years of age at enrollment<br>2. Confirmed clinical diagnosis of adult-onset neurodegenerative disease caused by heterozygous GRN mutation<br>3. Confirmation of GRN mutation as causal by one of the following criteria:<br>a. Mutation classified as pathogenic by the Alzheimer Disease & Frontotemporal Dementia Mutation Database (AD&FTDMDB) (AD&FTDMDB and Cruts, (2019). "Alzheimer Disease & Frontotemporal Dementia Mutation Database." Retrieved Jan. 16, 2019, from www.molgen.ua.ac.be/ADmutations/default.cfm?MT=1&ML=1&Page=MutByQue ry&Query=tblContexts.GeneSymbo-1%20In%20(%27GRN%27)&Selection=Gene%20In %20(GRN).) following the guidelines published by the American College of Medical Genetics (ACMG) (Richards et al., (2015). "Standards and guidelines for the interpretation of sequence variants: a joint consensus recommendation of the American College of Medical Genetics and Genomics and the Association for Molecular Pathology." Genet Med. 17(5):405-24)<br>b. Classified as "pathogenic nature unclear" in the AD&FDMDB or "variant of uncertain significance" by ACMG guidelines, and the patient has a family history of the same or related neurodegenerative disease<br>4. CDR-FTLD global score > 0.5 and ≤ 1 |
| Exclusion Criteria: | 1. Inability to provide full consent or the lack of a legally authorized caregiver with adequate contact who can provide consent<br>2. Contraindication to MRI, ICM delivery, or LP (e.g., local infection, thrombocytopenia, coagulopathy, elevated intracranial pressure ([ICP] due to a space-occupying lesion)<br>3. Classification of the GRN mutation as "not pathogenic," "likely benign variant," or "benign variant" in the AD&FDMDB |

| Protocol(s) Title: | A Phase 1/2 Open-Label, Multi-Center Dose Escalation Study to Assess the Safety and Tolerability of a Single Dose of rAAV1.hPGRN Delivered into the Cisterna Magna (ICM) of Adult Patients with Adult-Onset Neurodegenerative Disease Caused by Heterozygous Mutations in the Granulin Precursor (GRN) Gene |
|---|---|
| | 4. Immunocompromised patients
5. Patients with a positive test result for human immunodeficiency virus (HIV) or Hepatitis C
6. Other malignancies or chronic CNS disorders not caused by GRN mutation
7. Medications that, in the opinion of the investigator, may pose a risk to the patient, such as immunosuppressive medications or systemic corticosteroids. Non-steroidal anti-inflammatory drug (NSAID) use acceptable if on a stable dose for 30 days prior to screening and agrees to remain on same dose for duration of trial
8. Malignant neoplasia (except localized skin cancer) or a documented history of hereditary cancer syndrome. Subjects with a prior successfully treated malignancy and a sufficient follow-up to exclude recurrence (based on oncologist opinion) can be included after discussion and approval by the Sponsor or designee
9. Any concurrent disease that, in the opinion of the investigator, may cause cognitive impairment unrelated to GRN mutations, including neurosyphilis, hydrocephalus, stroke, small vessel ischemic disease, uncontrolled hypothyroidism, or vitamin deficiency
10. For females of childbearing potential, a positive urine confirmed by serum pregnancy test at the screening visit, a positive urine confirmed by serum result on Day 1 prior to administration of the investigational product, or unwillingness to have additional pregnancy tests during the study
11. For men and women of childbearing potential, unwillingness to use a medically accepted method of double-barrier contraception (such as a condom/diaphragm used with spermicide) or engage in abstinence from the date of screening to 52 weeks after vector administration
12. Any condition (e.g., history of any disease, evidence of any current disease, any finding upon physical examination, or any laboratory abnormality) that, in the opinion of the investigator, would put the subject at undue risk or would interfere with evaluation of the investigational product or interpretation of subject safety or study results
13. Any acute illness requiring hospitalization within 30 days of treatment |

Route of Administration and Procedure rAAV1.hPGRN as a single dose is administered on Day 1 to subjects via CT-guided sub-occipital injection into the cisterna magna. On Day 1, a syringe containing 5.6 mL of rAAV1.hPGRN at the appropriate titer is prepared by the Investigational Pharmacy associated with the study and delivered to the procedure room.

Prior to study drug administration, the subject is anesthetized, intubated, and the injection site is prepped and draped using sterile technique. An LP is performed to remove a predetermined volume of CSF, after which iodinated contrast is IT injected to aid in visualization of relevant anatomy of the cisterna magna. IV contrast may be administered prior to or during needle insertion as an alternative to the IT contrast. The decision to use IV or IT contrast is at the discretion of the interventionalist performing the procedure. A spinal needle (22-25 G) is advanced into the cisterna magna under fluoroscopic guidance. A larger introducer needle may be used to assist with needle placement. After confirmation of needle placement, the extension set is attached to the spinal needle and allowed to fill with CSF. At the discretion of the interventionalist, a syringe containing contrast material may be connected to the extension set and a small amount injected to confirm needle placement in the cisterna magna. After the needle placement is confirmed, the syringe containing rAAV1.hPGRN is connected to the extension set. The syringe contents are slowly injected over 1-2 minutes, delivering a volume of 5.0 mL.

Safety assessments, including collection of adverse events (AEs), physical/neurologic examinations, vital signs, clinical laboratory (serum chemistry, hematology, coagulation, LFTs, urinalysis), ECGs, nerve conduction studies, and CSF cytology and chemistry (cell counts, protein, glucose) are performed at the times indicated in the study schedule.

No statistical comparisons are planned for safety evaluations; all results are descriptive only. Data are listed and summary tables are produced.

Statistical comparisons are performed for secondary and exploratory endpoints. Measurements at each time point are compared to baseline values for each subject, as well as natural history data from healthy volunteers and GRN patients with comparable cohort characteristics where available for each endpoint. All data are presented in subject data listings. Categorical variables are be summarized using frequencies and percentages, and continuous variables are summarized using descriptive statistics (number of non-missing observations, mean, standard deviation, median, minimum, and maximum). Graphical displays are presented as appropriate.

The early clinical presentation of adult-onset neurodegeneration caused by GRN haploinsufficiency is heterogeneous. This heterogeneity results in a variety of diagnoses with additional symptoms emerging as the disease progresses. Because patients typically decline rapidly following symptom onset, patients with any diagnosis of neurodegeneration may be treated, as long as they have a confirmed pathogenic heterozygous GRN mutation. Patients may be screened utilizing the CDR-FTLD global score. This rating scale is designed to assess disease severity in patients with an FTLD spectrum diagnosis. Due to the overlap in FTLD-related symptomology for those with other GRN-related diagnoses, and the number of domains captured in the CDR-FTLD global score (memory, orientation, judgment and problem solving, community affairs, home and hobbies, personal care, behavior, and language), this scale can be used for diagnoses. A CDR-FTLD global score greater than 0.5 (which includes mildly symptomatic patients) and less than or equal to 1 would permit treatment of symptomatic patients at an early stage of neurodegeneration in which the benefits of gene therapy are likely to be maximized Treating patients at this early stage permits the subsequent detection of changes or stabilization in disease progression and delays in the onset of additional symptoms. However, the requirement of a minimum 0.5 CDR-FTLD global score in this population precludes participation of motor-prominent diagnoses, as the scale is not optimized to capture deficiencies in motor phenotypes.

This gene therapy is not expected to result in PGRN expression above physiological levels. Using rAAV1.hPGRN doses in nonclinical NHP studies that are higher than the doses that would be used in the FIH trial, PGRN was found to be expressed in serum at close to normal levels following rAAV1.hPGRN ICM administration. Because subjects enrolled in the FIH trial would initially have circulating PGRN levels at approximately 30% of normal, it is expected that circulating serum PGRN levels may be restored to normal. Patients' bloodwork is screened through complete blood count (CBC) panels, and patients are monitored for tumors via MRI with gadolinium contrast of the brain and upper spine for 5 years at the follow-up time points.

In addition to measuring safety and tolerability as primary endpoints, secondary and exploratory efficacy endpoints were chosen for this study based on the current literature and in consultation with leading clinicians specializing in the study of GRN-related neurodegeneration. These endpoints track clinical outcomes and disease biomarkers with the goal of identifying appropriate endpoints for a subsequent registrational trial.

Because neurodegeneration caused by GRN mutations ultimately results in death, the impact of rAAV1.hPGRN on patient survival is also an efficacy endpoint for this study. However, the duration of the study and sample size may not be sufficient to demonstrate a survival benefit because most patients have a life expectancy of 7-11 years from symptom onset.

The effect of rAAV1.hPGRN on clinical symptoms and daily functioning of patients is assessed. Because of the phenotypic heterogeneity displayed by the target patient population, functional and clinical scales that capture the progression of symptoms expressed across the range of clinical presentations are employed. The proposed study utilizes the FAB, FRS, MMSE, CGI-C, NPI, and FBI to measure changes over time. These scales primarily measure cognition, language, neuropsychological behaviors, and capabilities related to daily function which inform on the progression or stabilization of the various clinical presentations of the disease. UPDRS is also included to capture changes in motor symptoms. In the FIH, these efficacy assessments are exploratory in nature and intended to capture over time the ability of the rAAV.hPGRN to stabilize the decline in symptoms. Data from the FIH on the rate of further decline across the various clinical parameters in the patients with different clinical presentations are used to further inform the selection of appropriate endpoints and define clinically meaningful changes for the registrational trial.

Each clinical scale is briefly described below:

Clinical Scales Primarily Measuring Cognitive Function

CDR-FTLD: The CDR-FTLD is an extended version of the classic clinical dementia rating (CDR) scale, which is historically used to rate the severity of AD spectrum disorders. The assessment includes the original six domains of the CDR (memory, orientation, judgment and problem solving, community affairs, home and hobbies, personal care). It also includes the two additional domains of language and behavior, which allows for more sensitivity in the detection of decline in FTLD spectrum patients. A rating score of 0 indicates normal behavior or language, while scores of 1, 2, or 3 indicate mild to severe deficits. For the CDR-FTLD sum of boxes (CDR-FTLD sb) represents the sum of the individual domains, and is used to determine global dementia severity.

MMSE: The MMSE is an 11-question global cognitive assessment widely used in clinical and research practice. Questions such as "What is the year? Season? Date? Day of the week? Month?" are asked, and one point is given for each correct answer, with maximum scores provided for each question. The maximum total score is 30, with two cut-offs at scores of 24 and 27. These cutoffs are indicators of cognitive decline.

Verbal Fluency Testing: Although not one of the proposed exploratory efficacy endpoints, verbal fluency testing is performed throughout the FIH trial. This is likely to be conducted by presenting the same picture to each subject and asking for a verbal description. During the description, rate of speech (words/minute) is counted, recorded, and ultimately compared to rates reflective of neuro-typical adults.

Clinical Scales Primarily Measuring Motor Function

UPDRS: The UPDRS is a 42-item, four-part assessment of several domains related to parkinsonism, such as mentation, behavior and mood, and activities of daily living. Each item includes a rating scale ranging from 0 (indicating no impairment) to 4 (indicating the most severe impairment). The scores for each part are tallied to provide an indication of severity of the disease with a high score of 199 indicating the most severe disability.

Clinical Scales Primarily Measuring Behavior

NPI: The NPI is used to elucidate the presence of psychopathology in patients with disorders of the brain. Initially, it was developed for use in AD populations; however, it is believed to be useful for assessing behavioral changes in other conditions. The assessment consists of 10 behavioral domains and two neurovegetative areas, within which there are four scores: frequency, severity, total distress, and caregiver distress. The NPI total score is obtained by adding the domain scores of the behavioral domains and subtracting the caregiver distress scores.

FBI: The FBI is a 24-item assessment of changes in behavior and personality associated specifically with bvFTD and to differentiate between bvFTD and other dementias. It is administered as a face-to-face interview with the primary caregiver because patients with a bvFTD diagnosis generally do not recognize these types of changes. It focuses on several behavioral and personality-related areas, scoring each question from 0 (none) to 3 (severe/most of the time). The total score typically correlates with the severity of illness and can be used to assess change over time.

Clinical Scales Measuring both Cognitive and Motor Function

CGI-C: The CGI-C is one of three parts of a brief, widely used assessment. It is composed of three items that are clinician-rated. The CGI-C is rated on a 7-point scale, ranging from 1 (very much improved) to 7 (very much worse) starting from enrollment in the study, whether or not any improvement is due entirely to treatment.

FAB: The FAB is a brief assessment to assist in differentiating between dementias with a frontal dysexecutive phenotype and those of an AD type. It is particularly useful in mildly demented patients (MMSE>24). The assessment consists of six parts that address cognitive, motor, and behavioral areas. A total score of 18 or higher indicates better performance.

FDR: The FDR is a brief staging assessment for patients diagnosed with a frontotemporal dementia (FTD) subtype (i.e., bvFTD or any of the PPA subtypes). The FDR detects differences in disease progression for FTD over time. This brief interview is conducted with the primary caregiver and consists of 30 items, which are categorized as occurring "never," "sometimes," or "always." A percentage score is then calculated and converted to a logit score and, ultimately, a severity score. The severity score ranges from "very mild" to "profound."

Columbia Suicide Severity Rating Scale (C-SSRS): Although the C-SSRS score is not an exploratory efficacy endpoint for the FIH, this assessment is performed throughout the study. The C-SSRS is a three-part scale measuring suicidal ideation, intensity of ideation, and suicidal behavior. The outcome of this assessment is composed of a suicidal behavior lethality rating taken directly from the scale, a suicidal ideation score, and a suicidal ideation intensity ranking. An ideation score greater than 0 may indicate the need for intervention based on the assessment guidelines. The intensity rating has a range of 0 to 25, with 0 representing no endorsement of suicidal ideation.

As an additional exploratory endpoint, patient survival is assessed. However, patients diagnosed with neurodegeneration caused by GRN haploinsufficiency have a life expectancy of 7-11 years from symptom onset. As such, the duration of the study, sample size, and the inclusion of subjects who are in the early phase of disease may not be sufficient to demonstrate a survival benefit.

Administration of rAAV1.hPGRN stabilize the decline in the atrophy (neuronal cell loss) primarily in the frontal and temporal cortical lobes, and whole brain volume over time caused by GRN-associated haploinsufficiency. MRI may be used to track changes in the thickness of the middle frontal cortex and parietal regions.

Biochemical biomarkers are also assessed. Levels of PGRN protein in the CSF and plasma are measured as a readout of AAV transduction, and increase in patients following administration of rAAV1.hPGRN. CSF levels of neurofilament light chain (NFL), tau, phosphorylated tau, and other inflammatory markers are also be tracked. NFL is considered a general indicator of neuronal loss or damage. Tau and phosphorylated-tau are associated with pathology seen in AD, PD, and some forms of FTD.

Patients' bloodwork is screened through complete blood count (CBC) panels, and patients are monitored for tumors via MRI with gadolinium contrast of the brain and upper spine for 5 years at the follow-up time points.

A single administration of rAAV1.hPGRN is safe and tolerable following administration. A single administration of rAAV1.hPGRN improves survival, and/or reduces disease progression as assessed by clinical symptoms and daily functioning of patients. Treatment slows of loss of neurocognitive function.

SEQUENCE LISTING FREE TEXT

The following information is provided for sequences containing free text under numeric identifier <223>.

| SEQ ID NO | Free Text under <223> |
|---|---|
| 3 | <223> Engineered human PGRN1 coding sequence |
| 4 | <223> engineered hPGRN2 coding sequence |
|  | <220> |
|  | <221> CDS |
|  | <222> (1) . . . (1779) |
| 5 | <223> Synthetic Construct |
| 6 | <223> rabbit globin polyA |
| 7 | <223> 3' AAV ITR |
| 8 | <223> 5' AAV ITR |
| 9 | <223> human CMV IE enhancer |
| 10 | <223> CB promoter |
| 11 | <223> chimeric intron |
| 12 | <223> UbC promoter |
| 13 | <223> intron |
| 14 | <223> SV40 late polyA |
| 15 | <223> Ampicillin resistance gene |
| 16 | <223> COL E1 origin |
| 17 | <223> EF-1a promoter |
| 18 | <223> F1 ori |
| 19 | <223> Kanamycin resistance gene |
| 20 | <223> P5 promoter |
| 21 | <223> LacZ promoter |
| 22 | <223> EF1a.huPGRN.SV40 |
|  | <220> |
|  | <221> repeat_region |
|  | <222> (1) . . . (130) |
| 23 | <223> Ubc.PI.huPGRN.SV40 |
| 24 | <223> CB7.CI.hPGRN1.rBG |
|  | <220> |
|  | <221> misc_feature |
|  | <222> (1) . . . (130) |
|  | <223> 5' ITR |
|  | <220> |
|  | <221> misc_feature |
|  | <222> (198) . . . (579) |
|  | <223> CMV IE enhancer |
|  | <220> |
|  | <221> misc_feature |
|  | <222> (582) . . . (863) |
|  | <223> chicken beta-actin promoter |
|  | <220> |
|  | <221> misc_feature |
|  | <222> (958) . . . (1930) |
|  | <223> chimeric intron |
|  | <220> |
|  | <221> misc_feature |
|  | <222> (1942) . . . (3726) |
|  | <223> hPGRN |
|  | <220> |
|  | <221> misc_feature |
|  | <222> (3787) . . . (3913) |
|  | <223> rabbit beta globin poly A |
|  | <220> |
|  | <221> misc_feature |
|  | <222> (4002) . . . (4131) |
|  | <223> 3' ITR |
| 25 | <223> AAV1 VP1 gene |
|  | <220> |
|  | <221> CDS |
|  | <222> (1) . . . (2208) |
| 26 | <223> Synthetic Construct |
| 27 | <223> AAV2 rep |
| 28 | <223> AAV5 capsid VP1 gene |
|  | <220> |
|  | <221> CDS |
|  | <222> (1) . . . (2172) |
| 29 | <223> Synthetic Construct |
| 30 | <223> AAVhu68 VP1 capsid |

-continued

| SEQ ID NO | Free Text under <223> |
|---|---|
|  | <220> |
|  | <221> CDS |
|  | <222> (1) ... (2211) |
| 31 | <223> Synthetic Construct |
| 32 | <223> miRNA target sequence |
| 33 | <223> miRNA target sequence |
| 34 | <223> miRNA target sequence |
| 35 | <223> miRNA target sequence |

All documents cited in this specification are incorporated herein by reference. U.S. Provisional Patent Application No. 62/809,329, filed Feb. 22, 2019, U.S. Provisional Patent Application No. 62/923,812, filed Oct. 21, 2019, and U.S. Provisional Patent Application No. 62/969,108, filed Feb. 2, 2020, are incorporated by reference in their entireties, together with their sequence listings. The sequence listing filed herewith named "18-8663PCT_ST25.txt" and the sequences and text therein are incorporated by reference. While the invention has been described with reference to particular embodiments, it will be appreciated that modifications can be made without departing from the spirit of the invention. Such modifications are intended to fall within the scope of the appended claims.

The invention claimed is:

1. A recombinant AAV (rAAV) comprising:
   (a) an adeno-associated virus 1 (AAV1) capsid, and
   (b) a vector genome packaged in the AAV1 capsid, said vector genome comprising AAV inverted terminal repeats (ITRs), a coding sequence for human progranulin, and regulatory sequences that direct expression of the human progranulin, wherein the coding sequence for human progranulin is SEQ ID NO: 3 or a sequence at least 95% identical thereto.

2. The rAAV according to claim 1, wherein the coding sequence encodes the human progranulin protein of SEQ ID NO: 1.

3. The rAAV according to claim 1, wherein the vector genome comprises (a) an EF-1a promoter and an SV40 late poly A, (b) a UbC promoter, an intron, and an SV40 late poly A, or (c) a CB7 promoter, a chimeric intron, and a rabbit globin poly A.

4. The rAAV according to claim 3, wherein the vector genome comprises the sequence of SEQ ID NO: 24.

5. A pharmaceutical composition comprising an aqueous liquid suitable for intrathecal administration and a recombinant AAV (rAAV) suitable for use in treating neurodegeneration, said rAAV comprising:
   (a) an adeno-associated virus 1 (AAV1) capsid, and
   (b) a vector genome packaged in the AAV1 capsid, said vector genome comprising AAV inverted terminal repeats (ITRs), a coding sequence for human progranulin, and regulatory sequences that direct expression of the human progranulin, wherein the coding sequence for human progranulin is SEQ ID NO: 3 or a sequence at least 95% identical thereto.

6. The composition according to claim 5, wherein the coding sequence encodes the human progranulin protein of SEQ ID NO: 1.

7. The pharmaceutical composition according to claim 5, wherein the vector genome comprises (a) an EF-1a promoter and an SV40 late poly A, (b) a UbC promoter, an intron, and an SV40 late poly A, or (c) a CB7 promoter, a chimeric intron, and a rabbit globin poly A.

8. The pharmaceutical composition according to claim 7, wherein the vector genome comprises the sequence of SEQ ID NO: 24.

9. The pharmaceutical composition according to claim 5, wherein the pharmaceutical composition comprises an artificial cerebrospinal fluid with a surfactant.

10. The pharmaceutical composition according to claim 9, wherein the surfactant is Poloxamer 188.

11. A recombinant AAV (rAAV) comprising:
    (a) an adeno-associated virus 1 (AAV1) capsid, and
    (b) a vector genome packaged in the AAV1 capsid, the vector genome comprising:
       (i) an enhancer sequence;
       (ii) a chicken beta-actin promoter sequence;
       (iii) an intron sequence;
       (iv) a coding sequence for human progranulin that is SEQ ID NO: 3 or a sequence at least 95% identical thereto; and
       (v) a poly A sequence.

12. The rAAV according to claim 11, wherein the enhancer sequence is a human cytomegalovirus immediate-early enhancer (CMV IE) sequence comprising nucleotides 198 to 579 of SEQ ID NO: 24.

13. The rAAV according to claim 11, wherein the promoter is a chicken beta-actin promoter sequence comprising nucleotides 582 to 863 of SEQ ID NO: 24.

14. The rAAV according to claim 11, wherein the intron sequence is a chimeric intron sequence comprising nucleotides 958 to 1930 of SEQ ID NO: 24.

15. The rAAV according to claim 11, wherein the coding sequence for human progranulin is SEQ ID NO: 3.

16. The rAAV according to claim 11, wherein the poly A sequence is a rabbit globin poly A sequence comprising nucleotides 3787 to 3913 of SEQ ID NO: 24.

17. A pharmaceutical composition comprising the rAAV according to claim 11.

18. The pharmaceutical composition according to claim 17, wherein the pharmaceutical composition comprises an artificial cerebrospinal fluid with a surfactant.

* * * * *